United States Patent
Ramsborg et al.

(10) Patent No.: US 12,296,010 B2
(45) Date of Patent: *May 13, 2025

(54) METHODS FOR ISOLATING, CULTURING, AND GENETICALLY ENGINEERING IMMUNE CELL POPULATIONS FOR ADOPTIVE THERAPY

(71) Applicant: Juno Therapeutics, Inc., Seattle, WA (US)

(72) Inventors: Chris Ramsborg, Seattle, WA (US); Mark L. Bonyhadi, Sammamish, WA (US); Calvin Chan, Seattle, WA (US); Pascal Beauchesne, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/983,137

(22) Filed: Dec. 16, 2024

(65) Prior Publication Data

US 2025/0121062 A1    Apr. 17, 2025

Related U.S. Application Data

(63) Continuation of application No. 18/166,447, filed on Feb. 8, 2023, now Pat. No. 12,208,137, which is a continuation of application No. 17/850,875, filed on Jun. 27, 2022, which is a continuation of application No. 15/305,337, filed as application No. PCT/US2015/027401 on Apr. 23, 2015, now Pat. No. 11,400,115.

(60) Provisional application No. 61/983,415, filed on Apr. 23, 2014.

(51) Int. Cl.
| | |
|---|---|
| A61K 40/31 | (2025.01) |
| A61K 35/12 | (2015.01) |
| A61K 40/11 | (2025.01) |
| A61K 40/42 | (2025.01) |
| C12N 5/0783 | (2010.01) |
| C12N 5/10 | (2006.01) |

(52) U.S. Cl.
CPC ............ *A61K 40/31* (2025.01); *A61K 40/11* (2025.01); *A61K 40/42* (2025.01); *A61K 40/4211* (2025.01); *C12N 5/0636* (2013.01); *C12N 5/10* (2013.01); *A61K 2035/124* (2013.01)

(58) Field of Classification Search
CPC ........ A61K 40/31; A61K 40/11; A61K 40/42; A61K 40/4211; A61K 2035/124; C12N 5/0636; C12N 5/10
USPC ................ 424/93.21, 93.71; 435/344.1, 328
See application file for complete search history.

(56) References Cited

U.S. PATENT DOCUMENTS

| | | |
|---|---|---|
| 4,235,871 A | 11/1980 | Papahadjopoulos |
| 4,361,549 A | 11/1982 | Kung et al. |
| 4,452,773 A | 6/1984 | Molday |
| 4,501,728 A | 2/1985 | Geho |
| 4,690,915 A | 9/1987 | Rosenberg |
| 4,795,698 A | 1/1989 | Owen |
| 4,835,263 A | 5/1989 | Nguyen et al. |
| 4,837,028 A | 6/1989 | Allen |
| 5,019,369 A | 5/1991 | Presant |
| 5,087,616 A | 2/1992 | Myers |
| 5,200,084 A | 4/1993 | Liberti |
| 5,219,740 A | 6/1993 | Miller |
| 5,506,121 A | 4/1996 | Skerra |
| 5,736,137 A | 4/1998 | Anderson et al. |
| 5,773,224 A | 6/1998 | Grandics et al. |
| 5,801,115 A | 9/1998 | Albers et al. |
| 5,985,658 A | 11/1999 | Colinas et al. |
| 6,022,951 A | 2/2000 | Sano et al. |
| 6,103,493 A | 8/2000 | Skerra |
| 6,207,453 B1 | 3/2001 | Maass |
| 6,352,694 B1 | 3/2002 | June et al. |
| 6,410,319 B1 | 6/2002 | Raubitschek |
| 6,451,995 B1 | 9/2002 | Cheung |
| 7,109,304 B2 | 9/2006 | Hansen |
| 7,446,179 B2 | 11/2008 | Jensen |
| 7,446,190 B2 | 11/2008 | Sadelain |

(Continued)

FOREIGN PATENT DOCUMENTS

| | | |
|---|---|---|
| CN | 101 226 118 | 7/2008 |
| CN | 103 305 464 | 9/2013 |

(Continued)

OTHER PUBLICATIONS

Katz et al. (2014) Leukemia & Lymphoma, vol. 55(5), 99-1006.*

(Continued)

*Primary Examiner* — Anne Marie S Wehbe
(74) *Attorney, Agent, or Firm* — MORRISON & FOERSTER LLP

(57) ABSTRACT

The present disclosure relates in some aspects to methods, cells, and compositions for preparing cells and compositions for genetic engineering and cell therapy. Provided in some embodiments are streamlined cell preparation methods, e.g., for isolation, processing, incubation, and genetic engineering of cells and populations of cells. Also provided are cells and compositions produced by the methods and methods of their use. The cells can include immune cells, such as T cells, and generally include a plurality of isolated T cell populations or types. In some aspects, the methods are capable of preparing of a plurality of different cell populations for adoptive therapy using fewer steps and/or resources and/or reduced handling compared with other methods.

20 Claims, 2 Drawing Sheets

Specification includes a Sequence Listing.

(56) References Cited

U.S. PATENT DOCUMENTS

| | | | |
|---|---|---|---|
| 7,482,000 B2 | 1/2009 | DeVaux | |
| 7,837,871 B2 | 11/2010 | Gjerde et al. | |
| 7,981,632 B2 | 7/2011 | Schmidt | |
| 8,389,282 B2 | 3/2013 | Sadelain et al. | |
| 8,911,993 B2 | 12/2014 | June et al. | |
| 9,023,604 B2 | 5/2015 | Schmidt et al. | |
| 9,539,251 B2 | 1/2017 | Sampath et al. | |
| 9,599,590 B2 | 3/2017 | Sabin et al. | |
| 10,228,312 B2 | 3/2019 | Stadler et al. | |
| 10,428,351 B2 | 10/2019 | Crisman et al. | |
| 11,400,115 B2 * | 8/2022 | Ramsborg | A61K 40/4211 |
| 12,208,137 B2 * | 1/2025 | Ramsborg | A61K 40/11 |
| 2002/0131960 A1 | 9/2002 | Sadelain | |
| 2003/0170238 A1 | 9/2003 | Gruenberg | |
| 2003/0175850 A1 | 9/2003 | Ross et al. | |
| 2004/0043401 A1 | 3/2004 | Sadelain | |
| 2004/0082012 A1 | 4/2004 | Busch | |
| 2004/0126363 A1 | 7/2004 | Jensen | |
| 2004/0167319 A1 | 8/2004 | Teeling et al. | |
| 2006/0019319 A1 | 1/2006 | Billadeau et al. | |
| 2006/0106199 A1 | 5/2006 | Erdmann et al. | |
| 2007/0116690 A1 | 5/2007 | Yang et al. | |
| 2007/0241061 A1 | 10/2007 | Engstrom et al. | |
| 2008/0085532 A1 | 4/2008 | Gorlach et al. | |
| 2008/0131415 A1 | 6/2008 | Riddell | |
| 2008/0255004 A1 | 10/2008 | Neurauter et al. | |
| 2009/0035322 A1 | 2/2009 | Martin et al. | |
| 2010/0068738 A1 | 3/2010 | Kawamura et al. | |
| 2010/0104509 A1 | 4/2010 | King et al. | |
| 2011/0003380 A1 | 1/2011 | Miltenyi | |
| 2011/0070581 A1 | 3/2011 | Gupta | |
| 2013/0287748 A1 | 10/2013 | June | |
| 2014/0255993 A1 | 9/2014 | Follstad et al. | |
| 2014/0314795 A1 | 10/2014 | Riddell | |
| 2014/0356398 A1 | 12/2014 | Riddell | |
| 2015/0024411 A1 | 1/2015 | Stadler | |
| 2015/0283178 A1 | 10/2015 | June et al. | |
| 2015/0301046 A1 | 10/2015 | Schmidt | |
| 2015/0306141 A1 | 10/2015 | Jensen | |
| 2016/0045551 A1 | 2/2016 | Brentjens | |
| 2016/0220656 A1 | 8/2016 | Godart | |
| 2016/0362472 A1 | 12/2016 | Bitter et al. | |
| 2017/0037370 A1 | 2/2017 | Kaiser et al. | |
| 2017/0051252 A1 | 2/2017 | Morgan et al. | |
| 2017/0209492 A1 | 7/2017 | June et al. | |
| 2017/0240882 A1 | 8/2017 | Abrams et al. | |
| 2017/0254774 A1 | 9/2017 | Sabin et al. | |
| 2018/0064627 A1 | 3/2018 | Lange et al. | |
| 2018/0296602 A1 | 10/2018 | Riddell et al. | |
| 2019/0226951 A1 | 7/2019 | Stadler et al. | |
| 2019/0234844 A1 | 8/2019 | Stadler et al. | |
| 2020/0354677 A1 | 11/2020 | Lee et al. | |
| 2020/0384025 A1 | 12/2020 | Mujacic et al. | |
| 2021/0163893 A1 | 6/2021 | Westoby et al. | |
| 2023/0087953 A1 | 3/2023 | Westoby et al. | |
| 2023/0090176 A1 | 3/2023 | Ramsborg et al. | |
| 2023/0190798 A1 | 6/2023 | Westoby et al. | |
| 2023/0190814 A1 | 6/2023 | Ramsborg et al. | |
| 2025/0020556 A1 | 1/2025 | Stadler | |

FOREIGN PATENT DOCUMENTS

| | | |
|---|---|---|
| CN | 103 502 438 | 1/2014 |
| EP | 0452342 | 10/1991 |
| EP | 0700430 | 3/1996 |
| EP | 2537416 | 12/2012 |
| EP | 3346001 | 7/2018 |
| EP | 3699268 | 8/2020 |
| WO | WO 1992/008796 | 5/1992 |
| WO | WO 1994/028143 | 12/1994 |
| WO | WO 2000/014257 | 3/2000 |
| WO | WO 2000/043551 | 7/2000 |
| WO | WO 2002/054065 | 7/2002 |
| WO | WO 2002/077018 | 10/2002 |
| WO | WO 2002/077029 | 10/2002 |
| WO | WO 2004/029221 | 4/2004 |
| WO | WO 2004/096975 | 11/2004 |
| WO | WO 2005/050209 | 6/2005 |
| WO | WO 2006/044650 | 4/2006 |
| WO | WO 2006/060878 | 6/2006 |
| WO | WO 2006/130458 | 12/2006 |
| WO | WO 2007/112012 | 10/2007 |
| WO | WO 2007/117602 | 10/2007 |
| WO | WO 2008/011486 | 1/2008 |
| WO | WO 2008/140573 | 11/2008 |
| WO | WO 2009/003493 | 1/2009 |
| WO | WO 2009/072003 | 6/2009 |
| WO | WO 2009/072006 | 6/2009 |
| WO | WO 2009/091826 | 7/2009 |
| WO | WO 2009/092068 | 7/2009 |
| WO | WO 2009/097119 | 8/2009 |
| WO | WO 2010/033140 | 3/2010 |
| WO | WO 2011/107489 | 9/2011 |
| WO | WO 2012/017081 | 2/2012 |
| WO | WO 2012/081650 | 6/2012 |
| WO | WO 2012/129514 | 9/2012 |
| WO | WO 2013/011011 | 1/2013 |
| WO | WO 2013/038272 | 3/2013 |
| WO | WO 2013/062365 | 5/2013 |
| WO | WO 2013/123061 | 8/2013 |
| WO | WO 2013/124474 | 8/2013 |
| WO | WO 2013/126726 | 8/2013 |
| WO | WO 2014/011996 | 1/2014 |
| WO | WO 2014/031687 | 2/2014 |
| WO | WO 2014/055668 | 4/2014 |
| WO | WO 2014/076277 | 5/2014 |
| WO | WO 2014/165707 | 10/2014 |
| WO | WO 2014/186469 | 11/2014 |
| WO | WO 2015/095895 | 6/2015 |
| WO | WO 2015/157252 | 10/2015 |
| WO | WO 2015/157384 | 10/2015 |
| WO | WO 2015/157399 | 10/2015 |
| WO | WO 2015/158868 | 10/2015 |
| WO | WO 2015/162211 | 10/2015 |
| WO | WO 2015/164594 | 10/2015 |
| WO | WO 2015/164675 | 10/2015 |
| WO | WO 2015/164745 | 10/2015 |
| WO | WO 2015/168613 | 11/2015 |
| WO | WO 2016/019300 | 2/2016 |
| WO | WO 2016/033570 | 3/2016 |
| WO | WO 2016/069282 | 5/2016 |
| WO | WO 2016/069283 | 5/2016 |
| WO | WO 2016/073602 | 5/2016 |
| WO | WO 2016/090190 | 6/2016 |
| WO | WO 2016/090369 | 6/2016 |
| WO | WO 2016/094304 | 6/2016 |
| WO | WO 2016/109410 | 7/2016 |
| WO | WO 2016/164580 | 10/2016 |
| WO | WO 2017/015427 | 1/2017 |
| WO | WO 2017/015490 | 1/2017 |
| WO | WO 2017/023803 | 2/2017 |
| WO | WO 2017/027291 | 2/2017 |
| WO | WO 2017/068421 | 4/2017 |
| WO | WO 2017/096329 | 6/2017 |
| WO | WO 2017/156479 | 9/2017 |
| WO | WO 2017/157505 | 9/2017 |
| WO | WO 2017/161353 | 9/2017 |
| WO | WO 2018/106732 | 6/2018 |
| WO | WO 2018/191723 | 10/2018 |
| WO | WO 2019/089855 | 5/2019 |
| WO | WO 2019/113557 | 6/2019 |
| WO | WO 2020/033927 | 2/2020 |
| WO | WO 2021/163389 | 8/2021 |
| WO | WO 2021/163391 | 8/2021 |

OTHER PUBLICATIONS

Jethwa et al. (2014) Clinical Immunology, vol. 150, 51-63.*
Marcus et al. (2014) Exp. Opin. Biol. Ther., vol. 14:7, 947-954.*
Mei et al. (2012) Arthritis Research & Therapy, vol. 14 (Suppl 5): S1, pp. 1-16.*
U.S. Appl. No. 19/029,968, filed Jan. 17, 2025, by Ramsborg et al.
U.S. Appl. No. 19/030,019, filed Jan. 17, 2025, by Ramsborg et al.

(56) References Cited

OTHER PUBLICATIONS

U.S. Appl. No. 19/030,056, filed Jan. 17, 2025, by Ramsborg et al.
Actemra® [Prescribing Information]. South San Francisco, USA: Genentech Inc. Available from: URL: https://www.accessdata.fda.gov/drugsatfda_docs/label/2013/125276309 2lbl.pdf.
Adams et al., "A pilot study: use of fludarabine for refractory dermatomyositis and polymyositis, and examination of endpoint measures." The Journal of Rheumatology 26.2 (1999): 352-360.
Akron Biotech "Exceptional purity, consistency and performance. Expand T-Cells and NK-Cells with Akron's cGMP IL-15," (Aug. 2023):1-9.
Aksoy et al., "Human primary T cells: A practical guide," dated Jun. 19, 2018. Retrieved from https://peerj.com/preprints/26993.html.
Alarcon et al., "Effect of hydroxychloroquine on the survival of patients with systemic lupus erythematosus: data from Lumina, a multiethnic US cohort (Lumina L)," Ann Rheum Dis (2007) 66:1168-1172.
Al-Shanti et al., "Human purified CD8+ T cells: Ex vivo expansion model to generate a maximum yield of functional cytotoxic cells," Immunol Invest. (Jan. 2007) 36(1):85-104.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93, 11 pages.
Amadori et al., "Genetic control of the CD4/CD8 T-cell ratio in humans," Nature Med. (1995) 1: 1279-1283.
American Academy of Dermatology Ad Hoc Task Force for the ABCDEs of Melanoma et al., "Early detection of melanoma: reviewing the ABCDEs," J Am Acad Dermatol (2015) 72(4):717-723.
Amos et al., "The role of caspase 3 and BclxL in the action of interleukin 7 (IL-7): a survival factor in activated human T cells," Cytokine. (1998) 10(9):662-8.
Anonymous, "Scientists helping scientists™ | WWW Optimization of Human T Cell Expansion Protocol: Effects of Early Cell Dilution," (2018).
"Antisynthetase-Syndrome," Retrieved Jul. 26, 2024; Retrieved from https://understandingmyositis.org/myositis/antisynthetase-syndrome/.
Applikon Biotechnology/BioPharma-Reporter (2016) How automation has changed the way we count cells BioPharma-Reporter.com; 1-4 (Year: 2016).
Arbuckle et al., "Development of Autoantibodies before the Clinical Onset of Systemic Lupus Erythematosus," N Engl J Med (2003) 349:1526-1533.
Arnett et al., "The American Rheumatism Association 1987 revised criteria for the classification of rheumatoid arthritis," Arthritis Rheum. (1988) 31(3):315-24.
Bachmann et al., "Functional Properties and Lineage Relationship of CD8+ T Cell Subsets Identified by Expression of IL-7 Receptor and CD62L," J. Immunol. (2005) 175:4686-96.
Barrett et al., "The length and mode of termination of individual muscle fibers in the human Sartorius and posterior femoral muscles," Cell Tissues Organs (1962) 48(3):242-257.
Baum et al., "Retrovirus vectors: toward the plentivirus?," Molecular Therapy: The Journal of the American Society of Gene Therapy (2006) 13:1050-1063.
Bazzan et al., "Systemic lupus erythematosus and thrombosis," Thromb J. (2015) 13:16. doi: 10.1186/s12959-015-0043-3.
Berger et al., "Adoptive transfer of effector CD8 T cells derived from central memory cells establishes persistent T cell memory in primates." J Clin Invest (2008) 118(1): 294-305.
Bergmann et al., "6 Months-follow up Data of Systemic Sclerosis Patients Treated with CD 19 Targeting CAR-T Cells," American College of Rheumatology, Meeting: ACR Convergence 2023, Session date: Wednesday, Nov. 15, 2023, Abstract No. 2598, 2 pages, retrieved from: https://acrabstracts.org/abstract/6-months-follow-up-data-of-systemic-sclerosis-patients-treated-with-cd-19-targeting-car-t-cells/.
Berthois et al., "Phenol red in tissue culture media is a weak estrogen: Implications concerning the study of estrogen-responsive cells in culture," Proc. Natl. Acad. Sci (1986) 83: 2496-2500.
Bes et al., "Mapping the paratope of anti-CD4 recombinant Fab 13B8.2 by combining parallel peptide synthesis and site-directed mutagenesis," J. Biol. Chem. (2003) 278:14265-14273.
Bohan et al., "Polymyositis and Dermatomyositis: (Second of Two Parts)," New England Journal of Medicine (1975), 292.8, p. 403-407.
Bondanza et al., "IL-7 receptor expression identifies suicide gene-modified allospecific CD8+ T cells capable of self-renewal and differentiation into antileukemia effectors," Blood. (Jun. 2011) 117(24):6469-6478.
Boris-Lawrie et al., "Recent advances in retrovirus vector technology," Cur. Opin. Genet. Develop. (1993) 3:102-109.
Bostrom et al., "High Affinity Antigen Recognition of the Dual Specific Variants of Herceptin Is Entropy-Driven in Spite of Structural Plasticity," PLOS One (2011) 6(4):e17887.
Boyman et al., "The role of interleukin-2 in memory CD8 cell differentiation," Adv Exp Med Biol (2010) 684:28-41.
Brady et al., "HIV integration site distributions in resting and activated CD4+ T cells infected in culture," AIDS. (2009) 23(12):1461-71.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Braun et al., "Rapid separation of T cell subpopulations with monoclonal antibodies and affinity chromatography," J Immunological Methods (1982) 54:251-258.
Brentjens et al., "Safety and persistence of adoptively transferred autologous CD19-targeted T cells in patients with relapsed or chemotherapy refractory B-cell leukemias," Blood (2011) 118(18):4817-4828.
Brentjens, R., "Dosing Strategies: Goals and Options" Slide Deck of Oral Presentation made at NIH T cell Immunotherapy—Optimizing Trial Design Symposium, Bethesda, MD (Sep. 10, 2013) 14 pages, Retrieved from the Internet: URL: http://osp.od.nih.gov/sites/default/files/3_Brentjens_s3.pdf [retrieved on Dec. 28, 2016].
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Burt et al., "Nonmyeloablative Hematopoietic Stem Cell Transplantation for Systemic Lupus Erythematosus," JAMA (2006) 295(5):527-535.
Burt et al., "Hematopoietic stem cell transplantation for autoimmune diseases: What have we learned?" J Autoimmunity (2008) 30(3):116-120.
Butler et al., "Ex Vivo Expansion of Human CD8+ T Cells Using Autologous CD4+ T Cell Help," PLoS ONE (2012) 7(1): e30229.
Caggiari et al., "Different rates of CD4+ and CD8+ T-cell proliferation in interleukin-2-treated human immunodeficiency virus-positive subjects," Cytometry (2001) 46(4): 233-237.
Cambridge et al., "B cell depletion therapy in systemic lupus erythematosus: Effect on autoantibody and antimicrobial antibody profiles." Arthritis Rheum. (2006) 54(11): 3612.
Cambridge et al., "B cell depletion therapy in systemic lupus erythematosus: relationships among serum B lymphocyte stimulator levels, autoantibody profile and clinical response," Ann Rheum Dis. (2008) 67(7):1011-6.
Carlens et al., "Ex vivo T lymphocyte expansion for retroviral transduction: influence of serum-free media on variations in cell expansion rates and lymphocyte subset distribution," Exp Hematol (2000) 28(10): 1137-1146.
Casalegno-Gardua et al., "Multimer technologies for detection and adoptive transfer of antigen-specific T cells," Cancer Immunology (2009) 59(2):195-202.
Casati et al., "Clinical-scale selection and viral transduction of human naïve and central memory CD8+ T cells for adoptive cell therapy of cancer patients," Cancer Immunology (2013) 62(10): 1563-1573.

(56) References Cited

OTHER PUBLICATIONS

Casati et al., "Enrichment, stimulation, and viral transduction of naive and central memory CD8+ T cells under GMP conditions for translational research towards the development of adoptive cell therapy of cancer patients," MACS&more (2013) 15:20-24.

Cattoglio et al., "Hot spots of retroviral integration in human CD34+ hematopoietic cells," Blood. (2007) 110(6):1770-8.

Cavalieri et al., "Human T lymphocytes transduced by lentiviral vectors in the absence of TCR activation maintain an intact immune competence," Blood (2003) 102(2): 497-505.

Cervera et al., "Morbidity and mortality in systemic lupus erythematosus during a 10-year period: a comparison of early and late manifestations in a cohort of 1,000 patients," Medicine (Baltimore) (2003) 82(5):299-308.

Cervera et al., "Systemic lupus erythematosus: clinical and immunologic patterns of disease expression in a cohort of 1,000 patients. The European Working Party on Systemic Lupus Erythematosus," Medicine (Baltimore). (1993) 72(2):113-24.

Chakravarti et al., "The CD4/CD8 ratio: message in a bottle?" Nature Med. (1995) 1:1240-1241.

Chang et al., "Investigation of interfacial properties of pure and mixed poloxamers for surfactant-mediated shear protection of mammalian cells," Colloids Surf B Biointerfaces. (Aug. 2017) 156:358-365.

Chang et al., "Identification and selective expansion of functionally superior T cells expressing chimeric antigen receptors," J Transl Med (2015) 13(1):161.

Chen et al., "CD8 T cells specific for human immunodeficiency virus, Epstein-Barr virus, and cytomegalovirus lack molecules for homing to lymphoid sites of infection," Blood. (2001) 1;98(1):156-64.

Chicaybam et al., "An efficient low cost method for gene transfer to T lymphocytes," PLoS ONE (2013) 8(3): e60298, 11 pages.

Cho et al., "Human mammalian cell sorting using a highly integrated micro-fabricated fluorescence-activated cell sorter (microFACS)," Lab Chip (2010) 10: 1567-1573.

Church et al., "Tumor-specific CD4+ T cells maintain effector and memory tumor-specific CD8+ T cells," Eur J Immunol (2013) 44(1):69-79.

Clementi et al., "CD4 and CD8 T lymphocyte inheritance. Evidence for major autosomal recessive genes," Hum. Genet. (1999) 105: 337-342.

Clinical Trial Study Record No. NCT00730639. "A Phase 1 Study of Nivolumab (BMS-936558) in Subjects With Advanced or Recurrent Malignancies (MDX1106-03)," First posted Oct. 30, 2008. Last updated Dec. 3, 2021.

Cohen et al., "Recognition of fresh human tumor by human peripheral blood lymphocytes transduced with a bicistronic retroviral vector encoding a murine anti-p53 TCR," J Immunol. (2005) 175:5799-5808.

Coiffier et al., "Long-term outcome of patients in the LNH-98.5 trial, the first randomized study comparing rituximab-CHOP to standard CHOP chemotherapy in DLBCL patients: a study by the Groupe d'Etudes des Lymphomes de l'Adulte," Blood. (2010) 116(12):2040-2045.

Cooper et al., "T-cell clones can be rendered specific for CD19: toward the selective augmentation of the graft-versus-B-lineage leukemia effect," Blood. (2003) 101:1637-1644.

Corada et al., "Monoclonal antibodies directed to different regions of vascular endothelial cadherin extracellular domain affect adhesion and clustering of the protein and modulate endothelial permeability," Blood (2001) 97:1679-1684.

Cordeiro et al., "Treatment of inflammatory myopathies," Postgrad Med J (2006) 82(969):417-424.

Corral-Gudino et al., "Overall survival, renal survival and relapse in patients with microscopic polyangiitis: a systematic review of current evidence," Rheumatology (2011) 50(8):1414-1423.

Couzin et al., "Gene therapy. As Gelsinger case ends, gene therapy suffers another blow," Science (2005) 307(5712):1028.

Dainiak et al., "Methods in Cell Separations." Adv Biochem Eng Biotechnol. (2007) 106:1-18.

Davila et al., "CD19 CAR-targeted T cells induce long-term remission and B Cell Aplasia in an immunocompetent mouse model of B cell acute lymphoblastic leukemia," PLoS ONE (2013) 8(4): e61338, 14 pages.

Davila et al., "How do CARs work?: Early insights from recent clinical studies targeting CD19," Oncoimmunology (2012) 1(9):1577-1583.

Davis et al., "Assessment of a positive selection technique using an avidin column to isolate human peripheral blood T cell subsets," J Immunol Methods. (1994) 175(2):247-57.

Dayal et al., "SLE/myositis overlap: are the manifestations of SLE different in overlap disease?" Lupus. (2002) 11(5):293-298.

Dilillo et al., "Maintenance of Long-Lived Plasma Cells and Serological Memory Despite Mature and Memory B Cell Depletion during CD20 Immunotherapy in Mice1," J Immunol (2008) 180(1):361-371.

Donahue et al., "Helper virus induced T cell lymphoma in nonhuman primates after retroviral mediated gene transfer," J Exp Med (1992) 176(4): 1125-1135.

Dong, Modern Biology, Beijing Institute of Technology Press, 1st edition, p. 328, Jul. 31, 2016 (Article in Chinese; English translation provided).

Dupont et al., "Comparative dose-responses of recombinant human IL-2 and IL-7 on STAT5 phosphorylation in CD4+FOXP3 cells versus regulatory T cells: A whole blood perspective," Cytokine (2014) 69(1):146-149.

Eaker et al., "Concise review: guidance in developing commercializable autologous/patient-specific cell therapy manufacturing," Stem Cells Transl Med. (2013) 2(11): 871-83.

Farge et al., "Autologous hematopoietic stem cell transplantation for autoimmune diseases: an observational study on 12 years' experience from the European Group for Blood and Marrow Transplantation Working Party on Autoimmune Diseases," Haematologica (2010) 95(2):284-292.

Fernandes et al., "Kinetics of class II MHC expression on cytotoxic T cells generated by skin allograft," Tissue Antigens. (1990) 36(3):93-9.

Finney et al., "Activation of resting human primary T cells with chimeric receptors: costimulation from CD28, inducible costimulator, CD134, and CD137 in series with signals from the TCR zeta chain," J Immunol. (Jan. 2004) 172(1):104-113.

Foster et al., "Human CD62L-memory T cells are less responsive to alloantigen stimulation than CD62L+ naive T cells: potential for adoptive immunotherapy and allodepletion," Blood (2004) 104(8):2403-09.

Foulds et al., "Cutting edge: CD4 and CD8 T cells are intrinsically different in their proliferative responses," J Immunol. (2002) 168(4):1528-1532.

Fraietta et al., "Biomarkers of Response to Anti-CD19 Chimeric Antigen Receptor (CAR) T-Cell Therapy in Patients with Chronic Lymphocytic Leukemia," Blood (Dec. 2016) 128(22):57.

Fransen et al., "The Disease Activity Score and the EULAR response criteria," Clin Exp Rheumatol. (2005) 23(5 Suppl 39):S93-S99.

Frayer et al., "Mean Body Weight, Height, Waist Circumference, and Body Mass Index Among Adults: United States, 1999-2000 Through 2015-2016," Natl Health Stat Report. (2018) (122):1-16.

Frecha et al., "Advances in the field of lentivector-based transduction of T and B lymphocytes for gene therapy," Molecular Therapy: The Journal of the American Society of Gene Therapy (2010) 18:1748-1757.

Freedman et al., "Normal cellular counterparts of B cell chronic lymphocytic leukemia," Blood. (1987) 70:418-427.

Gardner et al., "T cell Products of Defined CD4:CD8 Composition and Prescribed Levels of CD19CAR/Egfrt Transgene Expression Mediate Regression of Acute Lymphoblastic Leukemia in the Setting of Post-Allohsct Relapse," Abstract for Presentation, 56th American Society of Hematology Annual Meeting and Exposition, San Francisco, CA (Dec. 6-9, 2014), Blood (2014) 124:3711.

Gargett et al., "Different cytokine and stimulation conditions influence the expansion and immune phenotype of third-generation

(56) References Cited

OTHER PUBLICATIONS chimeric antigen receptor T cells specific for tumor antigen GD2," Cythotherapy (2015) 17(4):487-495.

Gattinoni and Restifo, "Moving T memory stem cells to the clinic," Blood (2013) 121(4):567-8.

Gattinoni L et al., "Acquisition of full effector function in vitro paradoxically impairs the in vivo antitumor efficacy of adoptively transferred CDS+ T cells," J Clin Invest. (2005) 115(6):1616-26.

Gladman et al., "Systemic Lupus Erythematosus Disease Activity Index 2000," J Rheumatol (2002) 29:288-291.

Godin et al., "Microfluidics and photonics for Bio-System-on-a-Chip: a review of advancements in technology towards a microfluidic flow cytometry chip," J Biophoton. (2008) 1(5):355-376.

González et al., "Ethnicity in systemic lupus erythematosus (SLE): its influence on susceptibility and outcomes," Lupus (Oct. 2013), vol. 22(12), p. 1214-1224.

Granit et al., "Safety and clinical activity of autologous RNA chimeric antigen receptor T-cell therapy in myasthenia gravis (MG-001): a prospective, multicentre, open-label, non-randomised phase 1b/2a study," Lancet Neurol (Jul. 2023) 22(7):578-590, 22 pages.

Gratwohl et al., "Stem cell transplantation for autoimmune diseases," Best Practice & Research Clinical Haematology (2001) 14(4):755-776.

Grossman et al., "Concomitant regulation of T-cell activation and homeostasis," Nat Rev Immunol (2004) 4(5):387-395.

Grupp et al., "T Cells Engineered with a Chimeric Antigen Receptor (CAR) Targeting CD19 (CTL019) Have Long Term Persistence and Induce Durable Remissions in Children with Relapsed, Refractory All," Blood (2014) 124 (21): 380.

Grupp et al., "Chimeric Antigen Receptor-Modified T Cells for Acute Lymphoid Leukemia," N Engl J Med (2013) 368:1509-1518.

Gunzer et al., "Two-step negative enrichment of CD4+ and CD8+ T cells from murine spleen via nylon wool adherence and an optimized antibody cocktail," J Immunol Methods. (2001) 258(1-2): 55-63.

Hacein-Bey-Abina et al., "LMO2-associated clonal T cell proliferation in two patients after gene therpay for SCID-X1," Science (2003) 302(5644); 415-419.

Hackett et al., "A transposon and transposase system for human application," Molecular Therapy: The Journal of the American Society of Gene Therapy (2010) 18:674-683.

Harris-Love et al., "Distribution and severity of weakness among patients with polymyositis, dermatomyositis and juvenile dermatomyositis," Rheumatology (Oxford) (2009) 48(2):134-139.

Hay et al., "The Bilag index: a reliable and valid instrument for measuring clinical disease activity in systemic lupus erythematosus," QJM: An International Journal of Medicine (1993) 86(7):447-458.

Herbst et al., "B-cell depletion in vitro and in vivo with an afucosylated anti-CD19 antibody," J Pharmacol Exp Ther. (2010) 335(1):213-22.

Hermans et al., "The Vital assay: a versatile fluorometric technique for assessing CTL- and NKT-mediated cytotoxicity against multiple targets in vitro and in vivo," J. Immunological Methods (2004) 285(1): 25-40.

Hinchcliff et al., "J. Systemic sclerosis/scleroderma: a treatable multisystem disease," American family physician. (2008) 78(8):961-8.

Hinrichs et al., "Human effector CD8+ T cells derived from naïve rather than memory subsets possess superior traits for adoptive immunotherapy," Blood (2011) 117(3): 808-814.

Hinrichs et al., "Adoptively transferred effector cells derived from naive rather than central memory CD8+ T cells mediate superior antitumor immunity," Proc Natl Acad Sci U S A. (2009) 106(41):17469-74.

Hirakawa et al., "IL-2, IL-7, IL-15 and IL-6 Induce Differential Activation of Naive and Memory T Cell Subsets," Blood (Dec. 2015) 126(23):3425, 4 pages.

Hoffman, et al., "Differential modulation of CD4 and CD8 T-cell proliferation by induction of nitric oxide synthesis in antigen presenting cells," Transplantation. (2002) 74(6): 836-845.

Hou et al., Tutorial on Animal Cell Culture Techniques, Gansu Science and Technology Press, Sep. 2009: p. 105 (Article in Chinese; English translation provided).

Huang et al., "DNA transposons for modification of human primary T lymphocytes," Methods Mol Biol (2009) 506: 115-126.

Huarte et al., "Ex vivo expansion of tumor specific lymphocytes with IL-15 and IL-21 for adoptive immunotherapy in melanoma," Cancer Lett. (2009) 285(1): 80-88.

Hudecek et al., "Direct tumour recognition and helper function of CD4+ T cells modified to express a CD19-specific CAR in vitro and in a preclinical lymphoma model," Abstract for Presentation, 39th Annual Meeting of the European Group for Blood and Marrow Transplantation, London, UK (Apr. 10, 2013), 1 page.

Hudson et al., "Engineered Antibodies," Nature Medicine (2003) 9(1):129-134.

Hunziker et al., "Exhaustion of cytotoxic T cells during adoptive immunotherapy of virus carrier mice can be prevented by B cells or CD4+ T cells," Eur J Immunol (2002) 32(2):374-382.

Illei et al., "Long-term effects of combination treatment with fludarabine and low-dose pulse cyclophosphamide in patients with lupus nephritis." (2007): 952-956.

ICell Gene Therapeutics, "Our Pipeline; iCell Gene Therapeutics researches and develops Chimeric Antigen Receptor (CAR) engineered cell therapies for autoimmune diseases and cancer," Retrieved Jul. 26, 2024; From: https://www.icellgene.com/our-pipeline.

Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese) English translation provided.

Isenberg et al., "Bilag 2004. Development and initial validation of an updated version of the British Isles Lupus Assessment Group's disease activity index for patients with systemic lupus erythematosus," Rheumatology (Oxford). (2005) 44(7):902-6.

Jackson et al., "Evaluation of CD62L expression as a marker for vaccine-elicited memory cytotoxic T lymphocytes," Immunology (2005) 116, 443-53.

Jackson et al., "Levels of L-Selectin (CD62L) on Human Leukocytes in Disseminated Cryptococcosis With and Without Associated HIV-1 Infection," J. Inf. Diseases (2005) 191:1361-7.

Janas et al., "Perfusion's role in maintenance of high-density T-cell cultures," BioProcesses International. (2015) pp. 1-12.

Jethwa et al., "Use of gene-modified regulatory T-cells to control autoimmune and alloimmune pathology: is now the right time?," Clin Immunol. (2014) 150(1):51-63.

Jiang Bo, Fundamentals and Clinics of Apoptosis, People's Military Medical Press, p. 141, Jul. 1999 (Reference in Chinese; English translation provided).

Johnston, et al., "Biolistic transformation: microbes to mice," Nature (1990) 346: 776-777.

Kaartinen et al., "Low interleukin-2 concentration favors generation of early memory T cells over effector phenotypes during chimeric antigen receptor T-cell expansion," Cytotherapy. (Jun. 2017) 19(6):689-702.

Kahn et al., "Optimization of retroviral vector-mediated gene transfer into endothelial cells in vitro," Circ Res. (1992) 71(6): 1508-17.

Kamburova et al., "A Single Dose of Rituximab Does Not Deplete B Cells in Secondary Lymphoid Organs but Alters Phenotype and Function," American Journal of Transplantation (2013) 13:1503-1511.

Kansal et al., "Sustained B cell depletion by CD19-targeted CAR T cells is a highly effective treatment for murine lupus," Sci Transl Med. (2019) 11(482):eaav1648, 13 pages.

Kansas et al., "Transmembrane signals generated through MHC class II, CD19, CD20, CD39, and CD40 antigens induce LFA-1-dependent and independent adhesion in human B cells through a tyrosine kinase-dependent pathway," J Immunol. (1991) 147(12):4094-102.

Katz et al., "Therapeutic targeting of CD19 in hematological malignancies: past, present, future and beyond." Leuk Lymphoma. (2014) 55(5):999-1006.

(56) References Cited

OTHER PUBLICATIONS

Kemper et al., "Label-free quantitative cell division monitoring of endothelial cells by digital holographic microscopy," J Biomed Opt. (May 2010) 15(3):036009, 6 pages.

Kiryluk et al., "Geographic Differences in Genetic Susceptibility to IgA Nephropathy: GWAS Replication Study and Geospatial Risk Analysis," PLOS Genetics (2012) 8(6):e1002765.

Klaver et al., "T Cell Maturation Stage Prior to and During GMP Processing Informs on CAR T Cell Expansion in Patients," Front Immunol. (Dec. 2016) 7:648.

Klebanoff et al., "Sorting through subsets: which T-cell populations mediate highly effective adoptive immunotherapy?," J Immunother. (2012) 35(9): 651-660.

Klebanoff et al., "Sinks, suppressors and antigen presenters: how lymphodepletion enhances T cell-mediated tumor immunotherapy," Trends Immunol. (2005) 26(2):111-7.

Klebanoff et al., "Central memory self/tumor-reactive CD8+ T cells confer superior antitumor immunity compared with effector memory T cells," Proc Natl Acad Sci U S A. (2005); 102(27): 9571-6.

Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," J Clin Oncol (2015) 33(6):540-549.

Kochenderfer et al., "Construction and preclinical evaluation of an anti-CD19 chimeric antigen receptor," J. Immunotherapy (2009) 32(7): 689-702.

Kochenderfer et al., "Adoptive transfer of syngeneic T cells transduced with a chimeric antigen receptor that recognizes murine CD19 can eradicate lymphoma and normal B cells", Blood (2010) 116(19):3875-3886.

Kochenderfer et al., "B-cell depletion and remissions of malignancy along with cytokine-associated toxicity in a clinical trial of anti-CD19 chimeric-antigen-receptor-transduced T cells," Blood (2012) 119(12):2709-2720.

Kohanski, R.A., Lane, M.D. "Monovalent avidin affinity columns" Methods Enzymol. 1990;184:194-200.

Komatsu et al., "Long-Term Survival of Patients with IgA Nephropathy After Dialysis Therapy," Kidney Blood Press Res (2013) 37:649-656.

Koste et al., "T-cell receptor transfer into human T cells with ecotropic retroviral vectors," Gene Therapy (2014) 21: 533-538.

Kranick et al., Aphasia as a complication of CD19-targeted chimeric antigen receptor immunotherapy (S52.006). Neurology. (2014) 82 Suppl 10:S52.006.

Kroot et al., "No increased mortality in patients with rheumatoid arthritis: up to 10 years of follow up from disease onset," Ann Rheum Dis (2000) 59(12):954-958.

Krug et al., "A GMP-compliant protocol to expand and transfect cancer patient T cells with mRNA encoding a tumor-specific chimeric antigen receptor," Cancer Immunol Immunother (2014) 63(10):999-1008.

Kubben et al., "Identification of differential protein interactors of lamin A and progerin," Nucleus (2010) 1(6):513-525.

Kumar et al., "Affinity binding of cells to cryogel adsorbents with immobilized specific ligands: effect of ligand coupling and matrix architecture," J Mol Recog (2005) 18(1):84-93.

Kumar et al., "Cell separation using cryogel-based affinity chromatography," Nature Protocols (2010) 5(11):1737-1747.

Lada et al., "Quantitation of integrated HIV provirus by pulsed-field gel electrophoresis and droplet digital PCR," J Clin Microbiol (2018) 56(12):e01158.

Lardo et al., "Contrast-enhanced multidetector computed tomography viability imaging after myocardial infarction: characterization of myocyte death, microvascular obstruction, and chronic scar," Circulation (2006) 113(3):394-404.

Larvor et al., "Measurement of the dissociation rate constant of antigen/antibody complexes in solution by enzyme-linked immunosorbent assay," J Immuno Methods (1994) 170(2):167-175.

Lee et al., "Current concepts in the diagnosis and management of cytokine release syndrome," Blood. (2014) 124(2):188-95.

Levey et al., "A New Equation to Estimate Glomerular Filtration Rate," Ann Intern Med (2009) 150(9):604-612.

Levin et al., "Optimizing the affinity and specificity of proteins with molecular display," Mol BioSyst (2006) 2:49-57.

Levine et al., "Global manufacturing of CAR T cell therapy" Mol. Ther. Methods & Clin. Dev. (Dec. 2016) 4: 92-101.

Li et al., "Comparison of anti-CD3 and anti-CD28-coated beads with soluble anti-CD3 for expanding human T cells: Differing impact on CD8 T cell phenotype and responsiveness to restimulation," J Transl Med. (2010) 8: 104.

Li et al., "Comparison of inlet geomery in microfluidic cell affinity chromatography," Analytical chemistry (2011) 83(3):774-781.

Li et al., "Directed evolution of human T-cell receptors with picomolar affinities by phage display," Nat Biotechnol. (2005) 23:349-354.

Li et al., "Negative enrichment of target cells by microfluidic affinity chromatography," Analytical Chemistry (2011) 83(20):7863-7869.

Li et al., "Multiparameter cell affinity chromatography: Separation and analysis in a single microfluidic channel," Anal Chem (20+ A40312) 84(19):8140-8148.

Li et al. Identification of the earliest B lineage stage in mouse bone marrow, Immunity (1996) 5(6):527-535.

Li et al., "The regulated expression of B lineage associated genes during B ell differentiation in bone marrow and fetal liver," J Exp Med (1993) 178(3):951-960.

Li et al., "Murine leukemia induced by retroviral gene marking," Science (2002) 296(5567):497.

Life Technologies Corporation (2013) OpTmizer™ CTS™ T-cell Expansion SFM Technical information; pp. 1-2 (Year: 2013).

Ling et al., "B-cell and plasma cell antigens: new and previously defined clusters," Leucocyte typing III. (1987) 302-355.

Liu et al., "Bayesian Optimal Interval Designs for Phase I Clinical Trials," Journal of the Royal Statistical Society: Series C (2015), vol. 64, p. 507-523.

Lu et al., "A Rapid Cell Expansion Process for Production of Engineered Autologous CAR-T Cell Therapies," Human Gene Therapy Methods (Dec. 2016) 27(6):209-218.

Lupton et al., "Dominant positive and negative selection using a hygromycin phosphotransferase-thymidine kinase fusion gene," Mol. and Cell Biol. (1991) 11:6: 3374-3378.

Mackensen et al., "Anti-CD19 CAR T cell therapy for refractory systemic lupus erythematosus," Nat Med (2022) 28(10):2124-2132 and Supplementary Materials.

Mak et al., "Glutathione Primes T Cell Metabolism for Inflammation," Immunity (Apr. 2017) 46(4):675-689.

Mak et al., "Glutathione Primes T Cell Metabolism for Inflammation," Immunity (Apr. 2017) 46(6):1089-1090.

Maldonado et al., "Decreased effector memory CD45RA+ CD62L− CD8+ T cells and increased central memory CD45RA− CD62L+ CD8+ T cells in peripheral blood of rheumatoid arthritis patients," Arthritis Res Ther. (2003) 5(2): R91-R96.

Manuri et al., "piggyBac transposon/transposase system to generate CD19-specific T cells for the treatment of B-lineage malignancies," Hum Gene Ther (2010) 21(4): 427-437.

Marenghi et al., "The role of perfusion in maintaining high density T-cell cultures," GE (Apr. 2014):1-2.

Marmont et al., "Autologous marrow stem cell transplantation for severe systemic lupus erythematosus of long duration," Lupus (1997) 6:545-548.

Marmont et al., "Coincidental autoimmune disease in patients transplanted for conventional indications," Best Practice & Research Clinical Haematology (2004) 17(2):223-232.

Marthandan et al., "An investigation of the effects of the antioxidants, ebselen or N-acetyl cysteine on human peripheral blood mononuclear cells and T cells," Immun Ageing. (Feb. 2013) 10(1):7, 16 pages.

Maude et al., "Chimeric Antigen Receptor T Cells for Sustained Remissions in Leukemia," N Engl J Med. (2014) 371(16):1507-1517.

McGarrity et al., "Patient monitoring and follow-up in lentiviral clinical trials," J Gene Medicine (2013) 15: 78-82.

(56) References Cited

OTHER PUBLICATIONS

Medeiros-Silva et al., "CD4 and CD8 T cells participate in the immune memory response against Vaccinia virus after a previous natural infection," Results in Immunology (2013) 3:104-13.

Medvec et al., "Improved Expansion and In Vivo Function of Patient T Cells by a Serum-free Medium," Mol Ther Methods Clin Dev (Nov. 2017) 8:65-74.

Mei et al., "Rationale of anti-CD19 immunotherapy: an option to target autoreactive plasma cells in autoimmunity," Arthritis Res Ther. (2012) 14 Suppl 5(Suppl 5):S1.

Menon et al., "Balanced synaptic impact via distance-dependent synapse distribution and complementary expression of AMPARs and NMDARs in hippocampal dendrites," Neuron (2013) 80(6):1451-1463.

Menon et al., "Characterising aggressive multiple sclerosis," Journal of Neurology, Neurosurgery & Psychiatry. (2013) 84(11):1192-8.

Merrill et al., "Efficacy and Safety of Rituximab in Moderately-to-Severely Active Systemic Lupus Erythematosus:" Arthritis Rheum (2010) 62(1):222-233.

Miller et al., "Improved retroviral vectors for gene transfer and expression," BioTechniques (1989) 7:980-990.

Miller et al., "Retrovirus packaging cells," Human Gene Therapy (1990) 1:5-14.

Milone et al., "Chimeric Receptors Containing CD137 Signal Transduction Domains Mediate Enhanced Survival of T Cells and Increased Antileukemic Efficacy In Vivo," Mol Ther (2009) 17(8):1453-64.

Miltenyi et al., "High Gradient Magnetic Cell Seperation With MACs", Cytometry (1990) 11(11):231-238.

Modlich et al., "Leukemias following retroviral transfer of multidrug resistance 1 (MDR1) are driven by ombinatorial insertional mutagenesis," Blood (2005) 105(11): 4235-4246.

Moeller et al., "Adoptive transfer of gene-engineered CD4+ helper T cells induces potent primary and secondary tumor rejection," Blood (2005) 106(9):2995-3003.

Mohammad et al., "Incidence and survival rates in Wegener's granulomatosis, microscopic polyangiitis, Churg-Strauss syndrome and polyarteritis nodosa," Rheumatology (Oxford) (2009) 48(12):1560-1565.

Mougiakakos et al., "CD19-Targeted CAR T Cells in Refractory Systemic Lupus Erythematosus," N Engl J Med (2021) 385(6):567-569 and Supplementary Appendix.

Muhonen, et al., "Decreasing CD4/CD8 ratio during prolonged four-drug chemotherapy plus interferon treatment for metastatic melanoma," J Immunother Emphasis Tumor Immunol. (1994) 15(1): 67-73.

Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.

Müller et al., "CD19-targeted CAR T cells in refractory antisynthetase syndrome," The Lancet (Mar. 11, 2023) 401(10379):815-818.

Nadler et al., "B4, a human B lymphocyte-associated antigen expressed on normal, mitogen-activated, and malignant B lymphocytes," J Immunol. (1983) 131(1):244-50.

Nagy et al., "Stability of cytotoxic luteinizing hormone-releasing hormone conjugate (AN-152) containing doxorubicin 14-O-hemiglutarate in mouse and human serum in vitro: Implications for the desig+A333n of preclinical studies," PNAS (2000) 97(2):829-834.

Nascimbeni et al., "Peripheral CD4+CD8+ T cells are differentiated effector memory cells with antiviral functions," Blood (2004) 104(2):478-86.

Navarra et al., "Efficacy and safety of belimumab in patients with active systemic lupus erythematosus: a randomised, placebo-controlled, phase 3 trial," Lancet (2011) 377(9767) p. 721-731.

Navarro et al., "Estrogen Stimulation Differentially Impacts Human Male and Female Antigen-specific T cell Anti-Tumor Function and Polyfunctionality," Gender and the Genome (Dec. 2017) 1(4); 167-179.

Neeson et al., "Ex vivo culture of chimeric antigen receptor T cells generates functional CD8+ T cells with effector and central memory-like phenotype," Gene Therapy (2010) 17(9):1105-1116.

Neller et al., "Tracking the repertoire of human adult and neonatal T cells during ex vivo amplification," Br J Haematol. (2012) 159(3):370-373.

Nickerson et al., "TLR9 Regulates TLR7- and MyD88-Dependent Autoantibody Production and Disease in a Murine Model of Lupus," J Immunol (2010) 184(4):1840-1848.

Nunez et al., "Cytokine and reactivity profiles in SLE patients following anti-CD19 CART therapy," Mol Ther Methods Clin Dev (Dec. 2023) 31:101104, 6 pages.

Oddis et al., "Rituximab in the Treatment of Refractory Adult and Juvenile Dermatomyositis and Adult Polymyositis: A Randomized, Placebo-phase Trial," Arthritis & Rheumatism, vol. 65(2), p. 314-324.

Okamoto et al., "A promising vector for TCR gene therapy: differential effect of siRNA, 2A peptide, and disulfide bond on the introduced TCR expression," Mol Ther Nucl Acids (2012) 1(12):1-11.

Okern et al., "CTS™ immune cell SR for serum free culture and expansion of human T cells," Journal for Immuno Therapy of Cancer (2015) 3(suppl 2): P1.

Okon et al., "Cutaneous Lupus Erythematosus: Diagnosis and treatment," Best Pract Res Clin Rheumatol (2013) 27(3):391-404.

Padlan et al., "X-ray crystallography of antibodies," Adv Prot Chem (1996) 49:57-133.

Padmanabhan et al., "Purification of transiently transfected cells by magnetic-affinity cell sorting," J Immunogenetics (1989) 16(2):91-102.

Park et al., "KYV-101, a Fully Human Anti-CD19 CAR T Cell Therapy, Demonstrates CAR-Mediated and CD19-Dependent Activity Against Autologous B Cells from Patients with Autoimmune Disease," American College of Rheumatology, Meeting: ACR Convergence 2023, Session date: Monday, Nov. 13, 2023, Abstract No. 0904, 2 pages, retrieved from: https://acrabstracts.org/abstract/kyv-101-a-fully-human-anti-cd19-car-t-cell-therapy-demonstrates-car-mediated-and-cd19-dependent-activity-against-autologous-b-cells-from-patients-with-autoimmune-disease/.

Park et al., "Treating cancer with genetically engineered T cells," Trends Biotechnol. (2011) 29(11): 550-557.

Parkhurst et al., "Characterization of genetically modified T-cell receptors that recognize the CEA:691-699 peptide in the context of HLA-A2.1 on human colorectal cancer cells," Clin Cancer Res. (2009) 15:169-180.

Pecher et al., "CD19-Targeting CAR T Cells for Myositis and Interstitial Lung Disease Associated With Antisynthetase Syndrome," JAMA (Jun. 2023) 329(24):2154-2162.

Pezzutto et al., "CD19 monoclonal antibody HD37 inhibits anti-immunoglobulin-induced B cell activation and proliferation," J Immunol. (1987) 138(9):2793-9.

Pillemer et al., "Sjögrens Syndrome," Encyclopedia of Gastroenterology (2004) p. 384-389.

Pinthus et al., "Adoptive immunotherapy of prostate cancer bone lesions using redirected effector lymphocytes," J Clin Invest (2004) 114(12):1774-1781.

Plieva et al., "Characterization of supermacroporous monolithic polyacrylamide based matrices designed for chromatography of bioparticles," Journal of Chromatography (2004) 807(1):129-137.

Poltorak et al., "Expamers: a new technology to control T cell activation," Scientific Reports (Oct. 2020) 10(1):17832, 15 pages.

Porter et al., "A phase 1 trial of donor lymphocyte infusions expanded and activated ex vivo via CD3/CD28 costimulation," Blood. (2006) 107(4): 1325-1331.

Porter et al., "Chimeric Antigen Receptor-Modified T Cells in Chronic Lymphoid Leukemia," N Engl J Med (2011) 365(8):725-733.

(56) References Cited

OTHER PUBLICATIONS

Prevoo et al., "Modified disease activity scores that include twenty-eight-joint counts. Development and validation in a prospective longitudinal study of patients with rheumatoid arthritis," Arthritis Rheum. (1995) 38(1):44-8.
Pullagurla et al., "Parallel affinity-based isolation of leukocyte subsets using microfluidics: application for stroke diagnosis," Analytical chemistry (2014) 86(8):4058-4065.
Purification Technical Handbook, Thermo Scientific Pierce Protein, 84 pages. (2010 retrieved from https://at.vwr.com/assetsvc/asset/de_AT/id/20551553/contents).
Qiagen et al., Strep-tagged Protein Purification Handbook for expressing, purifying, and detecting proteins carrying a Strep-tag II or a 6xHis tag and a strep-tag II Two-step protein purification system His. Strep pQE-TriSystem Vector Set pQE-TriSystem Strep Vector Strep-Tactin Superflow and Superflow Cartridge (2007).
Qian et al., "Advances in the Development of Interleukin-2 and its Analogues," Chinese Journal of Pharmaceuticals (Mar. 2020) p. 947-955. (Article in Chinese; English abstract provided).
Qin et al., "Epidemiology of primary Sjögren's syndrome: a systematic review and meta-analysis," Ann Rheum Dis (2015) 74(11):1983-1989.
Rabenstein et al., "Differential kinetics of antigen dependency of CD4+ and CD8+ T cells," J Immunol. (2014) 192(8):3507-17.
Ramos-Casals et al., "Cryoglobulinemia in primary Sjögren's syndrome: Prevalence and clinical characteristics in a series of 115 patients," Seminars in Arthritis and Rheumatism (1998) 28(3):200-205.
Ramos-Casals et al., Adult haemophagocytic syndrome. Lancet. Apr. 26, 2014;383(9927):1503-1516. Erratum in: Lancet. Apr. 26, 2014;383(9927):1464.
Rich et al., "A global benchmark study using affinity-based biosensors," Analytical Biochemistry (2009) 386:194-216.
Riddell et al., "Adoptive Therapy with Chimeric Antigen Receptor Modified T Cells of Defined Subset Composition," cancer J. (2014) 20(2): 141-44.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Rider et al., "Validation of manual muscle testing and a subset of eight muscles for adult and juvenile idiopathic inflammatory myopathies." Arthritis care & research 62.4 (2010): 465-472.
RoActemra®0 [Summary of Product Characteristics]. Welwyn Garden City, United Kingdom: Roche Products Limited. Available from: URL: http://www.ema.europa.eu/docs/en_GB/document_library/EPAR_-Product_Information/human/000955/WC500054890.pdf.
Rosario et al., "Is there a cure for systemic lupus erythematosus?" Lupus (2013) 22:417-421.
Rosenberg, et al., "Cell transfer immunotherapy for metastatic solid cancer—what clinicians need to know," Nat Rev Clin Oncol. (2011) 8(10):577-85.
Rosenberg, et al., "Use of tumor-infiltrating lymphocytes and interleukin-2 in the immunotherapy of patients with metastatic melanoma. A preliminary report," N Engl J Med. (1988) 319:1676-1680.
Rothe et al., "Biosafety challenges for use of lentiviral vectors in gene therapy," Current Gene Ther (2013) 13(6): 453-468.
Rybak, J.N., et al. "Purification of biotinylated proteins on streptavidin resin: a protocol for quantitative elution," Proteomics. 2004 4(8): 2296-2299.
Sadelain et al., "The basic principles of chimeric antigen receptor design," Cancer Discov. (2013) 3(4): 388-398.
Saligrama et al., "IL-15 maintains T-cell survival via S-nitrosylation-mediated inhibition of caspase-3," Cell Death Differ. (2014) 21(6):904-14.
Sallusto et al., "Two subsets of memory T lymphocytes with distinct homing potentials and effector functions," Nature (1999) 401:708-712.
Salmon, "Arming T cells against B cells in systemic lupus erythematosus," Nat Med (2022) 28(10):2009-2010.
Scarpa et al., "Characterization of recombinant helper retroviruses from Moloney-based vectors in ecotropic and amphotropic packaging cell lines," Virology (1991) 180:849-852.
Schlub et al., "Predicting CD62L expression during the CD8+ T cell response in vivo," Immunol Cell Biol. (2010) 88(2): 157-64.
Schmidt and Skerra, The Strep-tag system for one-step purification and high-affinity detection or capturing of proteins. Nat Protoc. 2007;2(6):1528-1535.
Schmitt et al., "Adoptive transfer and selective reconstitution of streptamer-selected cytomegalovirus-specific CDS+ T-cells leads to virus clearance in patients after allogeneic peripheral blood stem cell transplantation", Transfusion, vol. 51, No. 3, Dec. 6, 2010 (Dec. 6, 2010), pp. 591-599.
Scholler et al., "Decade-long safety and function of retroviral-modified chimeric antigen receptor T cells," Sci Transl Med (2012) 4(132): 132ra153.
Schriever et al., "Isolated human follicular dendritic cells display a unique antigenic phenotype," J Exp Med. (1989) 169(6):2043-58.
Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012]—p. 34-p. 37 (English translation provided).
Sharma et al., "Efficient sleeping beauty DNA transposition from DNA minicircles," Molec Ther Nucl Acids (2013) 2, e74, 10 pages.
Shiiki et al., "Prognosis and risk factors for idiopathic membranous nephropathy with nephrotic syndrome in Japan," Kidney International (2004) 65:1400-1407.
Skea et al., "The selective expansion of functional T cell subsets," J Hematother Stem Cell Res. (1999) 8(5): 525-38.
Smith et al., "Ex vivo expansion of human T cells for adoptive immunotherapy using the novel Xeno-free CTS Immune Cell Serum Replacement," Clinical & Translational Immunology (2015) 4:e31, 10 pages.
Smith et al., "Rituximab in diffuse cutaneous systemic sclerosis: an open-label clinical and histopathological study," Annals of the Rheumatic Diseases (2008), vol. 69(01), p. 193-197.
Smolen et al., "A simplified disease activity index for rheumatoid arthritis for use in clinical practice," Rheumatology (Oxford) (2003) 42(2):244-57.
Stachel et al., "Enhanced lymphocyte proliferation responses in pediatric patients early after myelosuppressive chemotherapy," Pediatr Blood Cancer (2004) 43(6):644-650.
Stamenkovic and Seed, "CD19, the earliest differentation antigen of the B cell lineage, bears three extracellular immunoglobulin-like domains and an Epstein-Barr virus-related cytoplasmic tail," J Exp Med (1988) 168(3): 1205-1210.
Stemberger et al., "Novel Serial Positive Enrichment Technology Enables Clinical Multiparameter Cell Sorting," PLoS One (2012) 7(4): e35798, 11 pages.
Sullivan et al., "Myeloablative Autologous Stem-Cell Transplantation for Severe Scleroderma," N Engl J Med. (Jan. 2018) 378(1):35-47.
Sun et al., "Early transduction produces highly functional chimeric antigen receptor-modified virus-specific T-cells with central memory markers: a Production Assistant for Cell Therapy (PACT) translational application," J Immunother Cancer. (2015) 3:5.
Szoka et al., "Comparative properties and methods of preparation of lipid vesicles (liposomes)," Ann. Rev. Biophys. Bioeng. (1980) 9: 467.
Taubmann et al., "Tolerability of CAR T Cell Therapy in Autoimmune Disease," American College of Rheumatology, Meeting: ACR Convergence 2023, Session date: Sunday, Nov. 12, 2023, Abstract No. 0783, 2 pages, retrived from: https://acrabstracts.org/abstract/tolerability-of-car-t-cell-therapy-in-autoimmune-disease/.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.

(56) References Cited

OTHER PUBLICATIONS

Thurlings et al., "Synovial tissue response to rituximab: mechanism of action and identification of biomarkers of response," Ann Rheum Dis (2008) 67(7):917-925.
Till et al., "CD20-specific adoptive immunotherapy for lymphoma using a chimeric antigen receptor with both CD28 and 4-1BB domains: pilot clinical trial results," Blood (2012) 119(17): 3940-3950.
Touma et al., "SLEDAI-2K Responder Index 50 captures 50% improvement in disease activity over 10 years," Lupus. (2012) 21(12):1305-11.
Trager et al., "Mortality and causes of death in systemic lupus erythematosus," Curr Opin Rheu (2001) 12:345-351.
Tsukahara et al., "CD19 target-engineered T-cells accumulate at tumor lesions in human B-cell lymphoma xenograft mouse models," Biochem Biophys Res Commun (2013) 438(1): 84-89.
Turk et al., ". Concomitant tumor immunity to a poorly immunogenic melanoma is prevented by regulatory T cells," J Exp Med (2004) 200(6):771-782.
Turtle et al., "Anti-CD19 Chimeric Antigen Receptor-Modified T Cell Therapy for B Cell Non-Hodgkin Lyphoma and Chronic Lyphocytic Leukemia: Fludarabine and Cyclophosphamide Lyphodepletion Improves In Vivo Expansion and Persistence of CAR-T Cells and Clinical Outcomes," Blood (2015) 126:184.
Turtle et al., "CD19 CAR-T cells of defined CD4+:CD8+ composition in adult B cell All patients," J. Clin. Invest. (Jun. 2016) 126(6):2123-38.
Turtle et al., "Engineered T cells for anti-cancer therapy," Curr. Opin. Immunol. (2012) 24(5): 633-39.
Turtle et al., "Immunotherapy with CD19-specific chimeric antigen receptor (CAR)-modified T cells of defined subset composition," 2015 ASCO meeting abstract 3006, J. Clin. Oncol. (2015) 33:Suppl. Abstr 3006.
Tyndall et al., "Blood and marrow stem cell transplants in autoimmune disease. A consensus report written on behalf of the European League Against Rheumatism (EULAR) and the European Group for Blood and Marrow Transplantation (EBMT)," Br J Rheumatol (1997) 36(3):390-392.
Tyndall et al., "Haemopoietic stem cell transplantation in the treatment of severe autoimmune diseases 2000," Ann Rheum Dis (2001) 60:702-707.
Uckun et al., "Detailed studies on expression and function of CD19 surface determinant by using B43 monoclonal antibody and the clinical potential of anti-CD19 immunotoxins," Blood. (1988) 71(1):13-29.
Uhlen et al., "Tissue-based map of the human proteome," Science. (2015) 347(6220): 1260419. doi: 10.1126/science. 1260419.
University of Pennsylvania: "Phase I/IIA Study of CART19 Cells for Patients With Chemotherapy Resistant or Refractory CD19+ Leukemia and Lymphoma (Pedi CART19)", ClinicalTrials.gov Identifier:NCT01626495, Retrieved from the Internet: URL:https://clinicaltrials.gov/ct2/show/NCT01626495 [retrieved on Dec. 28, 2016].
University of Michigan: "Classification of Scleroderma," Retrieved Jul. 26, 2024 from https://www.uofmhealth.org/conditions-treatments/rheumatology/classification-scleroderma.
Van den Hoogen et al., Initiative, Against Rheumatism Collaborative. "2013 Classification Criteria for Systemic Sclerosis." Arthritis & Rheumatism 65.11 (2013): 2737-2747.
Van Tendeloo et al., "High-level transgene expression in primary human T lymphocytes and adult bone marrow CD34+ cells via electroporation-mediated gene delivery," Gene Therapy (2000) 7(16): 1431-1437.
Vander Heiden et al., "pRESTO: a toolkit for processing high-throughput sequencing raw reads of lymphocyte receptor repertoires." Bioinformatics 30.13 (2014): 1930-1932.
Varela-Rohena et al., "Control of HIV-1 immune escape by CD8 T cells expressing enhanced T-cell receptor," Nat Med. (2008) 14:1390-1395.
Verhoeyen et al., "Lentiviral vector gene transfer into human T cells," Methods Mol Biol. (2009) 506: 97-114.
Vormittag et al., "A guide to manufacturing CAR T cell therapies," Curr Opin in Biotechnology (2018) 53:164-181.
Wadhwa et al., "Receptor mediated glycotargeting," J. Drug Targeting (1995) 3: 111-127.
Wadhwa et al., "The 2nd International Standard for Interleukin-2 (IL-2). Report of a collaborative study." J Immunol Methods. (2013) 397(1-2):1-7.
Wang X et al: "Generation of leukaemia antigen-specific donor lymphocyte infusions powered by streptamer-based selection", & Bone Marrow Transplantation, vol. 43, No. Suppl. 1, Mar. 2009 (Mar. 2009), p. S73.
Wang et al., "A transgene-encoded cell surface polypeptide for selection, in vivo tracking, and ablation of engineered cells," Blood (2011) 118(5):1255-1263.
Wang et al., "Clinical manufacturing of CAR T cells: foundation of a promising therapy," Molecular Therapy—Oncolytics (Jun. 2016) 3:16015, 7 pages.
Wang et al., "Phenotypic and functional attributes of lentivirus-modified CD19-specific human CD8+ central memory T cells manufactured at clinical scale," J Immunother. (2012) 35(9):689-701.
Wang et al., "Open-tubular capillary cell affinity chromatography: single and tandem blood cell separation," Anal Chem (2008) 80(6):2118-2124.
Wang et al: "Streptamer-based selection of WT1-specific CD8+ T cells for specific donor lymphocyte infusions", Experimental Hematology, vol. 38, No. 11, Nov. 1, 2010 (Nov. 1, 2010), pp. 1066-1073.
Wang et al., "Analysis of lentiviral vector integration in HIV+ study subjects receiving autologous infusions of gene modified CD4+ T cells," Mol Ther (2009) 17(5): 844-850.
Ware et al., "The MOS 36-item short-form health survey (SF-36). I. Conceptual framework and item selection," Med Care. (1992) 30(6):473-83.
Weigmann, "Cell Isolation of Spleen Mononuclear Cells," Bio-Protocol (2013) 3(9):4 pages.
Wells et al., "Validation of the 28-joint Disease Activity Score (DAS28) and European League Against Rheumatism response criteria based on C-reactive protein against disease progression in patients with rheumatoid arthritis, and comparison with the DAS28 based on erythrocyte sedimentation rate," Ann Rheum Dis. (2009) 68(6):954-60.
Wigler et al., "Transfer of purified herpes virus thymidine kinase gene to cultured mouse cells," Cell (1977) 11: 223-232.
Wilson et al., "The use of mRNA display to select high-affinity protein-binding peptides," (Proc.Natl.Acad.Sci.USA 98 (2001) 3750-3755.
Wirth et al., "Differentiation of Central Memory CD8 T Cells Is Independent of CD62L-Mediated Trafficking to Lymph Nodes," J. Immunol. (2009) 182: 6195-6206.
Wise et al., "Belimumab and Rituximab in Systemic Lupus Erythematosus: A Tale of Two B Cell-Targeting Agents," Front Med (Lausanne). (2020) 7:303, 10 pages.
Wrzesinski et al., "Less is more: lymphodepletion followed by hematopoietic stem cell transplant augments adoptive T-cell-based anti-tumor immunotherapy," Curr Opin Immunol. (2005) 17(2):195-201.
Wu et al., "Adoptive T-cell therapy using autologous tumor-infiltrating lymphocytes for metastatic melanoma: current status and future outlook," Cancer (2012) 18(2): 160-175.
Xu et al., "Aptamer-based microfluidic device for enrichment, sorting, and detection of multiple cancer cells", Analytical Chemistry (2009) 81(17):7436-7442.
Xu et al., "Closely related T-memory stem cells correlate with in vivo expansion of CAR.CD19-T cells and are preserved by IL-7 and IL-15," Blood (2014) 123(24):3750-3759.
Xu et al., "Multiparameter comparative analysis reveals differential impacts of various cytokines on CART cell phenotypes and function ex vivo and in vivo," Oncotarget (Dec. 2016) 7(50):82354-82368.
Xu et al., "Cytokine release syndrome in cancer immunotherapy with chimeric antigen receptor engineered T cells," Cancer Letters (2014) 343(2):172-178.

(56) References Cited

OTHER PUBLICATIONS

Yarilin, "Immunology principles," M. Medicine (1999) 184-195, 339-347 (English Translation included).

Yazawa et al., "Immunotherapy using unconjugated CD19 monoclonal antibodies in animal models for B lymphocyte malignancies and autoimmune disease," Proc Natl Acad Sci USA. (2005) 102(42):15178-83.

Yee et al., "Numerical scoring for the Bilag-2004 index," Rheumatology. (2010) 49(9):1665-1669.

Yurkovich et al., "Overall and cause-specific mortality in patients with Systemic Lupus Erythematosus: A Meta-Analysis of observational studies," Arthritis Care & Research (2014) 66(4):608-616.

Zhao et al., "Development of the First World Health Organization Lentiviral Vector Standard: Toward the production control and standardization of lentivirus-based gene therapy products," Human Gene Therapy Methods (Aug. 2017) 28(4):205-214.

U.S. Appl. No. 19/051,032, filed Feb. 11, 2025, by Lee et al.

Celgene, "Understanding CAR T-cell Therapy as a Treatment Option for Blood Cancer Patients," Leukemia & Lymphoma Society (Jun. 21, 2019), Presentation, Hilton Nashville Downtown, Nashville, TN, 177 pages, retrieved from https://m.teamintraining.org/sites/default/files/National/USA/Pdf/Slides_Transcipts/P19065_CAR%20T%20Nashville_Combined%20Decks_FINAL_.pdf.

Sommermeyer et al., "Chimeric antigen receptor-modified T cells derived from defined CD8+ and Cd4+ subsets confer superior antitumor reactivity in vivo," Leukemia (Feb. 2016, e-pub. Sep. 15, 2015) 30(2):492-500.

* cited by examiner

Tubing ———

Tubing ———

METHODS FOR ISOLATING, CULTURING, AND GENETICALLY ENGINEERING IMMUNE CELL POPULATIONS FOR ADOPTIVE THERAPY

CROSS-REFERENCE TO RELATED APPLICATIONS

This application is a continuation of U.S. application Ser. No. 18/166,447, filed Feb. 8, 2023, which is a continuation of U.S. application Ser. No. 17/850,875 filed Jun. 27, 2022, which is a continuation of U.S. application Ser. No. 15/305,337 filed Apr. 3, 2017, now patented as U.S. Pat. No. 11,400,115, which is a U.S. National Stage of International Application No. PCT/US2015/027401 filed Apr. 23, 2015, which claims priority from U.S. provisional application No. 61/983,415, filed Apr. 23, 2014, the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042000203SeqList.xml, created Dec. 16, 2024, which is 32,629 bytes in size. The information in the electronic format of the Sequence Listing is incorporated by reference in its entirety.

FIELD

The present disclosure relates in some aspects to methods, cells, and compositions for preparing cells, and compositions for genetic engineering and cell therapy. Provided in some embodiments are streamlined cell preparation methods, e.g., for isolation, processing, incubation, and genetic engineering of cells and populations of cells. Also provided are cells and compositions produced by the methods and methods of their use. The cells can include immune cells, such as T cells, and generally include a plurality of isolated T cell populations or T cell sub-types. In some aspects, the methods are capable of preparing of a plurality of different cell populations for adoptive therapy using fewer steps and/or resources and/or reduced handling compared with other methods.

BACKGROUND

Various methods are available for preparing cells for therapeutic use. For example, methods are available for isolating, processing, and engineering cells, including T cells and other immune cells. Methods are available to isolate such cells and to express genetically engineered antigen receptors, such as high affinity T cell receptors (TCRs) and chimeric antigen receptors (CARs). Methods are available to adoptively transfer such cells into subjects. Improved methods are needed for the preparation (e.g., isolation, processing, culturing, and engineering) of cells for use in cell therapy. In particular, methods are needed for the preparation and engineering of cells, e.g., a plurality of isolated cell types or sub-types, with improved efficiency, safety, variability, and conservation of resources. Provided are methods, cells, compositions, kits, and systems that meet such needs.

SUMMARY

Provided are methods for the preparation and engineering of cells and populations of cells and cells and compositions produced by the methods. In some embodiments, the cells can be used for immunotherapy, such as in connection with adoptive immunotherapy methods. In some aspects, the provided methods include isolation, selection or enrichment of CD4+ and CD8+ cells, or sub-populations thereof, from the same starting sample, such as a single sample, for example a single apheresis sample, leukapheresis sample or a sample containing peripheral blood mononuclear cells (PBMCs). In some embodiments, the methods include selection or enrichment of at least two populations of cells, such as a CD4+ cell population and a CD8+ population, in a single processing stream in which no negative fraction sample is discarded from a first selection or enrichment of one of the CD4+ or CD8+ in the process, prior to performing the second selection for the other of the CD4+ or CD8+ cells. In some embodiments, the first and second selection can occur simultaneously or sequentially.

In some aspects, the selection, enrichment and/or isolation of both populations of cells, such as CD4+ and CD8+ cells, is performed simultaneously, such as in the same vessel or using the same apparatus, or sequentially as part of a system or apparatus in which vessels, e.g. columns, chambers, used in performing the first and second selection, are operably connected. In some embodiments, the simultaneous and/or sequential enrichments or selections can occur as a single process stream without handling of any of the positive or negative fractions prepared as part of the first and/or second selection or enrichment. In some aspects, the isolation, culture, and/or engineering of the different populations is carried out from the same starting composition or material, such as from the same sample.

In some embodiments, the methods include performing a first selection by enriching from a sample containing primary human T cells one of CD4+ or CD8+ cells to generate a first selected population and a non-selected population, and from the non-selected population performing a second selection by enriching for the other of CD4+ cell or CD8+ cell, wherein the method produces a composition of cells containing cells enriched for CD4+ cells and cells enriched for CD8+.

In some embodiments, the second selection is carried out by enriching for the other of the T cell subtypes from the non-selected population generated by the first selection. Thus, in some embodiments, the provided methods differ from other selection methods in that the negative fraction from a first selection is not discarded but rather is used as the basis for a further selection to enrich for another cell type. In general, where the T cell subset enriched for in the first selection is a CD4+ subset (or where the first selection enriches for CD4+ cells), it will follow that the first selection is designed such that it does not enrich for cells of the other subtype to be enriched for in the second selection. For example, in some embodiments, the first selection enriches for CD4+ cells and does not enrich for CD8+ cells, and the second selection enriches for CD8+ cells from the negative fraction recovered from the first selection. Likewise, in general, where the T cell subset enriched for in the first selection is a CD8+ subset (or where the first selection enriches for CD8+ cells), it will follow that the first selection is designed such that it does not enrich for cells of the other subtype to be enriched for in the second selection. For example, in some embodiments, the first selection enriches for CD8+ cells and does not enrich for CD4+ cells, and the second selection enriches for CD4+ cells from the negative fraction recovered from the first selection.

In some embodiments, the methods further involve third, fourth, and so-forth further selections, which may enrich for cells from the selected and/or the non-selected populations from any previous selection step. For example, in some embodiments, cells from either the selected population or the non-selected population from a given step (e.g., the second selection step, are further enriched. For example, in some embodiments, selected CD8+ cells are further enriched for a subtype of CD8+ cells, such as resting cells or central memory cells.

In some embodiments, provided is a method for producing genetically engineered T cells, comprising (a) providing a culture-initiation composition, said composition produced by performing a first selection in a closed system, said first selection comprising enriching for one of CD4+ cells and CD8+ cells from a sample containing primary human T cells, thereby generating a first selected population and a non-selected population, and performing a second selection in the closed system, said second selection comprising enriching for the other of CD4+ cells and CD8+ cells from the non-selected population, thereby generating a second selected population; (b) incubating a culture-initiating composition, which comprises cells of the first selected population and cells of the second selected population, in a culture vessel under stimulating conditions, thereby generating stimulated cells; and (d) introducing a genetically engineered antigen receptor into stimulated cells generated in (b), wherein the method thereby generates an output composition comprising CD4$^+$ T cells and CD8$^+$ T cells expressing the genetically engineered antigen receptor.

Also provided, in some embodiments, are methods that include a simultaneous enrichment or selection of a first and second population of cells, such as a CD4+ and CD8+ cell population. In some embodiments, the method includes contacting cells of a sample containing primary human T cells with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample, and recovering cells bound to the first and/or the second immunoaffinity reagent, thereby generating an enriched composition comprising CD4+ cells and CD8+ cells. In some embodiment, the methods are performed to include in the incubation composition a concentration of the first and/or second immunoaffinity reagent that is at a sub-optimal yield concentration so that the enriched composition contains less than 70%, less than 60%, less than 50%, less than 40%, less than 30%, less than 20% or less of the total CD4+ cells in the incubation composition or less than 70% less than 60%, less than 50%, less than 40%, less than 30%, less than 20% or less of the CD8+ cells in the incubation composition.

In some embodiments, provided is a method for enriching CD4+ and CD8+ T cells, comprising providing an enriched composition of CD4+ and CD9+ T cells, said enriched composition produced by contacting cells of a sample containing primary human T cells with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample; and recovering cells bound to the first and/or the second immunoaffinity reagent, thereby generating an enriched composition comprising CD4+ cells and CD8+ cells at a culture-initiating ratio, wherein: the first and/or second immunoaffinity reagent are present in the incubation composition at a sub-optimal yield concentration, whereby the enriched composition contains less than 70% of the total CD4+ cells in the incubation composition and/or less than 70% of the CD8+ cells in the incubation composition, thereby producing a composition enriched for CD4+ and CD8+ T cells.

In some embodiments of any of such provided embodiments, the methods are performed by immunoaffinity-based selection, such as by contacting cells with an antibody that specifically binds a cell surface marker, such as CD4, CD8 or other cell surface marker, such as expressed on naïve, resting or central memory T cells. In some embodiments, the solid support is a sphere, such as a bead, such as a microbead or nanobead. In some embodiments, the bead can be a magnetic bead. In some embodiments, the solid support can be a column or other vessel to effect column chromatography.

In some embodiments, the antibody contains one or more binding partners capable of forming a reversible bond with a binding reagent immobilized on the solid surface, such as a sphere or chromatography matrix, wherein the antibody is reversibly mobilized to the solid surface. In some embodiments, cells expressing a cell surface marker bound by the antibody on said solid surface are capable of being recovered from the matrix by disruption of the reversible binding between the binding reagent and binding partner. In some embodiments, the binding reagent is streptavidin or is a streptavidin analog or mutant, such as a streptavidin, analog or mutant set forth in any of SEQ ID NOS:11-16 or a sequence of amino acids that exhibits at least 90%, 91%, 92%, 93%, 94%, 95%, 96%, 97%, 98%, 99% or more sequence identity to the sequence set forth in any of SEQ ID NOS: 11-16 and retains binding to a binding partner, such as biotin or peptide. In some embodiments, the binding partner is biotin, a biotin analog or a peptide capable of binding to the binding reagent. In some embodiments, the binding partner is or contains a peptide capable of binding the binding reagent, such as a streptavidin binding peptide, such as a peptide containing the sequence set forth in any of SEQ ID NOS: 1-10. In some embodiments, the methods include after contacting cells in the sample to the solid support containing the antibody immobilized thereon as part of the first and/or second selection, applying a competition reagent to disrupt the bond between the binding partner and binding reagent, thereby recovering the selected cells from the solid surface. In some embodiments, the competition reagent is biotin or biotin analog.

In some embodiments, the methods generate a selected or enriched composition containing selected or enriched CD4+ cells to CD8+ cells, or sub-populations thereof, present at a culture-initiating ratio. In some embodiments, the culture-initiating ratio of CD4+ to CD8+ cells is between at or about 10:1 and at or about 1:10, between at or about 5:1 and at or about 1:5 or is between at or about 2:1 and at or about 1:2, such as is at or about 1:1. It is within the level of a skilled artisan to choose or select a sufficient amount or a sufficient relative amount of immunoaffinity-based reagent, such as antibody-coated beads (e.g. magnetic beads) or an affinity chromatography matrix or matrices, to achieve or produce a culture-initiating ratio in the generated composition, such as culture-initiation composition, containing cells enriched or selected for CD4, CD8 or sub-populations thereof. Exemplary of such methods are described in subsections below.

In some embodiments, the cells include cells of the immune system, such as lymphocytes, e.g., T cells (e.g., CD4+ and CD8+ T cells and isolated subpopulations thereof), and NK cells. In some embodiments, the cells are present in combinations of multiple cell populations or cell types, which in some aspects are included in the compositions at particular ratios or numbers of the cells or cell types. Also provided are methods for optimizing the methods, such as by selecting or determining appropriate ratios and numbers, such as culture-initiating ratios and desired output ratios and doses, of the cell types and population, for use in connection with the methods.

Also provided are cells, cell populations, and compositions thereof, for use in and produced by the methods. Also provided are systems, devices, apparatuses, reagents, compounds, and kits for carrying out the methods. Also provided are therapeutic methods and uses for cells and compositions produced by the methods, such as methods for adoptive cell therapy.

In some embodiments, provided are methods for producing cells for adoptive cell therapy, methods for producing cells for genetic engineering, and methods for producing genetically engineered cells. In some aspects, the cells are T cells, such as CD4+ and CD8+ T cells and/or sub-types thereof. In some aspects, the cell therapy is T cell therapy.

In some embodiments, the methods are carried out by (a) isolating cell populations from a sample, and (b) incubating a culture-initiating composition in a culture vessel containing cells of the isolated populations. In some aspects, the methods further include genetically engineering the incubated cells or cells in the culture vessel, such as by (c) introducing a genetically engineered antigen receptor into cells in the culture vessel.

In some embodiments, the methods are carried out by (a) incubating a culture-initiating composition in a culture vessel containing a plurality of cell populations at a particular culture-initiation ratio or particular number of cells; and (b) genetically engineering the cells, such as by introducing a genetically engineered antigen receptor into cells in the culture vessel.

In some embodiments, the genetically engineered antigen receptor is introduced into cells in the culture vessel, such as to different cell types or sub-populations within the culture vessel, e.g., to CD4+ and CD8+ cells in the culture vessel.

In some aspects, the methods produce an output composition for genetic engineering or adoptive cell therapy or comprising cells expressing the genetically engineered antigen receptor.

In some embodiments, the isolation includes or is carried out by isolating a CD4+ primary human T cell population and/or a CD8+ primary human T cell population from the sample. In some aspects, it includes depleting or enriching for a sub-population of CD4+ cells, and/or depleting or enriching for a sub-population of CD8+ cells. Thus, in some aspects, the culture-initiating composition includes isolated CD4+ and CD8+ primary human T cells.

In some aspects, the enriching or depleting is carried out by immunoaffinity-based selection, such as binding to antibodies or other binding molecules recognizing surface markers on the cells. In some aspects, the antibody or other molecule is coupled to a magnetically responsive or magnetic particle, e.g., bead. In some aspects, the selection includes positive and/or negative selection steps.

In some embodiments, the isolation of the $CD8^+$ primary human T cell population comprises depleting or enriching for a sub-population of $CD8^+$ cells. In some embodiments, the isolation of the $CD4^+$ primary human T cell population comprises depleting or enriching for a sub-population of $CD4^+$ cells. In some aspects, the isolation of a T cell population comprises enriching for $T_{CM}$ cells. In some aspects, the isolation of the $CD8^+$ and/or the $CD4^+$ primary human T cell population comprises enriching for central memory T ($T_{CM}$) cells. In some aspects, the enrichment for central memory T ($T_{CM}$) cells comprises negative selection for cells expressing a surface marker present on naïve T cells, such as CD45RA, or positive selection for cells expressing a surface marker present on central memory T cells and not present on naïve T cells, such as CD45RO; and/or positive selection for cells expressing surface marker present on central memory T ($T_{CM}$) cells and not present on another memory T cell sub-population, such as CD62L, CCR7, CD27, CD127, and/or CD44.

In some embodiments, the isolation includes (i) subjecting the sample to positive selection based on surface expression of CD4, resulting in a positive and first negative fraction, where the positive fraction is the isolated $CD4^+$ population; and (ii) subjecting the first negative fraction to negative selection based on surface expression of a non-T cell marker and a surface marker present on naïve T cells, thereby generating a second negative fraction; and (iii) subjecting the second negative fraction to positive selection based on surface expression of a marker present on the surface of central memory T ($T_{CM}$) cells and not present on the surface of another memory T cell sub-population.

In some aspects, the marker present on naïve T cells includes CD45RA. In some aspects, the surface marker present on central memory T ($T_{CM}$) cells and not present on another memory T cell sub-population includes CD62L, CCR7, CD27, CD127, and/or CD44.

In some aspects, the isolation or selections are carried out in the same separation vessel. In some aspects, the isolation comprises (i) subjecting the sample to a first selection, thereby generating one of the $CD4^+$ and $CD8^+$ primary human T cell populations and a non-selected sample; and (ii) subjecting the non-selected sample to a second selection, thereby generating the other of the $CD4^+$ and $CD8^+$ primary human T cell populations. In some aspects, the $CD4^+$ primary human T cell population is generated in the first selection and the $CD8^+$ primary human T cell population is generated in the second selection. In some aspects, the first and/or second selection comprises a plurality of positive or negative selection steps.

In some aspects, the isolation of one or more of the populations, such as the primary human T cell population, the primary human CD4+ T cell population, or the primary human CD8+ T cell population, includes positive selection based on surface expression CD62L, CCR7, CD44, or CD27. In some aspects, the isolation of one or more of the populations, such as the primary human T cell population, the primary human $CD4^+$ T cell population, or the primary human $CD8^+$ T cell population, includes negative selection based on surface expression of CD45RA or positive selection based on surface expression of CD45RO.

In some embodiments, the various isolations, such as isolation of the plurality of cell populations, e.g., the $CD4^+$ and the $CD8^+$ populations, are carried out in the same separation vessel. In some aspects, the separation vessel is or includes a tube, tubing set, chamber, unit, well, culture vessel, bag, and/or column. In some aspects, the separation vessel maintains the cells in a contained or sterile environment during the separation.

In some embodiments, the incubating is carried out under stimulating conditions. In some aspects, the culture-initiating composition comprises the $CD4^+$ and $CD8^+$ primary human T cell populations at a culture-initiating ratio. In some aspects, the culture-initiating ratio is designed to yield a desired output ratio of $CD4^+$ to $CD8^+$ cells (or desired total number of T cells or number(s) of the sub-population(s)) following said incubation, or at some later time, such as following engineering, cryopreservation, or at the time just prior to administration, such as at thaw at bedside.

In some embodiments, the desired output ratio is between at or about 5:1 and at or about 1:5 (or greater than about 1:5 and less than about 5:1), such as between at or about 1:3 and at or about 3:1 (or greater than about 1:3 and less than about 3:1), such as between at or about 2:1 and at or about 1:5 (or greater than about 1:5 and less than about 2:1), or is the range of between at or about 2:1 and at or about 1:5. In some aspects, the desired output ratio is at or about 3:1, 2.9:1, 2.8:1, 2.7:1, 2.6:1, 2.5:1, 2.4:1, 2.3:1, 2.2:1, 2.1:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5.

In some aspects, the method results in a ratio of two different cell types or populations, such as a ratio of CD4+ to CD8+ cells, in the output composition that is between at or about 5:1 and at or about 1:5 (or greater than about 1:5 and less than about 5:1), such as between at or about 1:3 and at or about 3:1 (or greater than about 1:3 and less than about 3:1), such as between at or about 2:1 and at or about 1:5 (or greater than about 1:5 and less than about 2:1), or that is at or about 3:1, 2.9:1, 2.8:1, 2.7:1, 2.6:1, 2.5:1, 2.4:1, 2.3:1, 2.2:1, 2.1:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5.

In some aspects, the desired output ratio is 1:1 or is about 1:1.

In some aspects, the methods result in the desired output ratio or cell number(s) in the output composition, results in a ratio or number in the output composition that is within a certain tolerated difference or range of error of such a desired output ratio or number, and/or results in such a ratio or number a certain percentage of the time that the method is performed, such as at least at or about 50%, 55%, 60%, 65%, 70%, 75%, 80%, 85%, 90%, 95%, or more than 95% of the time.

In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio. In some aspects, the output ratio is within 20% of the desired ratio and/or is within that ratio at least 80% of the time the methods are performed.

In some embodiments, the tolerated difference and/or the desired output ratio or number(s) is or has been determined by administering different cell types, such as administering CD4+ and CD8+ cells, to one or more subjects at a plurality of test ratios or numbers, and assessing one or more parameters. In some aspects, the determination of the desired output ratio or number or tolerated difference includes assessing one or more outcomes following administration to the subject. In some aspects, the outcomes include those selected from among amelioration of a disease symptom and outcomes indicating safety and/or low or absence of toxicity.

In some embodiments, the culture-initiation ratio is selected based on a proliferation rate or survival capacity of various cell types isolated, such as the CD4+ and/or CD8+ primary human T cell population. In some embodiments, the culture-initiating ratio is selected based on a source of the sample, such as the subject from which the sample has been derived. For example, in some aspects, the sample is derived from a subject and the culture-initiating ratio is selected based on a disease or condition affecting said subject and/or a treatment the subject is receiving, has received, or will receive, such as a co-treatment for administration with the adoptive cell therapy. In some aspects, the culture-initiating ratio is selected based on a phenotype of one or more of the cells or sub-types of cells being isolated or cultured, such as a phenotype of the CD4+ and/or CD8+ cell populations, such as expression of a cell surface marker or synthesis or secretion of one or more factors, such as cytokines or chemokines.

In some embodiments, the methods comprise selecting the culture-initiation ratio prior to the incubation step. In some aspects, the selection is carried out by measuring a proliferation rate or survival capacity of one or more of the isolated cell populations or populations of cells being incubated, such as the CD4+ primary human T cells and/or the isolated CD8+ primary human T cells. In some aspects, the selection is carried out by assessing a phenotype of the isolated CD4+ primary human T cells and/or the isolated CD8+ primary human T cells. In some aspects, the phenotype selected from among expression of a surface marker and secretion of a cytokine or other factor. In some aspects, the selecting is carried out by assessing the source of the sample, such as where the culture-initiation ratio is selected based on a disease or condition affecting a subject from which the sample is derived.

In some embodiments, the methods further include determining an intermediate ratio or number of cells, such as an intermediate ratio of CD4+ to CD8+ cells, present in the culture vessel at a time point subsequent to the initiation of said incubation. In some aspects, the methods further include adjusting one or more parameters and/or or increasing or decreasing the time for carrying out the incubation and/or engineering steps, based on said intermediate ratio. In one aspect, the adjusting comprises increasing or decreasing the number of or enriching for one or more cell populations in the culture vessel, such as increasing or enriching for CD4+ or CD8+ cells in the culture vessel, adjusting temperature, adding a stimulant to the culture vessel, adjusting the concentration of one or more stimulants in the culture vessel, and/or adding and/or removing a sub-population of cells to or from the culture vessel. In some aspects, the determining and/or adjusting are carried out while maintaining the composition being incubated within a sterile or contained environment. In some aspects, the determination and/or adjusting are carried out in an automated fashion, such as controlled by a computer attached to a device in which the steps are performed.

In some aspects, the isolating, incubating, and/or engineering steps are carried out in a sterile or contained environment and/or in an automated fashion, such as controlled by a computer attached to a device in which the steps are performed.

In some aspects, the CD8+ population in the culture-initiating composition comprises at least 50% central memory T ($T_{CM}$) cells or comprises less than 20% naïve T ($T_N$) cells.

In some embodiments, the sample is obtained from a subject. In some aspects, the subject is a subject to whom said genetically engineered cells, e.g., T cells, or cells for adoptive cell therapy will be administered or subject in need of such administration. In other aspects, the subject is a subject other than a subject to whom said genetically engineered cells, e.g., T cells, or cells for adoptive therapy will be administered or is a subject not in need of such therapy. Among the samples are blood and blood-derived samples, such as white blood cell samples, apheresis samples, leukapheresis samples, peripheral blood mononuclear cell (PBMC) samples, and whole blood.

In some aspects, the stimulating conditions for the incubation or engineering include conditions whereby T cells of the culture-initiating composition proliferate or expand. For example, in some aspects, the incubation is carried out in the presence of an agent capable of activating one or more intracellular signaling domains of one or more components of a TCR complex, such as a CD3 zeta chain, or capable of activating signaling through such a complex or component. In some aspects, the incubation is carried out in the presence of an anti-CD3 antibody, and anti-CD28 antibody, anti-4-1BB antibody, for example, such antibodies coupled to or present on the surface of a solid support, such as a bead, and/or a cytokine, such as IL-2, IL-15, IL-7, and/or IL-21.

In some embodiments, the genetically engineered antigen receptor is or includes a T cell receptor (TCR), such as a high-affinity TCR, or functional non-TCR antigen receptor, such as a chimeric antigen receptor (CAR). In some aspects, the receptor specifically binds to an antigen expressed by cells of a disease or condition to be treated. In some aspects, the CAR contains an extracellular antigen-recognition domain. In some aspects, it further contains an intracellular signaling domain comprising an ITAM-containing sequence and an intracellular signaling domain of a T cell costimulatory molecule.

Also provided are cells and compositions, including pharmaceutical compositions, produced by any of the methods or embodiments, including genetically engineered cells and cells for adoptive cell therapy. Also provided are methods for administering such cells and compositions to subjects and uses of the cells and compositions in such methods. For example, provided are methods of treatment carried out by producing cells according to the cell production methods and administering cells of the output composition or a composition derived therefrom to a subject. Provided are methods of treatment including administering the provided cells or compositions to a subject. In some aspects, the sample from which the cells are isolated is derived from the subject to which the cells are administered. In some aspects, the sample is from a different subject. Thus, the methods include autologous and allogeneic methods. In some embodiments, the methods ameliorate, treat, or prevent one or more symptoms of a disease or condition in the subject. In some aspects, the disease or condition is a cancer or associated symptom. In some embodiments, the cancers include leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin (including melanoma), bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma.

DETAILED DESCRIPTION

Figure 1A:
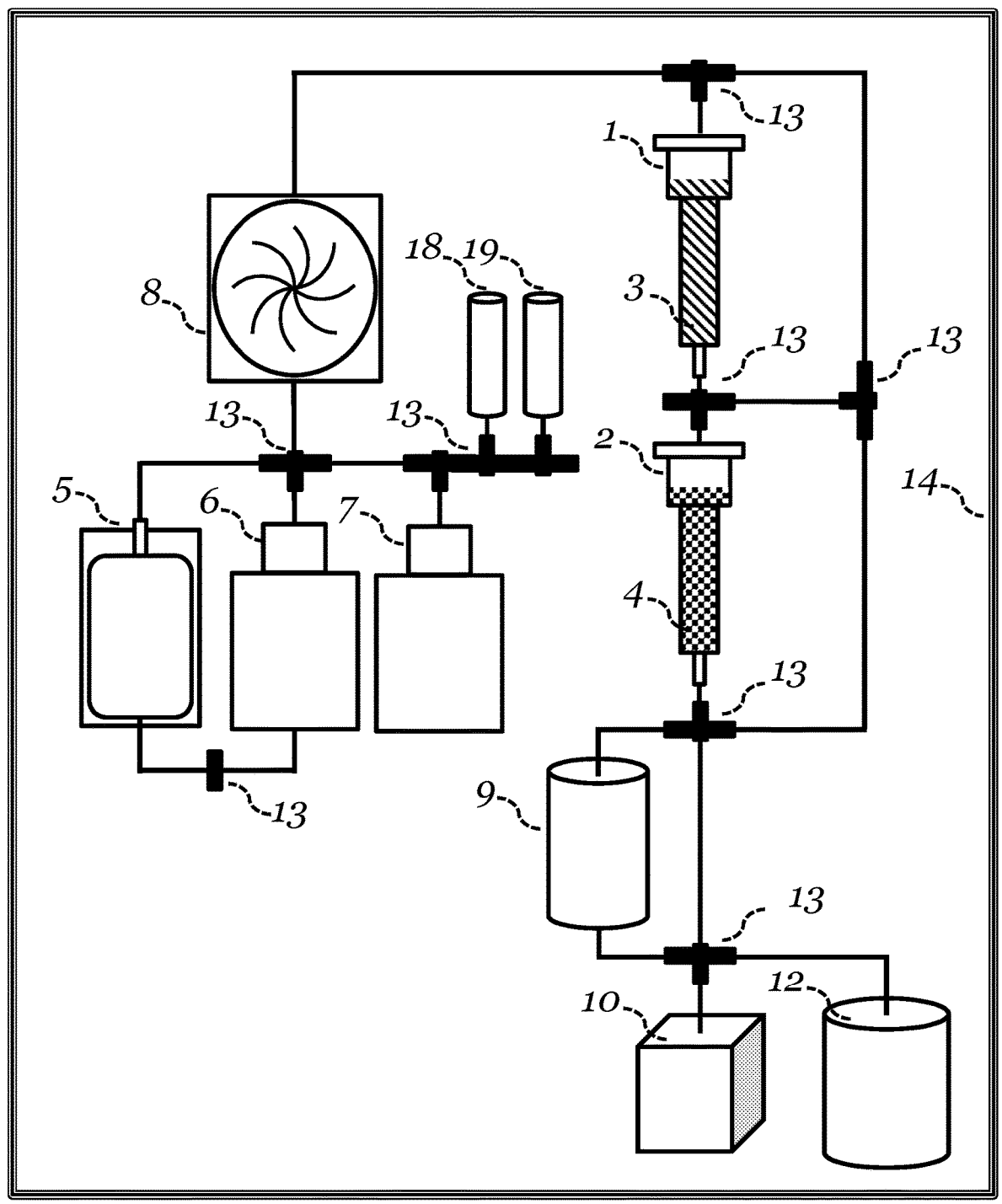
FIG. 1A: provides a schematic representation of an embodiment of a closed system for use in embodiments of the provided methods. The depicted exemplary system includes a cell sample 5, a washing buffer reservoir 6, an elution buffer reservoir 7, a first Fab reservoir 18, a second Fab reservoir 19, and a pump 8, connected through a series of tubing and valves 13, to a first chromatography column 1 containing a first matrix 3 operably linked via a series of tubing lines to a second chromatography column 2 containing a second matrix 4. The second chromatography column 2 is operably linked to a removal chamber 9. The removal chamber 9 is operably linked to a valve 13, which directs cells and fluids to a waste container 10 or a culture vessel 12 via a series of tubing lines. The system is enclosed in an enclosure 14.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Methods and Systems for Isolatinm, Culturinm, and Enmineerinm Cells for Adoptive Therapy Provided are methods of preparing cells, e.g., T cells, for use in genetic engineering and therapeutic methods such as adoptive cell therapy. Specifically, in some embodiments, the methods use or generate compositions that contain a plurality of different cell populations or types of cells, such as isolated CD4$^+$ and CD8$^+$ T cell populations and subpopulations. In some embodiments, the methods include steps for isolating one or more cell populations, generally a plurality of cell populations. The cells generally are isolated from a sample derived from a subject.

In some aspects, the methods are performed by employing simultaneous or sequential selections or enrichments in which a plurality of different cell populations, such as CD4+ or CD8+ cells, from a sample, such as a sample containing primary human T cells, are selected, enriched and/or isolated. In some embodiments, such methods are performed using a single processing stream in which a first population of cells, such as CD4+ or CD8+ cells, and a second population of cells, such as the other of the CD4+ or CD8+ cells, are selected, enriched and/or isolated without discarded any cells from the first population prior to performing the selection of the second population of cells. In some aspects, the first and second selections can be performed simultaneously or sequentially. In some embodiments, the methods of selection are performed as a single process stream by performing a first selection to enrich for a first population of cells, such as one of CD4+ and CD8+ cells from a sample, such as a sample containing primary human T cells, and using the non-selected cells from the first selection as the source of cells for a second selection, such as for the other of the CD4+ or CD8+ cells from the sample.

In some embodiments, a further selection or selections can be performed of the first or second selected cells. In some embodiments, the further selection enriches for a sub-population of CD4+ or CD8+ cells expressing a marker on central memory T ($T_{CM}$) cells and/or enriches for a sub-population of cells expressing CD62L, CD45RA, CD45RO, CCR7, CD27, CD127, or CD44.

In some embodiments, the methods of selection are performed in a closed system or apparatus. In some embodiments, within the closed system or apparatus, a composition, such as a culture-initiation composition, is generated containing the enriched or selected population of cells, such as both the enriched or selected CD4+ and CD8+ populations, in the same composition.

For example, in some aspects, the one or more steps are carried out with the plurality of cell populations combined in the same composition, or present in the same vessel, e.g., in the same closed system or apparatus, or in the same vessel, unit, or chamber, such as the same column, e.g., magnetic separation column, tube, tubing set, culture or cultivation chamber, culture vessel, processing unit, cell separation vessel, centrifugation chamber, or using the same separation matrix, media, and/or reagents, such as the same magnetic or magnetically responsive matrix, particle, or bead, the same solid support, e.g., affinity-labeled solid support, and/or the same antibodies and/or other binding partners, such as fluorescently-labeled antibodies and binding partners, for the plurality of cell populations. In some embodiments, the one or more vessels, units or chambers, such as columns, are operably connected in the same closed system or apparatus, so that the methods of isolation, selection and/or enriching occurs in a single process stream in which a non-selected cell population from a first selection can be used as a source of cells for a second selection.

In some embodiments, the isolation of or enrichment for one or more specific populations or sub-populations of cells, e.g., CD4+ and CD8+ T cells to be cultured or engineered for adoptive therapy, provides one or more advantages. For example, engineering cells enriched for a plurality of different cell populations or types of cells, such as isolated CD4+ and CD8+ T cell populations and sub-populations, can improve efficacy of or reduce or avoid unwanted effects. In some aspects, the isolation or enrichment increases the ability of cells ultimately administered to a subject to persist, expand, become activated, and/or engraft in vivo or upon administration to a subject. In some aspects, it improves or increases one or more effector function or activation phenotype. For example, in some aspects, enriching a T cell population, such as a CD8+ T cell population, for central memory ($T_{CM}$) cells can provide such advantages. In some aspects, one or more of such advantages are provided by combining two or more isolated populations or sub-types, such as isolated populations or sub-populations of CD8+ and CD4+ T cells, such as a $Tc_M$-enriched $CD8^+$ population and a $CD4^+$ population. For example, such advantages can be achieved in some aspects by administering a CD4+ and a CD8+ population in comparison with a CD8+ population alone.

The methods in some embodiments include processing of a generated composition containing a plurality of the isolated or selected cell populations, such as a population of selected or enriched CD4+ cells and CD8+ cells. In one embodiment, processing of the generated composition includes incubating the cells under stimulating conditions, for example in some aspects, to activate the cells for engineering or transduction or for cell expansion. The methods, in some embodiments, include steps for engineering a plurality of cell types, such as CD4+ cells and CD8+ cells, such as those isolated and present in the incubated composition, such as the culture-initiation composition. In some aspects, the engineering is carried out to introduce a genetically engineered antigen receptor into the cells, such as a TCR, e.g., a high-affinity TCR, or a functional non-TCR antigen receptor, such as a chimeric antigen receptor (CAR). In some aspects, the methods include further processing, such as further incubation, for example at or about 37° C.±2° C., and/or formulating of cells and compositions containing the same. In some embodiments, the processing produces a resulting output composition containing genetically engineered cells, such as genetically engineered CD4+ cells and CD8+ cells. In some embodiments, the resulting processed output composition can be used in methods for administering cells and compositions prepared by the methods to a patient, for example, in connection with adoptive cell therapy.

Figure 1B:
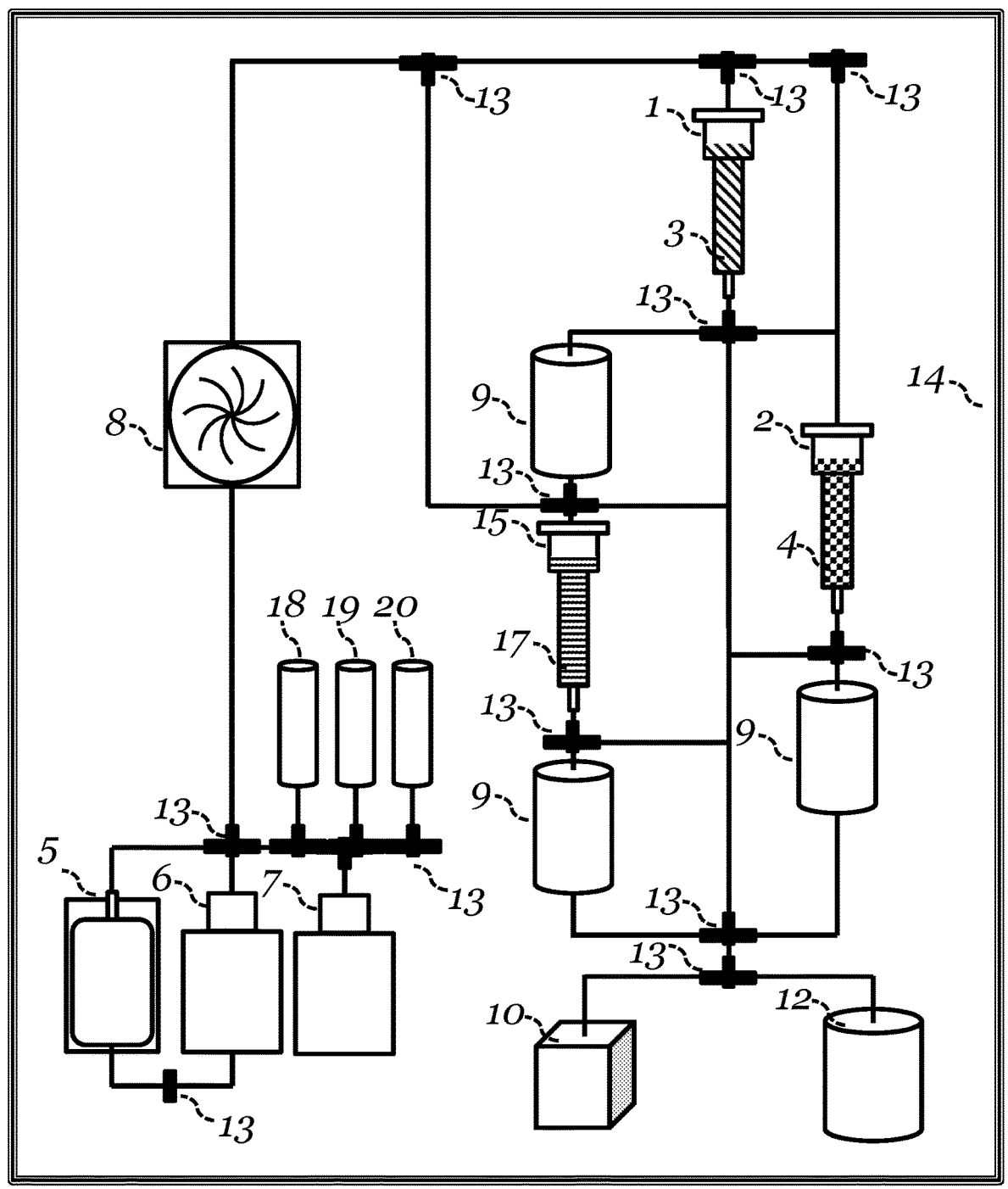
FIG. 1B: provides a schematic representation of an embodiment of a closed system for use in embodiments of the provided methods. The depicted exemplary system includes a cell sample 5, a washing buffer reservoir 6, an elution buffer reservoir 7, a first Fab reservoir 18, a second Fab reservoir 19, a third Fab reservoir 20, and a pump 8, connected through a series of tubing to a first chromatography column 1 containing a first matrix 3. Valves 13 operably linked to the series of tubing direct fluids through the series of tubing. A valve 13 operably linked to the first chromatography column 1 directs cells and fluids to a second chromatography column 2 containing a second matrix 4, which is operably linked to a removal chamber 9. The valve 13 operably linked to the first chromatography column 1 also directs cells and fluids to a removal chamber 9, which is operably linked to a third chromatography column 15 containing a third matrix 16. The third chromatography column 15 is operably linked to a removal chamber 9. The removal chambers 9 are operably linked to a first waste container 10 or a culture vessel 12 via the series of tubing lines and valves 13. The system is enclosed in an enclosure 14.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1. In some embodiments, the system is a closed apparatus or system, such as is depicted in FIG. 1A or FIG. 1B. In some embodiments, the system or apparatus is automated and/or carries out the selection steps to enrich cells according to the methods in an automated fashion.

In some embodiments, the system or apparatus carries out the isolation, such as selection or enrichments steps. In some embodiments, a further system or apparatus, such as a closed system or apparatus, can be used to carry out one or more of the other steps such as cells preparation, processing, incubation, culture and/or formulation steps of the method. In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some embodiments, because the enriched composition, such as culture initiation composition, is generated by the provided methods to contain different cell populations, such as CD4+ and CD8+, the generated composition can be processed together and simultaneously under the same conditions, and in some aspects, in a closed system. Thus, in some aspects, the methods provide a process to produce and process a population of selected, enriched or isolated cells containing different populations of cells, such as CD4+ and CD8+ cells, in a single process stream. In some aspects, this differs from prior art methods, including prior art methods that process cells for engineering for adoptive cell therapy, which typically include a separate process stream for each different cell population, such as at least two process streams. For example, in some aspects of existing methods, CD4+ T cells are separately isolated, enriched and/or selected and processed under stimulating conditions for genetic engineering, CD8+ T cells are separately isolated, enriched and/or selected and processed under stimulating conditions for genetic engineering, and the separate processed and engineered CD4+ and CD8+ T cells are recombined prior to administration to a subject.

In some embodiments, the methods provide one or more advantages compared with other preparation, isolation, incubation, and engineering methods, such as cost, time, and/or resource savings. Such advantages can include the ability to isolate, process, e.g., incubate, and/or engineer the plurality of cell populations, present at or near a desired ratio, with increased efficiency and/or reduced complexity, time, cost, and/or use of resources, compared with other methods.

In some embodiments, such advantages are achieved by streamlining one or more of the method steps. For example, in some aspects, isolation, culture, and/or engineering of the different populations is carried out using the same apparatus or equipment and/or simultaneously. In some aspects, the isolation, culture, and/or engineering of the different populations is carried out based on the same starting composition. In some aspects, such features of the methods reduce the amount of time, method steps, cost, complexity, and/or number of resources, compared to a method in which the cell populations are isolated, incubated, and/or engineered separately, in separate vessels, using separate equipment, at separate times, and/or beginning with different starting compositions.

In some aspects, the methods of isolating, incubating and engineering cells results in an output composition in which the different cell populations or cell types, such as $CD4^+$ cells and $CD8^+$ cells, are present at a desired ratio, or within a certain degree of tolerated error of the desired ratio. Such ratios include those deemed optimal for the therapeutic use, e.g., output ratios deemed appropriate or optimal for administration to a patient in connection with adoptive cell therapy. Also provided are methods for administering cells and compositions prepared by the methods to a patient, for example, in connection with adoptive cell therapy In some embodiments, the methods of isolation or selection are performed to achieve selection of cells at a chosen culture-initiation ratio of CD4+ cells to CD8+ cells or a sub-population thereof. In some aspects, such ratios include ratios deemed optimal starting points for achieving an optimal ratio, such as a desired ratio in the output composition, at the completion of the method or one or more steps, such as following a culture, incubation, and/or engineering step. In some embodiments, providing the cells at a culture-initiation ratio, such as a ratio of CD4+ cells to CD8+ cells, accounts for differences in expansion of CD4+ and CD8+ T cells that can occur upon stimulation or activation with different reagents, in order to achieve a desired ratio in the output composition.

In some embodiments, the methods generate engineered cells or cells for engineering at or within a certain percentage of a desired output ratio, or do so at least a certain percentage of the time. The desired output ratio typically is a ratio that has been determined to be optimal for administration to a patient via adoptive transfer. In some embodiments, the populations or sub-types of cells, such as $CD8^+$ and $CD4^+$ T cells are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In some embodiments, provided are methods for determining such optimal output ratios and/or desired doses, and/or levels of variance from the desired output ratio or desired dose that would be tolerated, e.g., a tolerated difference. In some embodiments, in order to achieve the desired output ratio or dose(s) (or to achieve such a ratio a certain percentage of the time or within a certain tolerated difference), the cell populations are combined or incubated at ratios (e.g., culture-initiation ratios) designed to achieve the desired output ratio for adoptive transfer.

Also provided are methods for determining a culture-initiation ratio designed to achieve the desired output ratio or dose to do so within a certain tolerated difference and/or a certain percentage of the time. Also provided are methods for assessing interim ratios or numbers of the cell populations, such as at one or more periods of times over the course of the various method steps, e.g., during incubation. Also provided are methods for adjusting various conditions, such as culture conditions, based on such assessments. In some aspects, the adjustments are carried out to ensure that a particular output ratio or dose is achieved or achieved within a tolerated difference.

In particular embodiments, provided are streamlined methods for preparing a composition having at or near a desired output ratio of a $CD4^+$ T cell population and a $CD8^+$ T cell population (e.g., a CD8+ population enriched for a sub-type of T cells such as central memory T cells), and/or a desired dose (e.g., number or number per unit of body weight) of T cells and/or of CD4+ and CD8+ T cells, for introduction of a genetically engineered antigen receptor for use in adoptive cell therapy, where the cell populations are isolated, incubated, and/or engineered in combination and the method is associated with increased efficiency and/or reduced complexity, time, cost, and/or use of resources compared to a method in which the populations are isolated, incubated, and/or engineered separately.

Also provided are cells and compositions prepared by the methods, including pharmaceutical compositions and formulations, and kits, systems, and devices for carrying out the methods. Also provided are methods for use of the cells and compositions prepared by the methods, including therapeutic methods, such as methods for adoptive cell therapy, and pharmaceutical compositions for administration to subjects.

A. Isolation, Isolated Cells, and Other Processing Steps

Among the provided embodiments are methods for isolating a plurality of cells and populations of cells from a sample, as well as isolated, such as enriched, cells produced by such methods. The isolation can include one or more of various cell preparation and separation steps, including separation based on one or more properties, such as size, density, sensitivity or resistance to particular reagents, and/or affinity, e.g., immunoaffinity, to antibodies or other binding partners. In some aspects, the isolation is carried out using the same apparatus or equipment sequentially in a single process stream and/or simultaneously. In some aspects, the isolation, culture, and/or engineering of the different populations is carried out from the same starting composition or material, such as from the same sample.

In some aspects, the plurality of cell populations are isolated in the same closed system or apparatus, and/or in the same vessel or set of vessels, e.g., same (or same set of) unit, chamber, column, e.g., magnetic separation column, tube, tubing set, culture or cultivation chamber, culture vessel, processing unit, cell separation vessel, centrifugation chamber. For example, in some cases, the isolation of a plurality of cell populations is carried out a system or apparatus employing a single or the same isolation or separation vessel or set of vessels, such as a single column or set of columns, and/or same tube, or tubing set, for example, without requirements to transfer the cell population, composition, or suspension from one vessel, e.g., tubing set, to another.

In some aspects, such methods are achieved by a single process stream, such as in a closed system, by employing simultaneous or sequential selections in which a plurality of different cell populations, such as CD4+ or CD8+ cells, from a sample, such as a sample containing primary human T cells, are selected, enriched and/or isolated. In one embodiment, a sample containing cells is subjected to a selection by simultaneous enrichment of both the CD4+ and CD8+ populations. In some aspects, carrying out the separation or isolation in the same vessel or set of vessels, e.g., tubing set, is achieved by carrying out sequential positive and negative selection steps, the subsequent step subjecting the negative and/or positive fraction from the previous step to further selection, where the entire process is carried out in the same tube or tubing set. In one embodiment, a sample containing cells to be selected is subjected to a sequential selection in which a first selection is effected to enrich for one of the CD4+ or CD8+ populations, and the non-selected cells from the first selection is used as the source of cells for a second selection to enrich for the other of the CD4+ or CD8+ populations. In some embodiments, a further selection or selections can be effected to enrich for sub-populations of one or both of the CD4+ or CD8+ population, for example, central memory T ($T_{CM}$) cells.

In a particular aspect, a first selection step is carried out using beads labeled with CD4-binding molecules, such as antibodies (or secondary reagents that recognize such molecules), and the positive and negative fractions from the first selection step are retained, followed by further positive or negative selection of the negative fraction to enrich for CD8+ cells, such as by using beads labeled with CD8-binding molecules, and optionally selection of a sub-population of cells from the CD8+ fraction, such as central memory CD8+ T cells and/or cells expressing one or more markers CD62L, CD45RA, CD45RO, CCR7, CD27, CD127, or CD44. In some embodiments, the order of the selections can be reversed. In some embodiments, a CD4 selection is always performed first and, from the negative fraction (CD4−), the CD8+ fraction is enriched in a second selection, e.g., by negative selection for one or more of CD45RA+ and CD14, and/or positive selection for one or more of CD62L, CCR7, and/or other markers expressed on central memory cells.

In some embodiments, a plurality of cell populations, e.g., a CD4+ T cell population and a CD8+ T cell population, is isolated, for example, to produce a culture-initiating composition containing the plurality of cell populations. The culture-initiating composition typically contains the cells at a culture-initiating ratio, which is designed to yield a particular desired output ratio of two or more cell types, such as a particular CD4+ to CD8+ ratio, following one or more incubation, culture, cultivation, and/or engineering steps. The desired output ratio in some embodiments is a ratio designed to be optimal for administration of the cells to a patient, e.g., in adoptive cell therapy.

In some aspects, isolating the plurality of populations in a single or in the same isolation or separation vessel or set of vessels, such as a single column or set of columns, and/or same tube, or tubing set or using the same separation matrix or media or reagents, such as the same magnetic matrix, affinity-labeled solid support, or antibodies or other binding partners, include features that streamline the isolation, for example, resulting in reduced cost, time, complexity, need for handling of samples, use of resources, reagents, or equipment. In some aspects, such features are advantageous in that they minimize cost, efficiency, time, and/or complexity associated with the methods, and/or avoid potential harm to the cell product, such as harm caused by infection, contamination, and/or changes in temperature.

In some embodiments the isolated cell populations obtained for use in the methods herein are sterile. Microbial contamination of cell separation products can in some cases lead to the infection of the recipient subject, such as an immunocompromised recipient patient unable to fight the infection. In some embodiments, the cells, cell populations, and compositions are produced under GMP (good manufacturing practice) conditions. In some embodiments, GMP conditions comprise stringent batch testing. In certain embodiments, tissue typing is performed prior to transplantation, e.g., to avoid human leukocyte antigen (HLA) mismatch and prevent problems such as graft-versus-host disease. In some embodiments, the provided methods reduce handling by individual users and automate various steps, which in some aspects can increase consistency of the isolated cell populations and compositions and reduces error, thereby promoting consistency of the therapy and safety.

1. Cells and Populations of Cells

In some embodiments, the methods include performing a selection, isolation and/or enrichment of a cell sample, such as a primary human cell sample. The isolated cell populations typically include a plurality of cell populations, generally populations of blood or blood-derived cells, such as hematopoietic cells, leukocytes (white blood cells), peripheral blood mononuclear cells (PBMCs), and/or cells of the immune system, e.g., cells of the innate or adaptive immunity, such as myeloid or lymphoid cells, e.g., lymphocytes, typically T cells and/or NK cells. In some embodiments, the sample is an apheresis or leukapheresis sample. In some embodiments, the selection, isolation and/or enrichment can include positive or negative selection of cells from the sample.

In some embodiments, the sample is a sample containing primary human T cells, such as CD4+ and CD8+ T cells. In particular embodiments, the sample is one in which a plurality of T cell populations is isolated, such as a population of CD4$^+$ cells and a population of CD8$^+$ T cells. Thus, in some embodiments, the isolation includes positive selection for cells expressing CD4 or cells expressing CD8 and/or negative selection for cells expressing non-T cell markers, such as myeloid or B cell markers, for example, negative selection for cells expressing CD14, CD19, CD56, CD20, CD11b, and/or CD16.

In some embodiments, the sample is one containing a plurality of populations that includes a T cell population, such as a whole T cell or CD4+ population, and an NK cell population. Among the T cell populations that can be enriched, isolated and/or selected are populations of unfractionated T cells, unfractionated CD4+ cells, unfractionated CD8+ cells, and sub-populations of CD4+ and/or CD8+ T cells, including subpopulations of T cells generated by enrichment for or depletion of cells of a particular sub-type or based on a particular surface marker expression profile.

For example, among the sub-types of T cells (e.g., CD4$^+$ or CD8$^+$ T cells) that can be enriched, isolated and/or selected are those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation.

Among the sub-types and subpopulations of T cells and/or of CD4+ and/or of CD8+ T cells that can be enriched, isolated and/or selected are naïve T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations enriched, isolated and/or selected from a sample by the provided methods are cells that are positive for (marker+) or express high levels (markerhigh) of one or more particular markers, such as surface markers, or that are negative for (marker-) or express relatively low levels (markerlow) of one or more markers. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Rα (CD127). In some examples, CD8+ T cells are enriched for cells positive for CD45RO (or negative for CD45RA) and for CD62L.

In some embodiments, a CD4+ T cell population and a CD8+ T cell sub-population, e.g., a sub-population enriched for central memory (TCM) cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

2. Samples

The cells and cell populations typically are isolated from a sample, such as a biological sample, e.g., one obtained from or derived from a subject, such as one having a particular disease or condition or in need of a cell therapy or to which cell therapy will be administered. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

3. Cell Processing, Preparation and Non-Affinity-Based Separation

In some embodiments, isolation of the cells or populations includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

4. Separation Based on Affinity and/or Marker Profile

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells. For example, in some aspects, a selection of one of the CD4+ or CD8+ population enriches for said population, either the CD4+ or CD8+ population, but also can contain some residual or small percentage of other non-selected cells, which can, in some cases, include the other of the CD4 or CD8 population still being present in the enriched population.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, CD62L+, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some embodiments, the methods include isolation, selection and/or enrichment of CD4+ and CD8+ cells. In one example, to enrich for $CD4^+$ cells by negative selection, a monoclonal antibody cocktail typically includes antibodies to CD14, CD20, CD11b, CD16 and HLA-DR. In one example, to enrich for a $CD8^+$ population by negative selection is carried out by depletion of cells expressing CD14 and/or CD45RA. In some aspects, a $CD4^+$ or $CD8^+$ selection step, such as positive selection for CD4 and positive selection for CD8, is used to separate $CD4^+$ helper and $CD8^+$ cytotoxic T cells. Such selections in some aspects are carried out simultaneously and in other aspects are carried out sequentially, in either order.

In some aspects, the methods include a first positive selection for CD4+ cells in which the non-selected cells (CD4– cells) from the first selection are used as the source of cells for a second positive selection to enrich for CD8+ cells. In some aspects, the methods include a first positive selection for CD8+ cells in which the non-selected cells (CD8– cells) from the first selection are used as the source of cells for a second position selection to enrich for CD4+ cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, CD4+ cells are further enriched for or depleted of naïve, central memory, effector memory and/or central memory stem cells, such as by positive or negative selection based on surface antigens associated with the respective population. CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining $T_{CM}$-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L-CD8+ and/or CD62L+ CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, CD27 and/or CD 127; in some aspects, it is based on negative selection for cells expressing or highly expressing CD45RA and/or granzyme B.

In some embodiments, the provided methods include isolation, selection and/or enrichment of CD8+ cells from a sample, such as by positive selection based on surface expression of CD8. In some embodiments, the methods can further include enriching for central memory T ($T_{CM}$) cells. In one aspect, the enriched CD8+ cells can be further enriched for central memory T ($T_{CM}$) cells by selecting for one or more markers expressed on central memory T ($T_{CM}$) cells, such as one or more of CD45RO, CD62L, CCR7, CD28, CD3, CD27 and/or CD 127. The selection can be performed prior to or subsequent to isolation, selection and/or enrichment of CD4+ cells. Such selections in some aspects are carried out simultaneously and in other aspects are carried out sequentially, in either order.

In some aspects, the methods include a first positive selection for CD4+ cells in which the non-selected cells (CD4− cells) from the first selection are used as the source of cells for a second selection to enrich for CD8+ cells, and the enriched or selected CD8+ cells are used in a third selection to further enrich for cells expressing one or more markers expressed on central memory T ($T_{CM}$) cells, such as by a third selection to enrich for CD45RO+, CD62L+, CCR7+, CD28+, CD3+, CD27+ and/or CD127+ cells. In some aspects, the methods include a first positive selection for CD8+ cells in which the non-selected cells (CD8− cells) from the first selection are used as the source of cells for the second selection to enrich for CD4+ cells, and the enriched or selected CD8+ cells from the first selection also are used in a third selection to further enrich for cells expressing one or more markers expressed on central memory T ($T_{CM}$) cells, such as by a third selection to enrich for CD45RO+, CD62L+, CCR7+, CD28+, CD3+, CD27+ and/or CD127+ cells.

In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

In some embodiments, the methods of isolating, selecting and/or enriching for cells, such as by positive or negative selection based on the expression of a cell surface marker or markers, for example by any of the methods described above, can include immunoaffinity-based selections. In some embodiments, the immunoaffinity-based selections include contacting a sample containing cells, such as primary human T cells containing CD4+ and CD8+ cells, with an antibody or binding partner that specifically binds to the cell surface marker or markers. In some embodiments, the antibody or binding partner is bound to a solid support or matrix, such as a sphere or bead, for example microbeads, nanobeads, including agarose, magnetic bead or paramagnetic beads, to allow for separation of cells for positive and/or negative selection. In some embodiments, the spheres or beads can be packed into a column to effect immunoaffinity chromatography, in which a sample containing cells, such as primary human T cells containing CD4+ and CD8+ cells, is contacted with the matrix of the column and subsequently eluted or released therefrom.

a. Immunoaffinity Beads

For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, the sample or composition of cells to be separated is incubated with small, magnetizable or magnetically responsive material, such as magnetically responsive particles or microparticles, such as paramagnetic beads. The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select. Such beads are known and are commercially available from a variety of sources including, in some aspects, Dynabeads® (Life Technologies, Carlsbad, CA), MACS® beads (Miltenyi Biotec, San Diego, CA) or Streptamer® bead reagents (IBA, Germany).

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, the affinity-based selection employs Streptamers®, which are magnetic beads, such as nanobeads or microbeads, for example 1-2 µM that, in some aspects, are conjugated to a binding partner immunoaffinity reagent, such as an antibody via a streptavidin mutant, e.g. Strep-Tactin® or Strep-Tactin XT® (see e.g. U.S. Pat. No. 6,103,493, International Published PCT Appl. Nos. WO/2013011011, WO 2014/076277). In some embodiments, the streptavidin mutant is functionalized, coated and/or immobilized on the bead.

In some embodiments, the streptavidin mutant exhibits a higher binding affinity for a peptide ligand containing the sequence of amino acids set forth in any of SEQ ID NOS:1-6, such as for example SEQ ID NO:5 and/or SEQ ID NO:6 (e.g. Strep-tag II®), than an unmodified or wild type streptavidin, such as an unmodified or wild type streptavidin set forth in SEQ ID NO: 11 or SEQ ID NO:14. In some embodiments, the streptavidin mutant exhibits a binding affinity as an affinity constant for such peptides that is greater than the binding affinity of wild type streptavidin for the same peptide by greater than 5-fold, 10-fold, 50-fold, 100-fold, 200-fold or greater.

The streptavidin mutein contains one or more amino acid differences compared to an unmodified streptavidin, such as a wild type streptavidin or fragment thereof. The term "unmodified streptavidin" refers to a starting polypeptide to which one or more modifications are made. In some embodiments, the starting or unmodified polypeptide may be a wild type polypeptide set forth in SEQ ID NO:11. In some embodiments, the unmodified streptavidin is a fragment of wild type streptavidin, which is shortened at the N- and/or C-terminus. Such minimal streptavidins include any that begin N-terminally in the region of amino acid positions 10 to 16 of SEQ ID NO:11 and terminate C-terminally in the region of amino acid positions 133 to 142 of SEQ ID NO:11. In some embodiments, the unmodified streptavidin has the sequence of amino acids set forth in SEQ ID NO:14. In some embodiments, the unmodified streptavidin, such as set forth in SEQ ID NO:14, can further contain an N-terminal methionine at a position corresponding to Ala13 with numbering as set forth in SEQ ID NO:11. Reference to number of residues in streptavidin provided herein is with reference to numbering of residues in SEQ ID NO:11.

The term "streptavidin mutein," "streptavidin mutant" or variations thereof, refers to a streptavidin protein that contains one or more amino acid differences compared to an unmodified or wild type streptavidin, such as a streptavidin set forth in SEQ ID NO: 11 or SEQ ID NO:14. The one or more amino acid differences can be amino acid mutations, such as one or more amino acid replacements (substitutions), insertions or deletions. In some embodiments, a streptavidin mutein can have at least 1, 2, 3, 4, 5, 6, 7, 8, 9, 10, 11, 12, 13, 14, 15, 16, 17, 18, 19 or 20 amino acid differences compared to a wild type or unmodified streptavidin. In some embodiments, the amino acid replacements (substitutions) are conservative or non-conservative mutations. The streptavidin mutein containing the one or more amino acid differences exhibits a binding affinity as an affinity constant that is greater than $2.7 \times 10^4$ $M^{-1}$ for the peptide ligand (Trp Arg His Pro Gln Phe Gly Gly; also called Strep-tag®, set forth in SEQ ID NO:5). In some embodiments, the streptavidin mutant exhibits a binding affinity as an affinity constant that is greater than $1.4 \times 10^4$ $M^{-1}$ for the peptide ligand (Trp Ser His Pro Gln Phe Glu Lys; also called Strep-tag® II, set forth in SEQ ID NO:6). In some embodiments, binding affinity can be determined by methods known in the art, such as any described below.

In some embodiments, the streptavidin mutein contains a mutation at one or more residues 44, 45, 46, and/or 47. In some embodiments, the streptavidin mutant contains residues Val44-Thr45-Ala46-Arg47, such as set forth in exemplary streptavidin muteins set forth in SEQ ID NO: 12 or SEQ ID NO:15. In some embodiments, the streptavidin mutein contains residues Ile44-Gly45-Ala-46-Arg47, such as set forth in exemplary streptavidin muteins set forth in SEQ ID NO: 13 or 16. In some embodiments, the streptavidin mutein exhibits the sequence of amino acids set forth in SEQ ID NO: 12, 13, 15 or 16, or a sequence of amino acids that exhibits at least 90%, 91%, 92%, 93%, 94%, 95%, 96%, 97%, 98%, 99% or more sequence identity to the sequence of amino acids set forth in SEQ ID NO:12, 13, 15 or 16, and exhibits a binding affinity that is greater than $2.7 \times 10^4$ $M^{-1}$ for the peptide ligand (Trp Arg His Pro Gln Phe Gly Gly; also called Strep-tag®, set forth in SEQ ID NO:5) and/or greater than $1.4 \times 10^4$ $M^{-1}$ for the peptide ligand (Trp Ser His Pro Gln Phe Glu Lys; also called Strep-tag® II, set forth in SEQ ID NO:6).

In some embodiment, the streptavidin mutein is a mutant as described in International Published PCT Appl. Nos. WO 2014/076277. In some embodiments, the streptavidin mutein contains at least two cysteine residues in the region of amino acid positions 44 to 53 with reference to amino acid positions set forth in SEQ ID NO:11. In some embodiments, the cysteine residues are present at positions 45 and 52 to create a disulfide bridge connecting these amino acids. In such an embodiment, amino acid 44 is typically glycine or alanine and amino acid 46 is typically alanine or glycine and amino acid 47 is typically arginine. In some embodiments, the streptavidin mutein contains at least one mutation or amino acid difference in the region of amino acids residues 115 to 121 with reference to amino acid positions set forth in SEQ ID NO:11. In some embodiments, the streptavidin mutein contains at least one mutation at amino acid position 117, 120 and 121 and/or a deletion of amino acids 118 and 119 and substitution of at least amino acid position 121.

In some embodiments, a streptavidin mutein can contain any of the above mutations in any combination, so long as the resulting streptavidin mutein exhibits a binding affinity that is greater than $2.7 \times 10^4$ $M^{-1}$ for the peptide ligand (Trp Arg His Pro Gln Phe Gly Gly; also called Strep-tag®, set forth in SEQ ID NO:5) and/or greater than $1.4 \times 10^4$ $M^{-1}$ for the peptide ligand (Trp Ser His Pro Gln Phe Glu Lys; also called Strep-tag® II, set forth in SEQ ID NO:6).

In some embodiments, the binding affinity of a streptavidin mutant for a peptide ligand binding reagent is greater than $5 \times 10^4$ $M^{-1}$, $1 \times 10^5$ $M^{-1}$, $5 \times 10$ $M^{-1}$, $1 \times 10^6$ $M^{-1}$, $5 \times 10^6$ $M^{-1}$ or $1 \times 10^7$ $M^{-1}$, but generally is less than $1 \times 10^{13}$ $M^{-1}$, $1 \times 10^{12}$ $M^{-1}$ or $1 \times 10^{11}$ $M^{-1}$.

In some embodiments, the streptavidin mutant also exhibits binding to other streptavidin ligands, such as but not limited to, biotin, iminobiotin, lipoic acid, desthiobiotin, diaminobiotin, HABA (hydroxyazobenzene-benzoic acid) or/and dimethyl-HABA. In some embodiments, the streptavidin muteins exhibits a binding affinity for another streptavidin ligand, such as biotin or desthiobiotin, that is greater than the binding affinity of the streptavidin mutein for the peptide ligand (Trp Arg His Pro Gln Phe Gly Gly; also called Strep-tag®, set forth in SEQ ID NO:5) or the peptide ligand (Trp Ser His Pro Gln Phe Glu Lys; also called Strep-tag® II, set forth in SEQ ID NO:6).

In some embodiments, the streptavidin mutein is a multimer. Multimers can be generated using any methods known in the art, such as any described in published U.S. Patent Application No. US2004/0082012. In some embodiments, oligomers or polymers of muteins can be prepared by the introduction of carboxyl residues into a polysaccharide, e.g. dextran. In some aspects, streptavidin muteins then are coupled via primary amino groups of internal lysine residues and/or the free N-terminus to the carboxyl groups in the dextran backbone using conventional carbodiimide chemistry in a second step. In some embodiments, the coupling reaction is performed at a molar ratio of about 60 moles streptavidin mutant per mole of dextran. In some embodiments, oligomers or polymers of can also be obtained by crosslinking via bifunctional linkers, such as glutardialdehyde or by other methods known in the art.

In some aspects, an immunoaffinity bead, such as a Streptamer® or other immunoaffinity bead, can contain an antibody produced by or derived from a hybridoma as follows: OKT3 (αCD3), 13B8.2 (αCD4), OKT8 (αCD8), FRT5 (αCD25), DREG56 (αCD62L), MEM56 (αCD45RA). In some embodiments, any of the above antibodies can contain one or more mutations within the framework of heavy and light chain variable regions without targeting the highly variable CDR regions. Exemplary of such antibodies include, in some aspects, anti-CD4 antibodies as described in U.S. Pat. No. 7,482,000 and Bes et al. (2003) J. Biol. Chem., 278:14265-14273. In some embodiments, an antigen-binding fragment, such as a Fab fragment, can be generated from such antibodies using methods known in the art, such as, in some aspects, amplification of hypervariable sequences of heavy and light chains and cloning to allow combination with sequences coding for an appropriate constant domain. In some embodiments, the constant domain is of human subclass IgG1/κ. Such antibodies can be carboxy-terminally fused with a peptide streptavidin binding molecule, such as set forth in SEQ ID NO:10. Exemplary of such antibodies are described in Stemberget et al. (2102) PLoS One, 7:35798 and International PCT Application No. WO2013/011011.

In some embodiments, the antibody specifically binding a cell surface marker associated with or coated on a bead or other surface is a full-length antibody or is an antigen-binding fragment thereof, including a (Fab) fragments, F(ab')$_2$ fragments, Fab' fragments, Fv fragments, variable heavy chain (V$_H$) regions capable of specifically binding the antigen, single chain antibody fragments, including single chain variable fragments (scFv), and single domain antibodies (e.g., sdAb, sdFv, nanobody) fragments. In some embodiments, the antibody is a Fab fragment. In some embodiments, the antibody can be monovalent, bivalent or multivalent. In some embodiments, the antibody, such as a Fab, is a multimer. In some embodiments, the antibody, such as a Fab multimer, forms a multivalent complex with the cell surface marker.

In some embodiments, the antibody, such as a Fab, associated with a Streptamer exhibits a particular kinetic measure of binding affinity (e.g. dissociation constant, K$_D$, association constant K$_A$, off-rate or other kinetic parameter of binding affinity). Such measurements can be determined using any binding assay known to a skilled artisan. In particular examples, an affinity-based biosensor technology is utilized as a measure of binding affinity. Exemplary biosensor technologies include, for example, Biacore technologies, BioRad ProteOn, Reichert, GWC Technologies, IBIS SPIR Imaging, Nomadics SensiQ, Akubio RAPid, ForteBio Octet, IAsys, Nanofilm and others (see e.g. Rich et al. (2009) Analytical Biochemistry, 386:194-216). In some embodiments, binding affinity is determined by fluorescence titration or titration calorimetry.

In some embodiments, the antibody, such as a Fab, exhibits a $k_{off}$-rate (also called dissociation rate constant) for the binding to a cell surface marker on a cell that is greater than about $0.5 \times 10^{-4}$ sec$^{-1}$, about $1 \times 10^{-4}$ sec$^{-1}$, about $2 \times 10^{-4}$ sec$^{-1}$, about $3 \times 10^{-4}$ sec$^{-1}$, about $4 \times 10^{-4}$ sec$^{-1}$, about $5 \times 10^{-4}$ sec$^{-1}$, about $1 \times 10^{-3}$ sec$^{-1}$, about $1.5 \times 10^{-3}$ sec$^{-1}$, about $2 \times 10^{-3}$ sec$^{-1}$, about $3 \times 10^{-3}$ sec$^{-1}$, about $4 \times 10^{-3}$ sec$^{-1}$, about $5 \times 10^{-3}$ sec$^{-1}$, about $1 \times 10^{-2}$ sec$^{-1}$, or about $5 \times 10^{-1}$ sec$^{-1}$ or greater. The particular $k_{off}$ rate can determine the rate at which the antibody reagent can dissociate from the its interaction with a cell via its binding to a cell surface marker (see e.g. International Published PCT Appl. No. WO/2013011011). For example, in some aspects, the $k_{off}$ range can be chosen within a range, depending, for example, on the particular application or use of a selected or enriched cell, including factors such as the desire to remove the bound antibody from the cell surface, the time of the cells in culture or incubation, the sensitivity to the cell and other factors. In one embodiment, an antibody has a high $k_{off}$ rate of, for example, greater than $4.0 \times 10^{-4}$ sec$^{-1}$, so that, after the disruption of the multivalent binding complexes, most of the antibody can be removed within one hour, since, in some aspects taking into account the half-life T1/2 of the complex, within 56 minutes the concentration of the complexes is reduced to 25% of the original concentration, assuming that rebinding effects can be neglected due to sufficient dilution). In another embodiment, an antibody with a lower k0ff rate of, for example, $1.0 \times 10^{-4}$ sec$^{-1}$, the dissociation may take longer, for example about or approximately 212 min or about 3 and a half hours to remove 75% of the antibody from the surface.

In some embodiments, the antibody, such as a Fab, exhibits a dissociation constant (Ka) for the binding to a cell surface marker on a cell that can be the range of about $10^{-2}$ M to about $10^{-8}$ M, or of about $10^{-2}$ M to about $10^{-9}$ M, or of about $10^{-2}$ M to about $0.8 \times 10^{-9}$ M, or of about $10^{-2}$ M to about $0.6 \times 10^{-9}$ M, or of about $10^{-2}$ M to about $0.4 \times 10^{-9}$ M, or of about $10^{-2}$ M to about $0.3 \times 10^{-9}$ M, or of about $10^{-2}$ M to about $0.2 \times 10^{-9}$, or of about $10^{-2}$ M to about $0.15 \times 10^{-9}$ M, or of about $10^{-2}$ to about $10^{-10}$, In some embodiments, the dissociation constant (Ka) for the binding a cell surface marker on a cell can be in the range of about $10^{-7}$ M to about $10^{-10}$ M, or of about $10^{-7}$ M to about $0.8 \times 10^{-9}$ M, or of about $10^{-7}$ M to about $0.6 \times 10^{-9}$ M, of about $10^{-7}$ M to about $0.3 \times 10^{-9}$ M, of $1.1 \times 10^{-7}$ M to about $10^{-10}$ M, or of about $1.1 \times 10^{-7}$ M to about $0.15 \times 10^{-9}$ M, or of about $1.1 \times 10^{-7}$ M to about $0.3 \times 10^{-9}$ M, or of about $1.1 \times 10^{-7}$ M to about $0.6 \times 10^{-9}$ M, or of about $1.1 \times 10^{-7}$ M to about $0.8 \times 10^{-9}$ M.

In some embodiments, the immunoaffinity reagent, such as antibody, for example a Fab, is linked, directly or indirectly, to a peptide ligand, such as a peptide ligand capable of binding to a streptavidin mutant (see e.g. U.S. Pat. No. 5,506,121). In some embodiments, such as peptide contains the sequence of amino acids set forth in any of SEQ ID NOS:1-6. In some embodiments, the immunoaffinity reagent, such as antibody, for example a Fab, is linked, directly or indirectly, to a peptide ligand containing the sequence of amino acids set forth in SEQ ID NO:6.

In some embodiments, the immunoaffinity reagent, such as antibody, for example a Fab, is fused directly or indirectly with a peptide sequence that contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa (SEQ ID NO:1), where Xaa is glutamine, asparagine, or methionine, and wherein the other binding module has the sequence of the same or different streptavidin peptide ligand, such as set forth in SEQ ID NO:3 (see e.g. International Published PCT Appl. No. WO02/077018; U.S. Pat. No. 7,981,632). In some embodiments, the peptide ligand fused, directly or indirectly, to the immunoaffinity reagent, such as antibody, for example Fab, contains a sequence having the formula set forth in any of SEQ ID NO: 7 or 8. In some embodiments, the peptide ligand has the sequence of amino acids set forth in any of SEQ ID NOS: 9, 10 or 17-19.

Alternatively, other streptavidin-binding peptides known in the art may be used, e.g. as described by Wilson et al. (Proc. Natl. Acad. Sci. USA 98 (2001), 3750-3755). In some embodiments, the peptide is fused to the N- and/or C-terminus of the protein.

In some embodiments, the antibody, such as a Fab, fused to a peptide ligand capable of binding a streptavidin mutant, is contacted with streptavidin-mutant containing beads to coat the beads with antibody. In some embodiments, the coated beads can be used in enrichment and selection methods as described herein by contacting such beads with a sample containing cells to be enriched or selected.

In some embodiments, the bond between the peptide ligand binding partner and streptavidin mutein binding reagent is reversible. In some embodiments, the bond between the peptide ligand binding partner and streptavidin mutein binding reagent is high, such as described above, but is less than the binding affinity of the streptavidin binding reagent for biotin or a biotin analog. Hence, in some embodiments, biotin (Vitamin H) or a biotin analog can be added to compete for binding to disrupt the binding interaction between the streptavidin mutein binding reagent on the bead and the peptide ligand binding partner associated with the antibody specifically bound to a cell marker on the surface. In some embodiments, the interaction can be reversed in the presence of low concentrations of biotin or analog, such as in the presence of 0.1 mM to 10 mM, 0.5 mM to 5 mM or 1 mM to 3 mM, such as generally at least or about at least 1 mM or at least 2 mM, for example at or about 2.5 mM. In some embodiments, incubation in the presence of a competing agent, such as a biotin or biotin analog, releases the bead from the selected cell.

b. Immunoaffinity Chromatography

In some embodiments, the affinity-based selection employs immunoaffinity chromatography. Immunoaffinity chromatography methods include, in some aspects, one or more chromatography matrix as described in U.S. Published Patent Appl. No. US2015/0024411. In some embodiments, the chromatographic method is a fluid chromatography, typically a liquid chromatography. In some embodiments, the chromatography can be carried out in a flow through mode in which a fluid sample containing the cells to be isolated is applied, for example, by gravity flow or by a pump on one end of a column containing the chromatography matrix and in which the fluid sample exits the column at the other end of the column. In addition, in some aspects, the chromatography can be carried out in an "up and down" mode in which a fluid sample containing the cells to be isolated is applied, for example, by a pipette on one end of a column containing the chromatography matrix packed within a pipette tip and in which the fluid sample enters and exits the chromatography matrix/pipette tip at the other end of the column. In some embodiments, the chromatography can also be carried out in a batch mode in which the chromatography material (stationary phase) is incubated with the sample that contains the cells, for example, under shaking, rotating or repeated contacting and removal of the fluid sample, for example, by means of a pipette.

In some embodiments, the chromatography matrix is a stationary phase. In some embodiments, the chromatography is column chromatography. In some embodiments, any suitable chromatography material can be used. In some embodiments, the chromatography matrix has the form of a solid or semi-solid phase. In some embodiments, the chromatography matrix can include a polymeric resin or a metal oxide or a metalloid oxide. In some embodiments, the chromatography matrix is a non-magnetic material or non-magnetizable material. In some embodiments, the chromatography matrix is a derivatized silica or a crosslinked gel, such as in the form of a natural polymer, for example a polysaccharide. In some embodiments, the chromatography matrix is an agarose gel. Agarose gel for use in a chromatography matrix are known in the art and include, in some aspects, Superflow™ agarose or a Sepharose material such as Superflow™ Sepharose®, which are commercially available in different bead and pore sizes. In some embodiments, the chromatography matrix is a particular cross-linked agarose matrix to which dextran is covalently bonded, such as any known in the art, for example in some aspects, Sephadex®, Superdex® or Sephacryl®, which are available in different bead and pore sizes.

In some embodiments, a chromatography matrix is made of a synthetic polymer, such as polyacrylamide, a styrene-divinylbenzene gel, a copolymer of an acrylate and a diol or of an acrylamide and a diol, a co-polymer of a polysaccha-rdie and agarose, e.g. a polyacrylamide/agarose composite, a polysaccharide and N, N'-methylenebiscarylamide, or a derivatized silica coupled to a synthetic or natural polymer.

In some embodiments, the chromatography matrix, such as agarose beads or other matrix, has a size of at least or about at least 50 µm, 60 µm, 70 µm, 80 µm, 90 µm, 100 µm, 120 µm or 150 µm or more. The exclusion limit of the size exclusion chromatography matrix is selected to be below the maximal width of the target cell in a sample, e.g. T cells. In some embodiments, the volume of the matrix is at least 0.5 mL, 1 mL, 1.5 mL, 2 mL, 3 mL, 4 mL, 5 mL, 6 mL, 7 mL, 8 mL, 9 mL, 10 mL or more. In some embodiments, the chromatography matrix is packed into a column.

In some embodiments, the chromatography matrix, which is an immunoaffinity chromatography matrix, includes an affinity reagent, such as an antibody or antigen-binding fragment, such as Fab, immobilized thereto. The antibody or antigen-binding fragment, such as a Fab, can be any as described above, including, in some aspects, known antibodies in the art, antibodies having a particular $k_{off}$ rate and/or antibodies having a particular dissociation constant (Ka).

In some embodiments, the affinity reagent, such as antibody or antigen-binding fragment, such as a Fab, is immobilized. In some embodiments, the immunoaffinity reagent, such as an antibody or antigen-binding fragment, such as a Fab, is fused or linked to a binding partner that interacts with a binding reagent immobilized on the matrix. In some embodiments, the binding capacity of the chromatography matrix is sufficient to adsorb or is capable of adsorbing at least $1\times10^7$ cells/mL, $5\times10^7$ cells/mL, $1\times10^8$ cells/mL, $5\times10^8$ cells/mL, $1\times10^9$ cells/ml or more, in which said cells are cells expressing a cell surface marker specifically recognized by the affinity reagent, such as antibody or Fab.

In some embodiments, the interaction between the binding reagent and binding partner forms a reversible bond, so that binding of the antibody to the matrix is reversible. In some embodiments, the reversible binding can be mediated by a streptavidin mutant binding partner and a binding reagent immobilized on the matrix that is streptavidin, a streptavidin analog or mutein, avidin or an avidin analog or mutein.

In some embodiments, reversible binding of the affinity reagent, such as antibody or antigen-binding fragment, such as Fab is via a peptide ligand binding reagent and streptavidin mutein interaction, as described above with respect to immunoaffinity beads. In aspects of the chromatography matrix, the matrix, such as agarose beads or other matrix, is functionalized or conjugated with a streptavidin mutein, such as any described above, for example any set forth in SEQ ID NOS: 12, 13, 15 or 16. In some embodiments, the antibody or antigen-binding fragment, such as a Fab, is fused or linked, directly or indirectly, to a peptide ligand capable of binding to a streptavidin mutant, such as any described above. In some embodiments, the peptide ligand is any as described above, such as a peptide containing the sequence of amino acids set forth in any of SEQ ID NOS:1-10 or 17-19. In some embodiments, the chromatography matrix column is contacted with such an affinity reagent, such as an antibody or antigen-binding fragment, such as a Fab to immobilize or reversibly bind the affinity reagent to the column.

In some embodiments, the immunoaffinity chromatography matrix can be used in enrichment and selection methods as described herein by contacting said matrix with a sample containing cells to be enriched or selected. In some embodiments, the selected cells are eluted or released from the matrix by disrupting the interaction of the binding partner/binding reagent. In some embodiments, binding partner/binding reagents is mediated by a peptide ligand and streptavidin mutein interaction, and the release or selected cells can be effected due to the presence of a reversible bond. For example, in some embodiments, the bond between the peptide ligand binding partner and streptavidin mutein binding reagent is high, such as described above, but is less than the binding affinity of the streptavidin binding reagent for biotin or a biotin analog. Hence, in some embodiments, biotin (Vitamin H) or a biotin analog can be added to compete for binding to disrupt the binding interaction between the streptavidin mutein binding reagent on the matrix and the peptide ligand binding partner associated with the antibody specifically bound to a cell marker on the surface. In some embodiments, the interaction can be reversed in the presence of low concentrations of biotin or analog, such as in the presence of 0.1 mM to 10 mM, 0.5 mM to 5 mM or 1 mM to 3 mM, such as generally at least or about at least 1 mM or at least 2 mM, for example at or about 2.5 mM. In some embodiments, elution in the presence of a competing agent, such as a biotin or biotin analog, releases the selected cell from the matrix.

In some embodiments, immunoaffinity chromatography in the provided methods is performed using at least two chromatography matrix columns that are operably connected, whereby an affinity or binding agent to one of CD4 or CD8, such as an antibody, e.g. a Fab, is coupled to a first chromatography matrix in a first selection column and an affinity or binding agent to the other of CD4 or CD8, such as an antibody, e.g. a Fab, is coupled to a second chromatography matrix in a second selection column. In some embodiments, the at least two chromatography matrix columns are present in a closed system or apparatus, such as a closed system or apparatus that is sterile.

In some embodiments, also provided herein is a closed system or apparatus containing at least two chromatography matrix columns that are operably connected, whereby an affinity or binding agent to one of CD4 or CD8, such as an antibody, e.g. a Fab, is coupled to a first chromatography matrix in a first selection column and an affinity or binding agent to the other of CD4 or CD8, such as an antibody, e.g. a Fab, is coupled to a second chromatography matrix in a second selection column. Exemplary of such systems and methods are depicted in FIG. 1A an FIG. 1B, and in Examples.

In some embodiments, the closed system is automated. In some embodiments, components associated with the system can include an integrated microcomputer, peristaltic pump, and various valves, such as pinch valves or stop cocks, to control flow of fluid between the various parts of the system. The integrated computer in some aspects controls all components of the instrument and directs the system to perform repeated procedures in a standardized sequence. In some embodiments, the peristaltic pump controls the flow rate throughout the tubing set and, together with the pinch valves, ensures the controlled flow of buffer through the system.

With reference to FIG. 1A and FIG. 1B, in some embodiments, the first affinity matrix 3 containing a first affinity or binding agent in a first selection column 1 is i) operably coupled to the second affinity matrix 4 containing a second affinity or binding agent in a second selection column 2 via tubing and a valve 13 so that cells having passed through the first affinity chromatography matrix and not being bound to a first affinity or binding agent thereon are capable of being passed into the second affinity matrix and ii) is operably coupled to an output container, such as a culture vessel 12, to collect selected cells from the first affinity matrix that bound to the first affinity or binding agent thereon, such as after elution and release of such cells from the first affinity matrix. In some embodiments, the second affinity matrix 4 containing a second affinity or binding agent in a second selection column 2 also is operably coupled to the output container, such as a culture vessel 12, to collect selected cells from the second affinity matrix that bound to the second affinity or binding agent thereon, such as after elution and release of such cells from the second affinity matrix. In some embodiments, the second selection column 2 is operably connected to the output container, such as culture vessel 12, through a removal chamber 9 that contains a binding reagent, such as a streptavidin mutant, that is able to bind with high affinity, such as greater than $10^{-10}$ M$^{-1}$, to an elution reagent, such as biotin.

In some embodiments, the size, e.g. length and/or diameter, of the first selection column 1 and second selection column 2 can be the same or different. In some embodiments, the size, e.g. length and/or diameter, of one of the first column 1 or second column 2 is larger than the size of the other of the columns by at least 1.2 times, 1.5 times, 2 times, 3 times, 4 times, 5 times, 5 times, 7 times, 8 times, 9 times, 10 times or more.

In some embodiments, the first affinity matrix 3 containing a first affinity or binding agent in a first selection column 1 also is operably connected to a third affinity matrix 17 containing a third affinity or binding agent in a third selection column 15 via tubing and a valve 13, so that selected cells from the first affinity matrix that bound to the first affinity or binding agent thereon are capable of being passed into the third affinity matrix, such as after elution and release of such cells from the first affinity matrix. In some embodiments, the first selection column 1 is operably connected to the third selection column 15 through a removal chamber 9 that contains a binding reagent, such as a streptavidin mutant, that is able to bind with high affinity, such as greater than $10^{-10}$ M$^{-1}$, to an elution reagent, such as biotin. In some embodiments, the third affinity matrix 17 containing a third affinity or binding agent in a third selection column 15 also is operably coupled to the output container, such as a culture vessel 12, to collect selected cells from the third affinity matrix having bound to the third affinity or binding agent thereon (and previously having bound to the first affinity or binding agent), such as after elution and release of such cells from the third affinity matrix (and previously from the first affinity matrix). In some embodiments, the third selection column 15 is operably connected to the output container, such as culture vessel 12, through a removal chamber 9 that contains a binding reagent, such as a streptavidin mutant, that is able to bind with high affinity, such as greater than $10^{-10}$ M$^{-1}$, to an elution reagent, such as biotin.

In some embodiments, the size, e.g. length and/or diameter, of the first selection column 1 and third selection column 15 can be the same or different. In some embodiments, the size, e.g. length and/or diameter, of one of the first column 1 or third column 15 is larger than the size of the other of the columns by at least 1.2 times, 1.5 times, 2 times, 3 times, 4 times, 5 times, 5 times, 7 times, 8 times, 9 times, 10 times or more.

In some embodiments, the first selection column 1 is operably coupled to a storage reservoir containing cell sample 5, such as via tubing, valves and a pump 8, in order to provide a cell sample into the first selection column.

In some embodiments, the first selection column 1 also is operably coupled to a washing reservoir 6 containing wash buffer and/or an elution reservoir 7 containing an eluent, such as through tubing and valves, in order to permit passage of a washing buffer or an elution buffer, respectively, into the first chromatography matrix in the first selection column. In some embodiments, due to the operable connection between the first and second selection column, the washing buffer and/or elution buffer can operably pass through into the second column. In some embodiments, due to the operable connection between the first and third selection column, the washing buffer and/or elution buffer can operably pass through into the third selection column.

In some embodiments, the second selection column 2 also is operably coupled to a washing reservoir 6 containing wash buffer and/or an elution reservoir 7 containing an eluent, such as through tubing and valves, in order to permit passage of a washing buffer or an elution buffer, respectively, into the first chromatography matrix in the first selection column.

The washing buffer can be any physiological buffer that is compatible with cells, such as phosphate buffered saline. In some embodiments, the washing buffer contains bovine serum albumin, human serum albumin, or recombinant human serum albumin, such as at a concentration of 0.1% to 5% or 0.2% to 1%, such as or at about 0.5%. In some embodiments, the eluent is biotin or a biotin analog, such as desbiotin, for example in an amount that is or is about at least 0.5 mM, 1 mM, 1.5 mM, 2 mM, 2.5 mM, 3 mM, 4 mM, or 5 mM.

In some embodiments, the first affinity matrix 3 in the first selection column 1 is operably connected through tubing and valves to a first affinity reagent reservoir (e.g. Fab reservoir) 18 containing the first affinity or binding agent, such as an antibody, e.g. a Fab, such as for immobilization onto the first affinity matrix. In some embodiments, the second affinity matrix 4 in the second column 2 is operably connected through tubing and valves to a second affinity or binding agent reservoir (e.g. Fab reservoir) 19 containing the second affinity or binding agent, such as an antibody, e.g. a Fab, such as for immobilization onto the second affinity matrix. In some embodiments, the third affinity matrix 17 in the third selection column 15 is operably connected through tubing and valves to a third affinity or binding agent reservoir (e.g. Fab reservoir) 20 containing the third affinity or binding agent, such as an antibody, e.g. a Fab, such as for immobilization onto the second affinity matrix.

In some embodiments, the first and/or second affinity reagent specifically binds CD4 or CD8, where the first and second affinity reagent are not the same. In some embodiments, the third affinity reagent specifically binds a marker on naïve, resting or central memory T cells or specifically binds a marker that is CD45RO, CD62L, CCR7, CD28, CD3, CD27 and/or CD127.

5. Enrichments and Ratios of Generated Compositions

In some embodiments, performing a first and second selection using methods as described above enriches from a sample a first population of cells expressing a first cell surface marker and a second population of cells expressing a second cell surface marker, respectively. In particular examples, the first and/or second population of enriched cells can be a population of cells enriched for CD4$^+$ cells, and the other of the enriched population of cells, i.e. the other of the first or second population of cells, can be a population enriched for CD8$^+$. As described above, in some embodiment, a third, fourth or subsequent selection can be performed to enrich for a further sub-population of cells from a population of cells previously enriched in the first, second or subsequent enrichments, such as a sub-population of CD4$^+$ cells and/or a sub-population of CD8$^+$ cells.

In some embodiments, the method produces an enriched composition of cells containing the first and second population of enriched cells, such as a population of cells enriched for CD4+ cells and a population of cells enriched for CD8+ cells. In some embodiments, the enriched composition of cells is designated a culture initiation composition and is used in subsequent processing steps, such as subsequent processing steps involving incubation, stimulation, activation, engineering and/or formulation of the enriched cells. In some embodiments, subsequent to the further processing steps, such as processing steps involving incubation, stimulation, activation, engineering and/or formulation, and output composition is generated that, in some aspects, can contain genetically engineered cells containing CD4+ cells and CD8+ cells expressing a genetically engineered antigen receptor.

In some embodiments, the enriched compositions of cells are enriched cells from a starting sample as describe above, in which the number of cells in the starting sample is at least greater than the desired number of cells in an enriched composition, such as a culture-initiation composition. In some embodiments, the number of cells in the starting sample is greater by at least 10%, 20%, 30%, 40%, 50%, 60%, 70%, 80%, 90%, 100%, 500%, 1000%, 5000% or more greater than the desired number of cells in the enriched composition. In some examples, the desired number of cells in the enriched population, including enriched CD4+ cells, CD8+ cells or sub-populations thereof, is at least $1\times10^6$ cells, $2\times10^6$ cells, $4\times10^6$ cells, $6\times10^6$ cells $8\times10^6$ cells, $1\times10^7$ cells, $2\times10^7$ cells, $4\times10^7$ cells, $6\times10^7$ cells, $8\times10^7$ cell, $1\times10^8$ cells, $2\times10^8$ cells, $4\times10^8$ cells, $6\times10^8$ cells, $8\times10^8$ cells, $1\times10^9$ cells or greater. In some embodiments, the number of cells in the starting sample, is at least $1\times10^8$ cells, $5\times10^8$ cells, $1\times10^9$ cells, $2\times10^9$ cells, $3\times10^9$ cells, $4\times10^9$ cells, $5\times10^9$ cells, $6\times10^9$ cells, $7\times10^9$ cells, $8\times10^9$ cells, $9\times10^9$ cells, $1\times10^{10}$ cells or more.

In some embodiments, the yield of the first and/or second population or sub-population thereof, in the enriched composition, i.e. the number of enriched cells in the population or sub-population compared to the number of the same population or sub-population of cells in the starting sample, is 10% to 100%, such as 20% to 80%, 20% to 60%, 20% to 40%, 40% to 80%, 40% to 60%, or 60%, to 80%. In some embodiments, the yield of the first and/or second population of cells or sub-population thereof is less than 70%, less than 60%, less than 50%, less than 40%, less than 30% or less than 20%.

In some embodiments, the purity of the first and/or second population of cells or sub-population of cells thereof in the enriched composition, i.e. the percentage of cells positive for the selected cell surface marker versus total cells in the population of enriched cells, is at least 90%, 91%, 92%, 93%, 94%, and is generally at least 95%, 96%, 97%, 98%, 99% or greater.

In some embodiments, the enriched composition of cells, such as a culture-initiation composition, contains a ratio of CD4+ cells to CD8+ cells at a culture-initiation ratio. The culture-initiation ratio is the ratio or number of cells at which two types of cells or isolated cell populations are included in a culture-initiating composition, designed to result in the desired output ratio or dose, e.g., ratio or dose for administration to a patient, or within a tolerated error rate or difference thereof, at the completion of the incubation and/or engineering step or other processing steps and/or upon thaw and/or just prior to administration to a subject. In embodiments of the methods provided herein, the first and/or second selections, or selections for sub-populations thereof, can be performed in a manner to result in a chosen culture-initiation ratio. Exemplary of such methods are described below and in Examples.

a. Culture-Initiation Ratios and Numbers

In some embodiments, the culture-initiating ratio of CD4$^+$ or sub-populations thereof to CD8$^+$ cells or sub-populations thereof is between at or about 10:1 and at or about 1:10, between at or about 5:1 and at or about 1:5, or between at or about 2:1 and at or about 1:2. In some embodiments, the culture-initiating ratio of CD4+ cells or sub-populations thereof to CD8+ cells or sub-populations thereof is at or about 1:1.

In some embodiments, the culture-initiating ratio of CD4+ to CD8+ cells, or sub-populations thereof, is different than the ratio of CD4+ to CD8+ cells or the sub-populations thereof in the sample from the subject. In some embodiments, it is reported that the ratio of CD4+ to CD8+ T cells in a sample from subjects, such as a blood sample, is between 1:1 and 14:1 CD4+:CD8+ cells, and generally is between about 1.5:1 and about 2.5:1 CD4+:CD8+ cells. In some embodiments, the ratio of CD4+ to CD8+ T cells in a sample, such as a blood sample, is about 2:1 CD4+:CD8+ cells In some embodiments, the ratio of CD4+ to CD8+ T cells in a sample, such as a blood sample, is about 1:1. (See e.g. Amadori, A et al., *Nature Med.* 1: 1279-1283, 1995; Chakravarti, A., *Nature Med.* 1: 1240-1241, 1995; Clementi, M., et al., *Hum. Genet.* 105: 337-342, 1999.) In some embodiments, a subject ratio is less than 1:1 CD4+:CD8+ cells. (See e.g. Muhonen, T. *J Immunother Emphasis Tumor Immunol.* 1994 January; 15(1):67-73). In some embodiments, the culture-initiating ratio of CD4+ to CD8+ cells is at least 10%, at least 20%, at least 30%, at least 40%, at least 50%, at least 60%, at least 70%, at least 80%, at least 90%, at least 100%, at least 125%, at least 150, at least 200%, at least 300%, at least 400%, or at least 500% greater or less than the ratio of CD4+ to CD8+ cells in the sample from the subject.

In some embodiments, prior to performing the first and/or second selection, the ratio of CD4+ to CD8+ T cells in the sample from the subject is determined. Based on the particular ratio of the CD4+ to CD8+ T cells in the subject, which can vary among subject, the particular mode of selection can be individualized to the subject, for example by sizing of chromatography columns or selection of amount or concentration of immunoaffinity reagents, to achieve the desired or chosen culture-initiating ratio. The relative level or frequency of various cell populations in a subject can be determined based on assessing surface expression of a marker or markers present on such populations or sub-populations. A number of well-known methods for assessing expression level of surface markers or proteins may be used, such as detection by affinity-based methods, e.g., immuno-affinity-based methods, e.g., in the context of cell surface proteins, such as by flow cytometry.

In some contexts, the appropriate culture-initiating ratio for particular cell types can vary depending on context, e.g., for example, for a particular disease, condition, or prior treatment of a subject from which cells are derived, and/or a particular antigen-specificity of the cells, relative representation among cells of a particular type (e.g., $CD8^+$ T cells) of various subpopulations, e.g., effector versus memory versus naïve cells, and/or one or more conditions under which cells will be incubated, such as medium, stimulating agents, time of culture, buffers, oxygen content carbon dioxide content, antigen, cytokine, antibodies, and other components. Thus, it may be that a cell type which typically or in general is known to proliferate or expand more rapidly than another will not always have such a property in every context. Thus, in some aspects, the culture-initiation ratio is determined based on known capacities of cell types in a normal or typical context, coupled with assessment of phenotypes or states of the cells or subject from which the cells are derived, and/or empirical evidence.

In some embodiments, the culture-initiation ratios are based on knowledge of one or more of these features for a particular type of cell known or determined to be in the concentration. In some embodiments, the ratio of $CD4^+$ to $CD8^+$ cells in the culture-initiating composition is greater than or less than 1.5 times, 2, times, 3 times, 4 times, 5 times, 6 times, 7 times, 8 times, 9 times, 10 times, 20 times, 30 times, 40 times, 50 times, 60 times, 70 times, 80 times, 90 times more or less, respectively, than the desired output ratio of $CD4^+$ to $CD8^+$.

In some embodiments, for example, CD4+ cells in some contexts are known to proliferate or expand to a lesser degree or less rapidly compared with CD8+ cells, when incubated under certain stimulating conditions. See, e.g., Foulds et al. (2002) *J Immunol.* 168(4): 1528-1532; Caggiari et al. (2001) *Cytometry.* 46(4) 233-237; Hoffman, et al. (2002) *Transplantation.* 74(6): 836-845; and Rabenstein et al. (2014) *J Immunol.* Published online before print Mar. 17, 2014, doi: 10,4049/jimminol.1302725. Thus, in some examples, the ratio of $CD4^+$ to $CD8^+$ cells in the culture-initiating composition is 10 times or 100 times the desired output ratio. For example, if a 1:1 (or 50%/50%) CD4/CD8 output ratio is desired, the $CD4^+$ and $CD8^+$ populations may in one example be included in the culture-initiating composition at a ratio of 2:1, 3:1, 4:1, 5:1, 6:1, 7:1, 8:1, 9:1, 10:1, 20:1, 30:1, 40:1, 50:1, 60:1, 70:1, 80:1, 90:1, or 100:1, for example, to account for differences in expansion rates over a particular period of time. Depending on the differences in rates or expansion or proliferation of one of the CD4+ or CD8+ cells, or sub-populations thereof, from the other, a skilled artisan can empirically determine the culture-initiation ratio to achieve a desired output ratio following under particular conditions of stimulation or activation.

The culture-initiation ratio will not necessarily be identical, or even approximate, the desired output ratio. For example, if it is desired to administer $CD4^+$ and $CD8^+$ engineered (e.g., CAR-expressing) T cells at or within a certain error of 1:1, the culture-initiation ratio of $CD4^+$ and $CD8^+$ cells often is not 1:1. In some embodiments, the culture initiation ratio that results in the desired output ratio varies depending, e.g., on the source of the cells, the cell types to be cultured, the patient to whom the cells are to be administered, the subject or subjects from whom the cells have been isolated or derived, such as what diseases or conditions such a subject has, the disease to be treated, culture conditions, and other parameters.

In some embodiments, the culture initiation ratio is based on the composition of each subpopulation of cells. In certain embodiments, the culture initiation ratio is based on the length of time the populations of cells are culture prior to their being genetically engineered. In some embodiments, the culture initiation ratio is based on the proliferation rate of each population of cells.

As another aspect, in some embodiments, the methods further include determining a culture-initiation ratio or number. In some embodiments, the provided methods include methods and steps for determining appropriate ratios, doses, and numbers of cells, cell types, and populations of cells. For example, provided are methods for determining ratios of $CD4^+/CD8^+$ cells, populations, and/or sub-populations and determining appropriate doses of such cells and sub-types. In some embodiments, provided are methods for determining appropriate ratios or numbers of cell types or cell populations to be included in a composition, such as a culture-initiating composition, to achieve a desired outcome. In some aspects, such ratios or numbers are designed for use in an incubation or engineering step to achieve a desired output ratio or dose. In some embodiments, provided are methods for determining desired ratio of the cells, types, or populations, and/or cell numbers thereof, for administration to a subject or patient.

In some embodiments, the chosen culture initiation ratio is based on the relative capacity of the different cell types or populations for survival and/or proliferation or expansion rate of each population of cells or type of cell (such as $CD4^+$ versus $CD8^+$ cells) in culture when incubated under such conditions. Thus, in some aspects, proliferation rate, survival, and/or output ratios are measured or assessed following test incubations, for example, at particular point or points in time following incubation, and/or following a cryopreservation or freeze step and/or following a thaw after such procedure, such as just prior to administration, e.g., at the bedside, in order to determine the optimal ratios for culture initiation. Any of a number of well-known methods for determination of in vitro or ex vivo cell proliferation rates or survival include flow-cytometry methods such as labeling with carboxyfluorescein diacetate succinimidyl ester (CFSE) or similar fluorescent dye prior to incubation, followed by assessment of fluorescent intensity by flow cytometry, and/or assessment of binding of cells to Annexin V or other compound recognizing markers on or in apoptotic cells and/or uptake of DNA interchelating agents such propidium iodide or 7AAD, and assessment of uptake and/or cell cycle stages as a measure of proliferation or apoptosis by flow cytometry.

In some embodiments, the culture-initiation ratio is determined by incubating two isolated populations, e.g., sub-populations, of cells at a range of different ratios in test compositions, under certain test conditions, and assessing one or more outcomes, such as the output ratio achieved after a certain period. In some aspects, the conditions are stimulatory conditions, such as those approximating conditions under which the culture-initiating compositions are to be incubated for culture and/or engineering steps. For example, the test compositions in some aspects are administered in the presence of one or more, e.g., each, of the same stimulating agents, media, buffers, gas content, and/or in the same type of container or vessel, and/or for the same or approximately the same amount of time as the parameters to be used in the incubation and/or engineering steps that are to be used in preparing or producing the ultimate composition, such as the engineered composition for administration.

Exemplary test ratios for the test culture-initiating compositions can include at or about 90%/10%, 80%/20%, 70%/30%, 60%/40%, 50%/50%, 40%/60%, 30%/70%, 20%/80%, and 10%/90%, or 0.1:1, 0.5:1, 0.7:1, 0.8:1, 0.9:1, 1:1, 1:1.1, 1:1.2, 1:1.3, 1:1.4, 1:1.5, or more than at or about 1:1.5, or at or about 1:0.1, 1:0.4, 1:0.7, 1:0.8, 1:0.8, 1.1:1, 1.2:1, 1.3:1, 1.4:1, or 1.5; 1, or more.

In some contexts, the appropriate culture-initiation ratio of $CD4^+$ versus $CD8^+$ cells to achieve a desired CD4:CD8 ratio at the end of production is determined based on the sub-population of the $CD4^+$ and/or $CD8^+$ fractions in a particular isolated cell product, such as the presence and/or percentage of naïve, effector, and various memory compartments are represented in a particular isolated composition. Such assessment can be by determining the presence or level of various surface markers on the cells, such as by flow cytometry.

In some embodiments, the culture initiation ratio is based on the phenotype of each population of cells. In certain embodiments, the culture initiation ratio is based on the culture conditions (e.g., such as the composition of the media, the presence and/or absence of growth factors, stimulants, and/or other agents, temperature, aeration conditions, etc.).

In some embodiments of the methods described herein, the culture initiation ratio produces an output composition that comprises a ratio of $CD4^+$:$CD8^+$ cells or a number of such sub-types or total cell number that is within about 10%, about 15%, about 20%, about 25%, about 30% about 35%, about 40%, about 45% or about 50% of the desired ratio or dose, including any range in between these values. In some embodiments of the methods described herein, the culture initiation ratio produces an output composition having the desired ratio of $CD4^+$:$CD8^+$ cells or dose of such cells at least 50%, at least 55%, at least 60%, at least 65%, at least 70%, at least 75%, at least 80%, at least 85%, at least 90%, at least 95%, or more than 95% of the time, including any range between these values. In certain embodiments of the methods, the culture initiation ratio produces a ratio of $CD4^+$ to $CD8^+$ cells in the output composition that is within 20% of the desired output ratio at least 80% of the time. In some embodiments of the methods described herein, the output composition comprises a ratio of $CD4^+$ to $CD8^+$ cells that is within a tolerated difference of the desired output ratio, said tolerated difference having been determined as described above, e.g., by administering $CD4^+$ and $CD8^+$ cells to one or more subjects at a plurality of ratios.

b. Output Ratios and Doses

In some embodiments, the method results an output composition following one or more processing steps of the culture-initiation composition, such as incubation, stimulation, activation, engineering and/or formulation of cells. In some embodiments, the method is performed to achieve or result in a desired ratio of $CD4^+$ to $CD8^+$ cells, or sub-populations thereof, that is between at or about 2:1 and at or about 1:5, at or about 2:1 and at or about 1:2, at or about 1.5:1 and at or about 1:5, at or about 1.5:1 and at or about 1:2, or at or about 1:1 and at or about 1:2. In some embodiments, the desired output ratio of $CD4^+$ to $CD8^+$ cells in the output composition is 1:1 or is about 1:1.

In some embodiments, the method produces or generates an output composition, such as a composition containing genetically engineered $CD4^+$ T cells and $CD8^+$ T cells or sub-populations thereof, in which the output ratio of $CD4^+$ to $CD8^+$ cells in the composition, or sub-populations thereof, is between at or about 2:1 and at or about 1:5, at or about 2:1 and at or about 1:2, at or about 1.5:1 and at or about 1:5, at or about 1.5:1 and at or about 1:2, or at or about 1:1 and at or about 1:2. In some embodiments, the method produces or generates an output composition containing an output ratio of $CD4^+$ to $CD8^+$ cells that is 1:1 or is about 1:1.

In some embodiments, the output ratio of $CD4^+$ to $CD8^+$ T cells is a ratio that is desired as part of a dosage of T cells for immunotherapy, such as in connection with methods of adoptive immunotherapy.

In some embodiments, desired dosages, such as desired cell numbers and/or desired output ratios of the cell types or populations (e.g., ratios optimal for therapeutic administration to a patient), are determined. In some embodiments, the methods include steps for determining tolerated error or tolerated difference from a desired output or administration ratio or dose, i.e., the margin of error by which the ratio in a given composition, e.g., engineered composition, can vary from a desired output ratio, and still achieve a desired outcome, such as an acceptable degree of safety in a subject or patient, or efficacy in treating a particular disease or condition or other therapeutic effect.

In some embodiments, the desired dose, ratio and/or the tolerated error depends on the disease or condition to be treated, subject, source of cells, such as whether the cells are from a subject having a particular condition or disease and whether the cells are for autologous or allogeneic transplant, e.g., whether they are isolated from a subject who also is to receive the cells in adoptive cell therapy and/or whether the subject has received or is receiving another treatment and/or the identity of such treatment. In some embodiments, the ratio, number, and/or tolerated difference or error depends on one or more other property of the cells, such as proliferation rate, survival capacity, expression of particular markers or secretion of factors, such as cytokines, or particular sub-populations isolated prior to incubation and engineering steps. In some examples, the desired ratio and/or the tolerated error or difference can vary depending on the age, sex, health, and/or weight of the subject, on biomarkers as an indication of disease trait, on treatments to be co-administered or having previously been administered to the subject.

In some embodiments, the desired ratio, dose, and/or tolerated error is determined by administering various test compositions, each containing the cell types or populations of interest at different ratios or different numbers to a test subject, followed by assessment of one or more outcome or parameter, such as a parameter indicative of safety, therapeutic efficacy, in vivo concentration or localization of the cells, and/or other desired outcome.

The test subject in some embodiments is a non-human animal, such as a normal animal or an animal model for disease, such as the disease or condition to be treated by administration of the cells. In some embodiments, the various test ratios for administration to test subjects are at or about 90%/10%, 80%/20%, 70%/30%, 60/40%, 50/50%, 40/60%, 30/70%, 20%/80%, and 10%/90%, e.g., expressed as percentage of one cell type or sub-type (e.g., CD4$^+$ T cell or sub-type thereof) and another cell type (e.g., CD8$^+$ T cell or NK cell or sub-type thereof), and interim values. The ratios can be expressed as relative percentages or in any other format, such as ratios of at or about 0.1:1, 0.5:1, 0.7:1, 0.8:1, 0.9:1, 1:1, 1:1.1, 1:1.2, 1:1.3, 1:1.4, 1:1.5, or more than at or about 1:1.5, or at or about 1:0.1, 1:0.4, 1:0.7, 1:0.8, 1:0.8, 1.1:1, 1.2:1, 1.3:1, 1.4:1, or 1.5; 1, or more, including any range in between these values. In some embodiments, the test subject is a human. In some embodiments, the desired ratio is the average, mean, or median ratio among test subjects with a particular optimal effect. In some aspects, the desired ratio is a ratio that achieved some optimal balance of safety versus efficacy. In some aspects, the desired ratio or dose is a ratio or dose that achieves the highest efficacy of all test ratios or doses, while still maintaining a threshold degree of safety. In some aspects, the desired ratio or dose is a ratio or dose that achieves the highest degree of safety while maintaining a threshold degree of efficacy or within a range of efficacy. In some cases, the optimal ratio or dose is expressed as a range, such as between 1:1 and 1:2 of one cell type to another or between $10^4$ and $10^9$ or between $10^5$ and $10^6$ cells per kg body weight.

In some embodiments, the tolerated error is determined based on the deviation from the desired average test subjects are monitored to assess the therapeutic efficacy and/or safety of each percentage combination. In some embodiments, the tolerated error will be within about 1%, about 2%, about 3%, about 4% about 5%, about 10%, about 15%, about 20%, about 25%, about 30%, about 35%, about 40%, about 45%, about 50% of the desired ratio, including any value in between these ranges.

6. Exemplary Methods of Selecting or Enriching Cells a. Single Process Stream and/or Simultaneous Selection Using Immunomagnetic Beads In some embodiments, the separation and/or steps is carried out using immunomagnetic beads. In some embodiments, a cell sample containing CD4+ and CD8+ cells, such as a primary human T cell sample, is contacted with magnetic beads containing a first immunoaffinity reagent that binds to CD4 or CD8 and magnetic beads containing a second immunoaffinity reagent that binds to the other of the CD4 or CD8. The separation and/or steps can occur simultaneously and/or sequentially.

In some embodiments, contacting the cells with the magnetic beads is performed simultaneously, whereby enrichment of cells containing the surface markers CD4 and CD8 also is performed simultaneously. In some such aspects, the method includes contacting cells of a sample containing primary human T cells with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample, and recovering cells bound to the first and/or the second immunoaffinity reagent, thereby generating an enriched composition including CD4+ cells and CD8+ cells at a culture-initiating ratio.

In some embodiments, the first and/or second immunoaffinity reagent are present in the incubation composition at a sub-optimal yield concentration, whereby the enriched composition contains less than 70% of the total CD4+ cells in the incubation composition and/or less than 70% of the CD8+ cells in the incubation composition, thereby producing a composition enriched for CD4+ and CD8+ T cells.

In some embodiments, the suboptimal yield concentration of the affinity reagent is a concentration below a concentration used or required to achieve an optimal or maximal yield of bound cells in a given selection or enrichment involving incubating cells with the reagent and recovering or separating cells having bound to the reagent ("yield," for example, being the number of the cells so-recovered or selected compared to the total number of cells in the incubation that are targeted by the reagent or to which the reagent is specific or that have a marker for which the reagent is specific and capable of binding). The suboptimal yield concentration generally is a concentration or amount of the reagent that in such process or step achieves no more than 70% yield of bound cells, upon recovery of the cells having bound to the reagent. In some embodiments, no more than at or about 50%, 45%, 40%, 30%, or 25% yield is achieved by the suboptimal concentration. The concentration may be expressed in terms of number or mass of particles or surfaces per cell and/or number of mass or molecules of agent (e.g., antibody, such as antibody fragment) per cell.

For example, in some embodiments, the suboptimal yield concentration is less than at or about 30 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition. In some embodiments, the suboptimal yield concentration is less than at or about 30 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 20 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 10 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 15 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 10 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 5 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 1 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 0.5 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 0.2 M agent (e.g., antibody) per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition.

In some embodiments, the suboptimal yield concentration is less than at or about 15 mg beads, particles, surface, or total regent, per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 10 mg beads, particles, surface, or total regent, per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 5 mg beads, particles, surface, or total regent, per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 4 mg beads, particles, surface, or total regent, per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 3 mg beads, particles, surface, or total regent, per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 2 mg beads, particles, surface, or total regent, per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 1 mg beads, particles, surface, or total regent, per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition; in some embodiments, the suboptimal yield concentration is less than at or about 0.5 mg beads, particles, surface, or total regent, per $1\times10^9$, per $2\times10^9$ cells, per $3\times10^9$ cells, per $4\times10^9$ cells, per $5\times10^9$ cells, per $10\times10^9$ cells, per $15\times10^9$ cells, or per $20\times10^9$ cells in the incubation composition.

In some embodiments, e.g., when operating in a suboptimal yield concentration for each or one or more of two or more selection reagents with affinity to two or more markers or cells, one or more of such reagents is used at a concentration that is higher than one or more of the other such reagent(s), in order to bias the ratio of the cell type recognized by that reagent as compared to the cell type(s) recognized by the other(s). For example, the reagent specifically binding to the marker for which it is desired to bias the ratio may be included at a concentration (e.g., agent or mass per cells) that is increased by half, 1-fold, 2-fold, 3-fold, 4-fold, 5-fold, 10-fold, or more, compared to other(s), depending on how much it is desired to increase the ratio.

In some embodiments, employing suboptimal yield concentration to bias one or both populations of cells can achieve a desired or chosen culture-initiation ratio. In some embodiments, the selection is performed from a sample, which is a sample containing $CD4^+$ and $CD8^+$ cells, containing high numbers of cells, such as at least $1\times10^9$ cells, $2\times10^9$ cells, $3\times10^9$ cells, $4\times10^9$ cells, $5\times10^9$ cells, $6\times10^9$ cells, $7\times10^9$ cells, $8\times10^9$ cells, $1\times10^{10}$ cells, $2\times10^{10}$ cells, $3\times10^{10}$ cells, $4\times10^{10}$ cells, $5\times10^{10}$ cells or more. In some embodiments, the high number of cells is sufficient to ensure saturation of the immunoaffinity reagents in the sample to cells expressing a marker, such as CD4 or CD8, in which the reagent specifically binds.

In some embodiments, when operating in the suboptimal range and/or with enough cells to achieve saturation of reagents, the amount of immunoaffinity reagent is proportional to the approximate yield of enriched cells. In one embodiment, to achieve a culture-initiation ratio of about or approximately 1:1 of CD4+ cells to CD8+ cells, selection of CD4+ cells and CD8+ cells can be performed with the same, or about the same, suboptimal yield concentration of immunoaffinity reagents to CD4 and CD8, respectively. In another exemplary embodiment, to achieve a culture-initiation ratio of about or approximately 2:1 of CD4+ cells to CD8+ cells, selection of CD4+ cells can be performed with a suboptimal yield concentration of an immunoaffinity reagent to CD4 that is about or approximately two times greater than the suboptimal yield concentration of an immunoaffinity reagent to CD8. It is within the level of a skilled artisan to empirically select or choose an appropriate amount or concentration of immunoaffinity reagents depending on the desired or chosen culture-initiating ratio of the generated composition containing enriched or selected cells in view of the above exemplification.

In some embodiments, the separation and/or steps is carried out using magnetic beads in which immunoaffinity reagents are reversibly bound, such as via a peptide ligand interaction with a streptavidin mutein as described above. Exemplary of such magnetic beads are Streptamers®. In some embodiments, the separation and/or steps is carried out using magnetic beads, such as those commercially available from Miltenyi Biotec.

In some aspects, the separation and/or other steps is carried out for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells. In some aspects, the separation and/or other steps is carried out using CliniMACS system (Miltenyi Biotic).

In some embodiments, the automated separation, such as using the CliniMACS system, in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using a system equipped with a cell processing unit that permits automated washing and fractionation of cells by centrifugation. In some aspects, the separation and/or other steps are carried out using the CliniMACS Prodigy system (Miltenyi Biotec). A system with a cell processing unit can also include an onboard camera and image recognition software that determines the optimal cell fractionation endpoint by discerning the macroscopic layers of the source cell product. For example, peripheral blood is automatically separated into erythrocytes, white blood cells and plasma layers. A cell processing system, such as the CliniMACS Prodigy system, can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) J Immunother. 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

b. Single Process Stream and/or Sequential Selections Using Immunoaffinity Chromatography In some embodiments, the first selection or enrichment of a population of cells and the second selection and/or enrichment of a population of cells are performed using immunoaffinity-based reagents that include at least a first and second affinity chromatography matrix, respectively, having immobilized thereon an antibody. In some embodiments, one or both of the first and/or second selection can employ a plurality of affinity chromatography matrices and/or antibodies, whereby the plurality of matrices and/or antibodies employed for the same selection, i.e. the first selection or the second selection, are serially connected. In some embodiments, the affinity chromatography matrix or matrices employed in a first and/or second selection adsorbs or is capable of selecting or enriching at least about $50\times10^6$ cells/mL, $100\times10^6$ cells/mL, $200\times10^6$ cells/mL or $400\times10^6$ cells/mL. In some embodiments, the adsorption capacity can be modulated based on the diameter and/or length of the column. In some embodiments, the culture-initiating ratio of the selected or enriched composition is achieved by choosing a sufficient amount of matrix and/or at a sufficient relative amount to achieve the culture-initiating ratio assuming based on, for example, the adsorption capacity of the column or columns for selecting cells.

In one exemplary embodiment, the adsorption capacity of the matrix or matrices is the same between the first and second selection, e.g. is or is about $1\times10^8$ cells/mL for both, whereby enrichment or selection of cells in the first selection and second selection results in a composition containing a CD4+ cells to CD8+ cells at a culture-initiating ratio of or about 1:1. In another exemplary embodiment, the adsorption capacity of the matrix or matrices used in one of the first selection or second selection is at least 1.5-fold, 2.0-fold, 3.0-fold, 4.0-fold, 5.0-fold, 6.0-fold, 7.0-fold, 8.0-fold, 9.0-fold, 10.0-fold or greater than the adsorption capacity of the matrix or matrices used in the other of the first selection or second selection, thereby resulting in a culture-initiation ratio in which cells selected with the greater adsorption capacity, e.g. CD4$^+$ cells or CD8+ cells, are present in the culture initiating ratio in an amount that is at least 1.5-fold, 2.0-fold, 3.0-fold, 4.0-fold, 5.0-fold, 6.0-fold, 7.0-fold, 8.0-fold, 9.0-fold, 10.0-fold or greater than the other cell population. It is within the level of a skilled artisan to select or choose an appropriate volume, diameter or number of affinity matrix chromatography columns for the first and/or second selection depending on the desired or chosen culture-initiating ratio of the generated composition containing enriched or selected cells.

Exemplary processes for carrying out selections by the provided methods are set forth in Example 2. In some embodiments, such processes achieve a desired culture-initiation ratio in an enriched or generated composition.

In some embodiments, the first and/or second selection in the provided methods includes first enriching for one of CD4+ or CD8+ cells, and then enriching for a sub-population of cells based on, for example, surface expression of a marker expressed on resting, naïve or central memory T cells, e.g. a marker that is CD28, CD62L, CCR7, CD127 or CD27. In some embodiments, the first and/or second selection includes enriching for CD8+ cells, said selection further comprises enriching for central memory T ($T_{CM}$) cells, where the other of the first and/or second selection includes enriching for CD4+ cells. In some embodiment, the methods are performed to enrich or select for CD4+ cells and to enrich or select for a sub-population of cells that are CD8+/CD28+, CD8+/CD62L+, CD8+/CCR7+, CD8+/CD127+ or CD8+/CD27+. In some embodiments, the first selection includes enriching for CD8+ cells and the second selection includes enriching for CD4+ cells, where the first selection, which includes cells enriched for CD8+ cells, further includes enriching for central memory T ($T_{CM}$) cells or enriching for cells that expresses a marker that is CD28, CD62L, CCR7, CD127 or CD27, thereby generating a composition, such as a culture-initiation composition, containing CD4+ cells and CD8+ enriched for central memory T ($T_{CM}$) cells or a cell expressing a marker that is CD28, CD62L, CCR7, CD127 or CD27. In some embodiments, the first selection includes enriching for CD4+ cells and the second selection includes enriching for CD8+ cells, wherein the second selection, which includes cells enriched for CD8+ cells, further includes enriching for central memory T ($T_{CM}$) cells or enriching for cells that expresses a marker that is CD28, CD62L, CCR7, CD127 or CD27, thereby generating a composition, such as a culture-initiation composition, containing CD4+ cells and CD8+ enriched for central memory T ($T_{CM}$) cells or a cell expressing a marker that is CD28, CD62L, CCR7, CD127 or CD27.

In some such embodiments involving a further enrichment of a sub-population of cells, to achieve the culture-initiating ratio of CD4+ cells or a sub-population thereof to CD8+ cells or a sub-population thereof, the adsorption capacity of a column matrix or matrices is adjusted to account for differences in the frequency of a sub-population, i.e. CD4+ or CD8+ cells enriched for resting, naïve, central memory cells or cells expressing a marker that is CD28, CD62L, CCR7, CD127 or CD27, compared to the frequency of cells of the respective CD4+ or CD8+ parent population in the starting sample from the subject. The relative level or frequency of various cell populations in a subject can be determined based on assessing surface expression of a marker or markers present on such populations or subpopulations. A number of well-known methods for assessing expression level of surface markers or proteins may be used, such as detection by affinity-based methods, e.g., immuno-affinity-based methods, e.g., in the context of cell surface proteins, such as by flow cytometry.

In an exemplary embodiment, a sample is enriched for CD4+ and CD8+/CD62L+ cells to yield a CD4+ to CD8+ ratio of 1:1. In this exemplary embodiment, the first selection can include enriching for CD8+ cells using a column with an adsorption capacity adjusted for the relative frequencies of CD4+ cells to CD8+/CD62L+ cells known to be present in the sample, or using ratios generally estimated to be in such samples. For example, the CD62L+ subpopulation of CD8+ cells collected from a human subject can sometimes be about 25% of the total CD8+ T cell fraction. See e.g. Maldonado, *Arthritis Res Ther.* 2003; 5(2): R91-R96. In such an embodiment, the columns can be arrayed to collect 4-fold more CD8+ cells than CD4+ cells in order to generate a 1:1 culture initiation ratio of the CD4+ cells and the CD8+ sub-population further containing CD62L+ cells. Thus, assuming a similar adsorption capacity and efficiency for each selection column, the CD8+ column can be about or approximately 4-fold larger than the CD4 selection column or the CD62L selection column. The size of the columns can also be adjusted for expected yield. For example, if each column is only 80% efficient, the size of each column can be adjusted to account for the efficiency of each subsequent selection.

For example a desired or chosen culture initiation composition can be one that contains $200\times10^6$ CD4+ cells and $200\times10^6$ CD8+/CD62L+ cells. In this example, assuming the ratios presented above, the sample to be enriched can contain at least or about $200\times10^6$ CD4+ cells and at least or about $800\times10^6$ CD8+ cells, approximately 25% of which ($200\times10^6$) may also be CD62L+. Assuming that each 2 mL of selection matrix can enrich for about or approximately $200\times10^6$ cells, a CD8 selection column with 8 mL of selection matrix can bind about or approximately $800\times10^6$ CD8+ cells while the flow-through passes to the CD4 selection column. A CD4 selection column with 2 mL of selection matrix can bind about or approximately $200\times10^6$ CD4+ cells. The CD8+ cells can be further enriched for CD62L by eluting the CD8+ cells into a CD62L selection column. In this exemplary embodiment, the CD62L selection column can contain 2 mL of selection matrix, thus enriching for about or approximately $200\times10^6$ CD8+/CD62L+ cells. The CD4 and CD8/CD62L columns can be eluted into a culture vessel, yielding the initiation culture composition or a composition having about or approximately a 1:1 culture-initiation ratio.

In another exemplary embodiment, a sample is enriched for CD4+ and CD8+/CCR7+ cells to yield a CD4+ to CD8+ ratio of 1:1. In this exemplary embodiment, the first selection can include enriching for CD8+ cells using a column with an adsorption capacity adjusted for the relative frequencies of CD4+ cells to CD8+/CCR7+ cells known to be present in the sample, or using ratios generally estimated to be in such samples. For example, the CCR7+ subpopulation of CD8+ cells collected from a human subject can sometimes be about 60% of the total CD8+ T cell fraction. See e.g. Chen, *Blood.* 2001 Jul. 1; 98(1):156-64. The columns can be arrayed to collect 31%3-fold more CD8+ cells than CD4+ cells in order to generate a 1:1 culture initiation ratio. Assuming a similar adsorption capacity and efficiency for each selection column, the CD8+ column can be about or approximately 31%3-fold larger than the CD4 selection column or the CCR7 selection column. The size of the columns can also be adjusted for expected yield. For example, if each column is only 80% efficient, the size of each column can be adjusted to account for the efficiency of each subsequent selection.

For example, a desired initiation culture can contain $200\times10^6$ CD4+ cells and $200\times10^6$ CD8+/CCR7+ cells. In this example, assuming the ratios presented above, the sample to be enriched can contain at least $200\times10^6$ CD4+ cells and at least or about $6.6\times10^6$ CD8+ cells, approximately 60% of which ($200\times10^6$) may also be CCR7+. Assuming that each 2 mL of selection matrix can enrich for $200\times10^6$ cells, a CD8 selection column with 31%3 mL of selection matrix can bind about or approximately $6.6\times10^6$ CD8+ cells while the flow-through passes to the CD4 selection column. A CD4 selection column with 2 mL of selection matrix can bind about or approximately $200\times10^6$ CD4+ cells. The CD8+ cells can be further enriched for CD62L by eluting the CD8+ cells into a CCR7 selection column. In this exemplary embodiment, the CCR7 selection column can contain 1 mL of selection matrix, thus enriching for about or approximately $200\times10^6$ CD8+/CCR7$^+$ cells. The CD4 and CCCR7 columns can be eluted into a culture vessel, yielding the initiation culture containing about or approximately $200\times10^6$ CD4+ cells and about or approximately $200\times10^6$ CD8+/CCR7+ cells, or a 1:1 culture-initiation ratio.

It is within the level of a skilled artisan to empirically select or choose an appropriate volume, diameter or number of affinity matrix chromatography columns for the first and/or second and/or third selection depending on the desired or chosen culture-initiating ratio of the generated composition containing enriched or selected cells, the expected frequency of each sub-population, the varying efficiencies of each selection column and other factors within the level of the skilled artisan and in view of the above exemplification.

B. Incubation of Isolated Cells

In some embodiments, the provided methods include one or more of various steps for incubating isolated cells and cell populations, such as populations isolated according to the methods herein, such as steps for incubating an isolated CD4+ T cell population, e.g., unfractionated CD4+ T cell population or subpopulation(s) thereof, and an isolated CD8+ T cell population, e.g., isolated unfractionated CD8+

T cell population or subpopulation(s) thereof. In some embodiments, the cell populations are incubated in a culture-initiating composition.

The plurality of isolated cell populations, e.g., the CD4+ and CD8+ cell populations (e.g., unfractionated or subpopulations thereof) are generally incubated with the cell populations combined in a culture-initiating composition in the same culture vessel, such as the same unit, chamber, well, column, tube, tubing set, valve, vial, culture dish, bag, or other container for culture or cultivating cells.

In some aspects, the cell populations or cell types are present in the culture-initiating composition at a culture-initiating ratio, e.g., ratio of $CD4^+$ and $CD8^+$ cells, designed to achieve a particular desired output ratio, or a ratio that is within a certain range of tolerated error of such a desired output ratio, following the incubation and/or engineering steps, or designed to do so a certain percentage of the time. The output ratio, for example, can be a ratio optimal for achieving one or more therapeutic effects upon administration to a patient, e.g., via adoptive cell therapy. In some aspects, the culture-initiating ratio is determined empirically, e.g., using a determination method as described herein, for example, to determine the optimal culture-initiating ratio for achieving a desired output ratio in a particular context.

The incubation steps can include culture, cultivation, stimulation, activation, propagation, including by incubation in the presence of stimulating conditions, for example, conditions designed to induce proliferation, expansion, activation, and/or survival of cells in the population, to mimic antigen exposure, and/or to prime the cells for genetic engineering, such as for the introduction of a genetically engineered antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In one example, the stimulating conditions include one or more agent, e.g., ligand, which turns on or initiates TCR/CD3 intracellular signaling cascade in a T cell. Such agents can include antibodies, such as those specific for a TCR component and/or costimulatory receptor, e.g., anti-CD3, anti-CD28, anti-4-1BB, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). Optionally, the expansion method may further comprise the step of adding IL-2 and/or IL-15 and/or IL-7 and/or IL-21 to the culture medium (e.g., wherein the concentration of IL-2 is at least about 10 units/m 1).

In some aspects, incubation is carried out in accordance with techniques such as those described in U.S. Pat. No. 6,040,177 to Riddell et al., Klebanoff et al. (2012) *J Immunother.* 35(9): 651-660, Terakura et al. (2012) Blood. 1:72-82, and/or Wang et al. (2012) *J Immunother.* 35(9):689-701.

In some embodiments, the cell populations, such as $CD4^+$ and $CD8^+$ populations or subpopulations, are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. In some embodiments, a temperature shift is effected during culture, such as from 37 degrees Celsius to 35 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, populations of $CD4^+$ and $CD8^+$ that are antigen specific can be obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen. Naive T cells may also be used.

Interim Assessment and Adjustment

In some embodiments, the methods include assessment and/or adjustment of the cells or composition containing the cells, at a time subsequent to the initiation of the incubation or culture, such as at a time during the incubation. Assessment can include taking one or more measurements of a composition or vessel containing the cells, such as assessing cells for proliferation rate, degree of survival, phenotype, e.g., expression of one or more surface or intracellular markers, such as proteins or polynucleotides, and/or assessing the composition or vessel for temperature, media component(s), oxygen or carbon dioxide content, and/or presence or absence or amount or relative amount of one or more factors, agents, components, and/or cell types, including subtypes. Assessment in some embodiments includes determining an intermediate ratio of a plurality, e.g., two cell types, such as $CD4^+$ and $CD8^+$ T cells, in the composition or vessel being incubated. In some aspects, the assessment is performed in an automated fashion, for example, using a device as described herein, and/or is set ahead of time to be carried out at certain time-points during incubation. In some aspects, the outcome of the assessment, such as a determined interim ratio of two types of cells, indicates that an adjustment should be made, such as addition or removal of one or more cell types.

Adjustment can include adjusting any cell culture factor or parameter, such as temperature, length (time) for which incubation or a step thereof will be carried out (duration of incubation), replenishment, addition and/or removal of one or more components in the composition being incubated, e.g., media or buffer or components thereof, agents, e.g., nutrients, amino acids, antibiotics, ions, and/or stimulatory factors, such as cytokines, chemokines, antigens, binding partners, fusion proteins, recombinant soluble receptors, or cells or cell types or populations of cells. In some aspects, the removal or addition of various components or other adjustment is carried out in an automated fashion, for example, using a device or system as described herein. In some embodiments, the system is programmed such that an adjustment is automatically initiated based on a certain readout from an interim assessment. For example, in some cases, a system or device is programmed to carry out one or more assessments at a particular time; the system or device in such cases can be further programmed such that a particular outcome of such an assessment, such as a particular ratio of one cell type to another, initiates a particular adjustment, such as addition of one or more of the cell types.

In some aspects, the adjustment is carried out by addition or removal in a way that does not disrupt a closed environment containing the cells and compositions, such as by input and/or removal valves, designed to add or remove components while maintaining sterility, such as in one or more device or system as described herein.

In a particular embodiment, an interim ratio of $CD4^+$ to $CD8^+$ T cells is assessed during the incubation period. In some embodiments, the assessment is carried out after 1, 2, 3, 4, 5, 6, or 7 days, such as between 3 and 5 days, and/or at a time point in which all cells are in or suspected of being in cell cycle. In some aspects, the interim ratio so-determined indicates that $CD4^+$ or $CD8^+$ T cells, such as cells of the isolated population of $CD4^+$ T cells or isolated population of $CD8^+$ T cells (e.g., sub-population, such as central memory $CD8^+$ T cells), should be added to or enriched in the culture vessel or to the composition being incubated. Thus, in some aspects, the assessment is followed by such an addition or removal, typically an addition. In some aspects, multiple assessments and possible adjustments are carried out over the course of incubation, e.g., in an iterative fashion.

In some embodiments, where cells are engineered, e.g., to introduce a genetically engineered antigen receptor, the incubation in the presence of one or more stimulating agents continues during the engineering phase.

In some embodiments, the cells are incubated for at or about 1, 2, 3, 4, 5, 6, 7, 8, 9, 10, 11, 12, 13, or 14 days, either in total or prior to engineering.

C. Engineering, Engineered Antigen Receptors, and Engineered Cells

In some embodiments, the methods include genetic engineering of the isolated and/or incubated cells, such as to introduce into the cells recombinant genes for expression of molecules, such as receptors, e.g., antigen receptors, useful in the context of adoptive therapy.

Among the genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.*, 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. This can be carried out in accordance with known techniques (see, e.g., Riddell et al., U.S. Pat. No. 6,040,177, at columns 14-17) or variations thereof that will be apparent to those skilled in the art based upon the present disclosure.

The engineering generally includes introduction of gene or genes for expression of a genetically engineered antigen receptor. Among such antigen receptors are genetically engineered T cell receptors (TCRs) and components thereof, and functional non-TCR antigen receptors, such as chimeric antigen receptors (CAR).

The antigen receptor in some embodiments specifically binds to a ligand on a cell or disease to be targeted, such as a cancer or other disease or condition, including those described herein for targeting with the provided methods and compositions. Exemplary antigens are orphan tyrosine kinase receptor RORl, tEGFR, Her2, Ll-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, Li-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3 and/or biotinylated molecules, and/or molecules expressed by HIV, HCV, HBV or other pathogens.

Antigen Receptors

In one embodiment, the engineered antigen receptors are CARs. The CARs generally include genetically engineered receptors including an extracellular ligand binding domain linked to one or more intracellular signaling components. Such molecules typically mimic or approximate a signal through a natural antigen receptor and/or signal through such a receptor in combination with a costimulatory receptor.

In some embodiments, CARs are constructed with specificity for a particular marker, such as a marker expressed in a particular cell type to be targeted by adoptive therapy, e.g., a cancer marker. This is achieved in some aspects by inclusion in the extracellular portion of the CAR one or more antigen binding molecule, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the CAR comprises an antibody heavy chain domain that specifically binds a cell surface antigen of a cell or disease to be targeted, such as a tumor cell or a cancer cell, such as any of the target antigens described herein or known in the art.

In some embodiments, the tumor antigen or cell surface molecule is a polypeptide. In some embodiments, the tumor antigen or cell surface molecule is selectively expressed or overexpressed on tumor cells as compared to non-tumor cells of the same tissue.

In some embodiments, the CAR binds a pathogen-specific antigen. In some embodiments, the CAR is are specific for viral antigens (such as HIV, HCV, HBV, etc.), bacterial antigens, and/or parasitic antigens.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The CAR generally includes intracellular signaling component or components. In some embodiments, the CAR includes an intracellular component of the TCR complex, such as a TCR CD3+ chain that mediates T-cell activation and cytotoxicity, e.g., CD3 zeta chain. Thus, in some aspects, the antigen binding molecule is linked to one or more cell signaling modules. In some embodiments, cell signaling modules include CD3 transmembrane domain, CD3 intracellular signaling domains, and/or other CD transmembrane domains. In some embodiments, the CAR further includes a portion of one or more additional molecules such as Fc receptor 7, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling domain of the CAR activates at least one of the normal effector functions of the immune cell, e.g., T cell engineered to express the cell. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule. Such truncated portion in some aspects is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

Primary cytoplasmic signaling sequences can in some aspects regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS.

In certain embodiments, the intracellular signaling domain comprises a CD28 transmembrane and signaling domain linked to a CD3 intracellular domain. In some embodiments, the intracellular signaling domain comprises a chimeric CD28 and CD137 co-stimulatory domains, linked to a CD3 intracellular domain. In some embodiments, a CAR can also include a transduction marker (e.g., tEGFR). In some embodiments, the intracellular signaling domain of the CD8+ cytotoxic T cells is the same as the intracellular signaling domain of the CD4+ helper T cells. In some embodiments, the intracellular signaling domain of the CD8+ cytotoxic T cells is different than the intracellular signaling domain of the CD4+ helper T cells.

In some embodiments, the CAR encompasses two or more costimulatory domain combined with an activation domain, e.g., primary activation domain, in the cytoplasmic portion. One example is a receptor including intracellular components of CD3-zeta, CD28, and 4-1BB.

CARs and production and introduction thereof can include those described, for example, by published patent disclosures WO200014257, U.S. Pat. No. 6,451,995, US2002131960, U.S. Pat. Nos. 7,446,190, 8,252,592, EP2537416, US2013287748, and WO2013126726, and/or those described by Sadelain et al., Cancer Discov. 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer,* 2012 March 18(2): 160-75.

In some embodiments, the T cells are modified with a recombinant T cell receptor. In some embodiments, the recombinant TCR is specific for an antigen, generally an antigen present on a target cell, such as a tumor-specific antigen, an antigen expressed on a particular cell type associated with an autoimmune or inflammatory disease, or an antigen derived from a viral pathogen or a bacterial pathogen.

In some embodiments, the T cells are engineered to express T-cell receptors (TCRs) cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15:169-180 and Cohen et al. (2005) *J Immunol.* 175:5799-5808. In some embodiments, phage display is used to isolate TCRs against a target antigen (see, e.g., Varela-Rohena et al. (2008) *Nat Med.* 14:1390-1395 and Li (2005) *Nat Biotechnol.* 23:349-354.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, genetic transfer of the TCR is accomplished via retroviral or lentiviral vectors, or via transposons (see, e.g., Baum et al. (2006) *Molecular Therapy: The Journal of the American Society of Gene Therapy.* 13:1050-1063; Frecha et al. (2010) *Molecular Therapy: The Journal of the American Society of Gene Therapy.* 18:1748-1757; an Hackett et al. (2010) *Molecular Therapy: The Journal of the American Society of Gene Therapy.* 18:674-683.

In some embodiments, gene transfer is accomplished by first stimulating T cell growth and the activated cells are then transduced and expanded in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines, such as proinflammatory cytokines, e.g., IL-2, IL-12, IL-7, IL-15, IL-21.

Introduction of the Genetically Engineered Components

Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November; 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

In some embodiments, the same CAR is introduced into each of $CD4^+$ and $CD8^+$ T lymphocytes. In some embodiments, a different CAR is introduced into each of $CD4^+$ and $CD8^+$ T lymphocytes. In some embodiments, the CAR in each of these populations has an antigen binding molecule that specifically binds to the same antigen. In some embodiments, the CAR in each of these populations binds to a different molecule. In some embodiments, the CAR in each of these populations has cellular signaling modules that differ. In some embodiments each of the $CD4^+$ or $CD8^+$ T lymphocytes have been sorted in to naive, central memory, effector memory or effector cells prior to transduction.

In other embodiments, the cells, e.g., T cells, are not engineered to express recombinant receptors, but rather include naturally occurring antigen receptors specific for desired antigens, such as tumor-infiltrating lymphocytes and/or T cells cultured in vitro or ex vivo, e.g., during the incubation step(s), to promote expansion of cells having particular antigen specificity. For example, in some embodiments, the cells are produced for adoptive cell therapy by isolation of tumor-specific T cells, e.g. autologous tumor infiltrating lymphocytes (TIL). The direct targeting of human tumors using autologous tumor infiltrating lymphocytes can in some cases mediate tumor regression (see Rosenberg SA, et al. (1988) *N Engl J Med.* 319:1676-1680). In some embodiments, lymphocytes are extracted from resected tumors. In some embodiments, such lymphocytes are expanded in vitro. In some embodiments, such lymphocytes are cultured with lymphokines (e.g., IL-2). In some embodiments, such lymphocytes mediate specific lysis of autologous tumor cells but not allogeneic tumor or autologous normal cells.

In some aspects, the incubation and/or engineering steps and/or the methods generally result in a desired output ratio (or a ratio that is within a tolerated error or difference from such a ratio), or do so within a certain percentage of the time that the methods are performed.

D. Cryopreservation

In some embodiments, the provided methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

II. Kits and Systems

Also provided are systems, apparatuses, and kits useful in performing the provided methods. In one example, a single system is provided which carries out one or more of the isolation, cell preparation, separation, e.g., separation based on density, affinity, sensitivity to one or more components, or other property, washing, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

Also provided are kits for carrying out the provided methods. In some embodiments, the kits include antibodies or other binding partners, generally coupled to solid supports, for the isolation, e.g., for immunoaffinity-based separation steps, of the methods.

In some embodiments, the kit comprises antibodies for positive and negative selection, bound to magnetic beads. In one embodiment, the kit comprises instructions to carry out selection starting with a sample, such as a PBMC sample, by selecting based on expression of a first surface marker, recognized by one or more of the antibodies provided with the kit, retaining both positive and negative fractions. In some aspects, the instructions further include instructions to carry out one or more additional selection steps, starting with the positive and/or negative fractions derived therefrom, for example, while maintaining the compositions in a contained environment and/or in the same separation vessel.

In one embodiment, a kit comprises anti-CD4, anti-CD14, anti-CD45RA, anti-CD14, and anti-CD62L antibodies, bound to magnetic beads. In one embodiment, the kit comprises instructions to carry out selection starting with a sample, such as a PBMC sample, by selecting based on CD4 expression, retaining both positive and negative fractions, and on the negative fraction, further subjecting the fraction to a negative selection using the anti-CD14, anti-CD45RA antibodies, and a positive selection using the anti-CD62L antibody, in either order. Alternatively, the components and instructions are adjusted according to any of the separation embodiments described herein.

In some embodiments, the kit further includes instructions to transfer the cells of the populations isolated by the selection steps to a culture, cultivation, or processing vessel, while maintaining the cells in a self-contained system. In some embodiments, the kit includes instructions to transfer the different isolated cells at a particular ratio.

III. Cells, Compositions, and Methods of Administration

Also provided are cells, cell populations, and compositions (including pharmaceutical and therapeutic compositions) containing the cells and populations, produced by the provided methods. Also provided are methods, e.g., therapeutic methods for administrating the cells and compositions to subjects, e.g., patients.

Provided are methods of administering the cells, populations, and compositions, and uses of such cells, populations, and compositions to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, cells and compositions prepared by the provided methods, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) *PLoS ONE* 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

Also provided are pharmaceutical compositions for use in such methods.

Among the diseases, conditions, and disorders for treatment with the provided compositions, cells, methods and uses are tumors, including solid tumors, hematologic malignancies, and melanomas, and infectious diseases, such as infection with a virus or other pathogen, e.g., HIV, HCV, HBV, CMV, and parasitic disease. In some embodiments, the disease or condition is a tumor, cancer, malignancy, neoplasm, or other proliferative disease. Such diseases include but are not limited to leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin (including melanoma), bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease multiple sclerosis, asthma, and/or a disease or condition associated with transplant.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, Li-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3 and/or biotinylated molecules, and/or molecules expressed by HIV, HCV, HBV or other pathogens.

In some embodiments, the cells and compositions are administered to a subject in the form of a pharmaceutical composition, such as a composition comprising the cells or cell populations and a pharmaceutically acceptable carrier or excipient. The pharmaceutical compositions in some embodiments additionally comprise other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The choice of carrier will in the pharmaceutical composition is determined in part by the particular engineered CAR or TCR, vector, or cells expressing the CAR or TCR, as well as by the particular method used to administer the vector or host cells expressing the CAR. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition.

In addition, buffering agents in some aspects are included in the composition. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

In some embodiments, the pharmaceutical composition employs time-released, delayed release, and/or sustained release delivery systems, such that the delivery of the composition occurs prior to, and with sufficient time to cause, sensitization of the site to be treated. Many types of release delivery systems are available and known to those of ordinary skill in the art. Such systems in some aspects can avoid repeated administrations of the composition, thereby increasing convenience to the subject and the physician.

In some embodiments, the he pharmaceutical composition comprises the cells or cell populations in an amount that is effective to treat or prevent the disease or condition, such as a therapeutically effective or prophylactically effective amount. Thus, in some embodiments, the methods of administration include administration of the cells and populations at effective amounts. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8$^+$ and CD4$^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4$^+$ to CD8$^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4$^+$ to CD8$^+$ cells, and/or is based on a desired fixed or minimum dose of CD4$^+$ and/or CD8$^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $10^4$ and at or about $10^9$ cells/kilograms (kg) body weight, such as between $10^5$ and $10^6$ cells/kg body weight, for example, at or about $1 \times 10^5$ cells/kg, $1.5 \times 10^5$ cells/kg, $2 \times 10^5$ cells/kg, or $1 \times 10^6$ cells/kg body weight. For example, in some embodiments, the cells are administered at, or within a certain range of error of, between at or about $10^4$ and at or about $10^9$ T cells/kilograms (kg) body weight, such as between $10^1$ and $10^6$ T cells/kg body weight, for example, at or about $1 \times 10^5$ T cells/kg, $1.5 \times 10^5$ T cells/kg, $2 \times 10^6$ T cells/kg, or $1 \times 10^6$ T cells/kg body weight.

In some embodiments, the cells are administered at or within a certain range of error of between at or about $10^4$ and at or about $10^9$ CD4$^+$ and/or CD8$^+$ cells/kilograms (kg) body weight, such as between $10^5$ and $10^6$ CD4$^+$ and/or CD8$^+$ cells/kg body weight, for example, at or about $1 \times 10^5$ CD4$^+$ and/or CD8$^+$ cells/kg, $1.5 \times 10^5$ CD4$^+$ and/or CD8$^+$ cells/kg, $2 \times 10^5$ CD4$^+$ and/or CD8$^+$ cells/kg, or $1 \times 10^6$ CD4$^+$ and/or CD8$^+$ cells/kg body weight.

In some embodiments, the cells are administered at or within a certain range of error of, greater than, and/or at least about $1 \times 10^6$, about $2.5 \times 10^6$, about $5 \times 10^6$, about $7.5 \times 10^6$, or about $9 \times 10^6$ CD4$^+$ cells, and/or at least about $1 \times 10^6$, about $2.5 \times 10^6$, about $5 \times 10^6$, about $7.5 \times 10^6$, or about $9 \times 10^6$ CD8+ cells, and/or at least about $1 \times 10^6$, about $2.5 \times 10^6$, about $5 \times 10^6$, about $7.5 \times 10^6$, or about $9 \times 10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ CD4$^+$ cells, and/or between about $10^8$ and $10^{12}$ or between about $10^{10}$ and $10^{11}$ CD8$^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of CD4$^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

The cell populations and compositions in some embodiments are administered to a subject using standard administration techniques, including oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

The cell populations obtained using the methods described herein in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cell populations are administered prior to the one or more additional therapeutic agents. In some embodiments, the cell populations are administered after to the one or more additional therapeutic agents.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 111 (1995), and U.S. Pat. No. 5,087,616.

IV. Definitions

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, "percent (%) amino acid sequence identity" and "percent identity" when used with respect to an amino acid sequence (reference polypeptide sequence) is defined as the percentage of amino acid residues in a candidate sequence (e.g., a streptavidin mutein) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. Amino acids generally can be grouped according to the following common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative amino acid substitutions will involve exchanging a member of one of these classes for another class.

As used herein, a subject includes any living organism, such as humans and other mammals. Mammals include, but are not limited to, humans, and non-human animals, including farm animals, sport animals, rodents and pets.

As used herein, a composition refers to any mixture of two or more products, substances, or compounds, including cells. It may be a solution, a suspension, liquid, powder, a paste, aqueous, non-aqueous or any combination thereof.

As used herein, "depleting" when referring to one or more particular cell type or cell population, refers to decreasing the number or percentage of the cell type or population, e.g., compared to the total number of cells in or volume of the composition, or relative to other cell types, such as by negative selection based on markers expressed by the population or cell, or by positive selection based on a marker not present on the cell population or cell to be depleted. The term does not require complete removal of the cell, cell type, or population from the composition.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, the terms "treatment," "treat," and "treating," refer to complete or partial amelioration or reduction of a disease or condition or disorder, or a symptom, adverse effect or outcome, or phenotype associated therewith. In certain embodiments, the effect is therapeutic, such that it partially or completely cures a disease or condition or adverse symptom attributable thereto.

As used herein, a "therapeutically effective amount" of a compound or composition or combination refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control or fluorescence minus one (FMO) gating control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control or fluorescence minus one (FMO) gating control under otherwise identical conditions, and/or at a level substantially lower than that for cell known to be positive for the marker, and/or at a level substantially similar as compared to that for a cell known to be negative for the marker.

In some embodiments, a decrease in expression of one or markers refers to loss of 1 $\log^{10}$ in the mean fluorescence intensity and/or decrease of percentage of cells that exhibit the marker of at least about 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 20 and 100% when compared to a reference cell population. In some embodiments, a cell population positive for one or markers refers to a percentage of cells that exhibit the marker of at least about 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 50 and 100% when compared to a reference cell population.

V. Exemplary Embodiments

Among the embodiments provided herein are:

1. A method for enriching CD4+ or CD8+ T cells, the method including:
   (a) performing a first selection in a closed system, said first selection including enriching for one of (i) CD4+ cells and (ii) CD8+ cells from a sample containing primary human T cells, the enrichment thereby generating a first selected population and a non-selected population; and
   (b) performing a second selection in the closed system, said second selection including enriching for the other of (i) CD4+ cells and (ii) CD8+ cells from the non-selected population, the enrichment thereby generating a second selected population,
   wherein the method produces an enriched composition, which is enriched for CD4+ cells and CD8$^+$ cells and includes cells of the first selected population and cells of the second selected population.

2. The method of embodiment 1, further including (c) combining cells of the first selected population and cells of the second selected population, thereby producing the enriched composition and/or wherein the CD4+ and CD8+ cells in the enriched composition are present at a culture-initiating ratio of CD4+ cells to CD8+ cells.

3. The method of embodiment 2, wherein said combining is performed in the closed system.

4. A method for producing genetically engineered T cells, the method including:
   (a) performing a first selection in a closed system, said first selection including enriching for one of (i) CD4$^+$ cells and (ii) CD8+ cells from a sample containing primary human T cells, the enrichment thereby generating a first selected population and a non-selected population; and
   (b) performing a second selection in the closed system, said second selection including enriching for the other of (i) CD4+ cells and (ii) CD8+ cells from the non-selected population, the enrichment thereby generating a second selected population;
   (c) incubating a culture-initiating composition, which contains cells of the first selected population and cells of the second selected population, in a culture vessel under stimulating conditions, thereby generating stimulated cells; and
(d) introducing a genetically engineered antigen receptor into stimulated cells generated in (c),
wherein the method thereby generates an output composition including CD4$^+$ T cells and CD8$^+$ T cells expressing the genetically engineered antigen receptor.

5. The method of embodiment 4, further including, prior to step (c), combining cells of the first and second selected cell populations to produce the culture-initiating composition and/or wherein the CD4+ and CD8+ cells in the culture-initiating composition are present at a culture-initiating ratio of CD4+ cells to CD8+ cells.

6. The method of embodiment 5, wherein said combining is performed in the closed system.

7. The method of any of embodiments 1-6, wherein one or more of the steps are carried out in an automated fashion and/or wherein the closed system is automated.

8. The method of any of embodiments 2-7, wherein the culture-initiating ratio of CD4+ to CD8$^+$ cells is between at or about 10:1 and at or about 1:10, between at or about 5:1 and at or about 1:5, or between at or about 2:1 and at or about 1:2.

9. The method of any of embodiments 2-8, wherein the culture-initiating ratio of CD4+ to CD8+ cells is at or about 1:1.

10. The method of any of embodiments 2-6, wherein the sample is obtained from a human subject and:
the culture-initiating ratio of CD4$^+$ to CD8$^+$ cells is different than the ratio of CD4$^+$ to CD8$^+$ cells in the sample from the subject; and/or
the culture-initiating ratio of CD4$^+$ to CD8$^+$ cells is at least 10%, at least 20%, at least 30%, at least 40%, or at least 50% greater or less than the ratio of CD4$^+$ to CD8$^+$ cells in the sample from the subject.

11. The method of any of embodiments 1-10, wherein enriching cells in the first and/or second selection includes performing positive selection or negative selection based on expression of a cell surface marker.

12. The method of embodiment 11, wherein enriching for cells in the first and/or second selection includes negative selection, which includes depleting cells expressing a non-T cell surface marker.

13. The method of embodiment 12, wherein the non-T cell marker comprises CD14.

14. The method of any of embodiments 1-13, wherein enriching cells in the first or second selection includes performing a plurality of positive or negative selection steps based on expression of a cell surface marker or markers to enrich for CD4+ or CD8+ cells.

15. The method of any of embodiments 1-14, wherein the enriching cells in the first and/or second selection includes immunoaffinity-based selection.

16. The method of embodiment 15, wherein the immunoaffinity-based selection is effected by contacting cells with an antibody capable of specifically binding to a cell surface marker and recovering cells bound to the antibody, thereby effecting positive selection, or recovering cells not bound to the antibody, thereby effecting negative selection, wherein the recovered cells are enriched for the CD4+ cells or the CD8+ cells and antibody is immobilized on a magnetic particle.

17. The method of any of embodiments 1-13, wherein the first selection and second selection are carried out in separate separation vessels, which are operably connected.

18. The method of embodiment 17, wherein the separation vessels are operably connected by tubing.

19. The method of any of embodiments 15-18, wherein the immunoaffinity-based selection is effected by contacting cells with an antibody immobilized on or attached to an affinity chromatography matrix, said antibody capable of specifically binding to a cell surface marker to effect positive or negative selection of CD4+ or CD8+ cells.

20. The method of embodiment 19, wherein:
the antibody further includes one or more binding partners capable of forming a reversible bond with a binding reagent immobilized on the matrix, whereby the antibody is reversibly bound to said matrix during said contacting; and
cells expressing a cell surface marker specifically bound by the antibody on said matrix are capable of being recovered from the matrix by disruption of the reversible binding between the binding reagent and binding partner.

21. The method of embodiment 17, wherein:
the binding partner is selected from among biotin, a biotin analog, and a peptide capable of binding to the binding reagent; and
the binding reagent is selected from among streptavidin, a streptavidin analog or mutein, avidin and an avidin analog or mutein.

22. The method of embodiment 21, wherein:
the binding partner includes a sequence of amino acids set forth in SEQ ID NO:6; and/or
the binding reagent is a streptavidin mutein including the sequence of amino acids set forth in SEQ ID NO: 12, 13, 15 or 16.

23. The method of any of embodiments 19-21, further including, after contacting cells in the sample to an affinity chromatography matrix in the first selection and/or second selection, applying a competition reagent to disrupt the bond between the binding partner and binding reagent, thereby recovering the selected cells from the matrix.

24. The method of embodiment 23, wherein the competition reagent is biotin or a biotin analog.

25. The method of any of embodiments 20-24, wherein the antibody or antibodies in the first and/or second selection has a dissociation rate constant ($k_{off}$) for binding and the cell surface marker of greater than or greater than about $3 \times 10^{-5}$ sec$^{-1}$.

26. The method of any of embodiments 20-25, wherein the antibody or antibodies in the first and/or second selection has an affinity for the cell surface marker of a dissociation constant ($K_d$) in the range of about $10^{-3}$ to $10^{-7}$ or in the range of about $10^{-7}$ to about $10^{-10}$.

27. The method of any of embodiments 20-26, wherein the chromatography matrix of the first and/or second selection is packed in a separation vessel, which is a column.

28. The method of embodiment 19-27, wherein the affinity chromatography matrix adsorbs and/or is capable of selecting at least or at least about $50 \times 10^6$ cells/mL, $100 \times 10^6$ cells/mL, $200 \times 10^6$ cells/mL or $400 \times 10^6$ cells/mL.

29. The method of any of embodiments 19-28, wherein the first and the second selection steps comprise the use of the affinity chromatography matrix and the matrix used in the first and second selection steps are at sufficient relative amounts to achieve the culture-initiation ratio.

30. The method of any of embodiments 1-29, wherein the enriching for the CD4+ cells includes positive selection based on surface expression of CD4.

31. The method of any of embodiments 1-29, wherein the enriching for the CD8+ cells includes positive selection based on surface expression of CD8.

32. The method of any of embodiments 1-29, wherein the one of the first and second selections that includes enriching for the CD8+ cells further includes enriching for central memory T ($T_{CM}$) cells; and/or
enriching for cells expressing a marker selected from among CD28, CD62L, CCR7, CD127 and CD27.

33. The method of any of embodiments 1-32, wherein:
the first selection includes enriching for the CD8+ cells and the second selection includes enriching for the CD4+ cells; and
the first selection further includes enriching for central memory T ($T_{CM}$) cells and/or enriching for cells expressing a marker selected from among CD28, CD62L, CCR7, CD127 and CD27.

34. The method of embodiment 32 or embodiment 33 or embodiment 35, wherein enriching for central memory T ($T_{CM}$) cells and/or enriching for cells expressing the marker includes:
selecting from the first and/or second selected cell population, which is enriched for CD8+ cells, cells expressing CD62L; and/or
selecting, from the first and/or second selected cell population, which is enriched for CD8+ cells, cells expressing CD27; and/or
selecting, from the first and/or second selected cell population, which is enriched for CD8+ cells, cells expressing CCR7; and/or
selecting, from the first and/or second selected cell population, which is enriched for CD8+ cells, cells expressing CD28; and/or
selecting, from the first and/or second selected cell population, which is enriched for CD8+ cells, cells expressing CD127.

35. The method of any of embodiments 1-32, wherein:
the first selection includes enriching for the CD4+ cells and the second selection includes enriching for the CD8+ cells; and
the second selection further includes enriching for central memory T ($T_{CM}$) cells.

36. The method of embodiment 35, wherein:
(i) the first selection includes enriching CD4+ cells by positive selection based on surface expression of CD4, thereby generating the first selected population, which is enriched for CD4+ primary human T cells, and the non-selected sample;
(ii) the second selection includes enriching for the CD8+ cells and further includes enriching the second selected sample for central memory T ($T_{CM}$) cells, wherein enriching for central memory T ($T_{CM}$) cells includes:
negative selection to deplete cells expressing a surface marker present on naïve T cells and positive selection for cells expressing a surface marker present on central memory T ($T_{CM}$) cells and not present on another memory T cell sub-population; or
positive selection for cells expressing a surface marker present on central memory T cells and not on naïve T cells and positive selection for cells expressing a surface marker present on central memory T ($T_{CM}$) cells and not present on another memory T cell sub-population;
thereby generating CD8+ primary human T cells enriched for $T_{CM}$ cells.

37. The method of embodiment 36, wherein:
the marker present on naïve T cells comprises CD45RA; and
enriching for central memory T ($T_{CM}$) cells includes negative selection to deplete cells expressing CD45RA and positive selection for cells expressing a surface marker present on central memory T ($T_{CM}$) cells and not present on another memory T cell sub-population.

38. The method of embodiment 37, wherein:
the surface marker present on central memory T cells and not present on naïve T cells comprises CD45RO;
the enrichment for central memory T ($T_{CM}$) cells includes positive selection for cells expressing CD45RO and positive selection for cells expressing surface marker present on central memory T ($T_{CM}$) cells and not present on another memory T cell sub-population.

39. The method of any of embodiments 36-38, wherein the surface marker present on central memory T ($T_{CM}$) cells and not present on another memory T cell sub-population is selected from the group consisting of CD62L, CCR7, CD27, CD127, and CD44.

40. The method of embodiment 39, wherein the surface marker present on central memory T ($T_{CM}$) cells and not present on another memory T cell sub-population is CD62L.

41. The method of any of embodiments 32-40, wherein the CD8+ population in the enriched composition or the culture-initiating composition includes at least 50% central memory T ($T_{CM}$) cells or includes less than 20% naïve T ($T_N$) cells or includes at least 80% CD62L+ cells.

42. A method for enriching CD4+ and CD8+ T cells, the method including contacting cells of a sample containing primary human T cells with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample; and
recovering cells bound to the first and/or the second immunoaffinity reagent, thereby generating an enriched composition including CD4+ cells and CD8+ cells at a culture-initiating ratio, wherein:
the first and/or second immunoaffinity reagent are present in the incubation composition at a sub-optimal yield concentration, whereby the enriched composition contains less than 70% of the total CD4+ cells in the incubation composition and/or less than 70% of the CD8+ cells in the incubation composition, thereby producing a composition enriched for CD4+ and CD8+ T cells.

43. A method for producing genetically engineered T cells, the method including:
(a) enriching for primary human T cells from a sample containing primary human T cells including:
contacting cells of said sample with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample; and
recovering cells bound to the first and/or the second immunoaffinity reagent, thereby generating an enriched composition including CD4+ cells and CD8+ cells at a culture-initiating ratio, wherein:
the first and/or second immunoaffinity reagent are present in the incubation composition at a sub-optimal yield concentration, whereby the enriched composition contains less than 70% of the total CD4+ cells in the incubation composition and/or less than 70% of the CD8+ cells in the incubation composition; and (b) incubating cells of the enriched composition in a culture-initiation composition in a culture vessel under stimulating conditions, thereby generating stimulated cells, wherein the cells are at or substantially at the culture-initiating ratio; and (c) introducing a genetically engineered antigen receptor into stimulated cells of (b), thereby generating an output composition including CD4$^+$ T cells and CD8$^+$ T cells expressing the genetically engineered antigen receptor.

44. The method of embodiment 42 or embodiment 43, wherein enriching for primary human T cells is performed in a closed system.

45. The method of any of embodiments 42-44, wherein the first and second immunoaffinity reagent are present in the incubation composition at a sub-optimal yield concentration, whereby the enriched composition contains less than 70% of the total CD4+ cells in the incubation composition and less than 70% of the total CD8+ cells in the incubation composition.

46. The method of any of embodiments 42-45, wherein:
the first immunoaffinity reagent is present in the incubation composition at a sub-optimal yield concentration, whereby the enriched composition contains less than 60%, less than 50%, less than 40%, less than 30% or less than 20% of the total CD4+ cells in the incubation composition; and/or
the second immunoaffinity reagent is present in the incubation composition at a sub-optimal yield concentration, whereby the enriched composition contains less than 60%, less than 50%, less than 40%, less than 30% or less than 20% of the total CD8+ cells in the incubation composition.

47. The method of embodiment any of embodiments 42-46, wherein the sample contains at least 1×10$^9$ CD3+ T cells.

48. The method of any of embodiments 42-47, wherein the concentration of one of the first and second immunoaffinity reagent in the incubation composition is greater than that of the other, whereby the greater concentration effects a higher yield in the enriched composition of CD4+ cells or CD8+ cells, respectively, compared to the yield of the other of the CD4+ or CD8+ cells, thereby producing the culture-initiating ratio in the enriched composition.

49. The method of embodiment 48, wherein:
the concentration of one of the first and second immunoaffinity reagents is greater, as compared to the concentration of the other of the first and second immunoaffinity reagents, by at least 1.2-fold, 1.4-fold, 1.6-fold, 1.8-fold, 2.0-fold, 3.0-fold, 4.0-fold, 5.0-fold, 6.0-fold, 7.0-fold, 8.0-fold, 9.0-fold or 10-fold; and/or
the higher yield in the enriched concentration is greater by 1.2-fold, 1.4-fold, 1.6-fold, 1.8-fold, 2.0-fold, 3.0-fold, 4.0-fold, 5.0-fold, 6.0-fold, 7.0-fold, 8.0-fold, 9.0-fold or 10-fold.

50. The method of any of embodiments 42-49, wherein the culture-initiating ratio of CD4$^+$ to CD8$^+$ cells is between at or about 10:1 and at or about 1:10, between at or about 5:1 and at or about 1:5 or is between at or about 2:1 and at or about 1:2.

51. The method of any of embodiments 42-50, wherein the culture-initiating ratio of CD4+ to CD8+ cells is at or about 1:1.

52. The method of any of embodiments 42-51, wherein:
the culture-initiating ratio of CD4$^+$ to CD8$^+$ cells is different than the ratio of CD4$^+$ to CD8+ cells in the sample from the subject; and/or
the culture-initiating ratio of CD4$^+$ to CD8$^+$ cells is at least 10%, at least 20%, at least 30%, at least 40%, or at least 50% greater or less than the ratio of CD4$^+$ to CD8$^+$ cells in the sample from the subject.

53. The method of any of embodiments 42-52, wherein greater than 95% or greater than 98% of the cells in the culture-initiation composition are CD4+ cells and CD8+ cells.

54. The method of any of embodiments 42-53, wherein each of the immunoaffinity reagents contains an antibody.

55. The method of embodiment 54, wherein the antibody is immobilized on the outside surface of a sphere.

56. The method of embodiment 55, wherein the sphere is a magnetic bead.

57. The method of embodiment 55 or embodiment 56, wherein:
the antibody contains one or more binding partners capable of forming a reversible bond with a binding reagent immobilized on the sphere, whereby the antibody is reversibly immobilized to said sphere; and
the method further includes after contacting cells in the sample to the first and second immunoaffinity reagent, applying a competition reagent to disrupt the bond between the binding partner and binding reagent, thereby recovering the selected cells from the sphere.

58. The method of embodiment 57, wherein:
the binding partner is selected from among biotin, a biotin analog, or a peptide capable of binding to the binding reagent; and
the binding reagent is selected from among streptavidin, a streptavidin analog or mutein, avidin, an avidin analog or mutein.

59. The method of embodiment 58, wherein:
the binding partner contains a peptide including the sequence of amino acids set forth in SEQ ID NO:6 and/or
the binding reagent is streptavidin mutein including the sequence of amino acids set forth in SEQ ID NO: 12, 13, 15 or 16.

60. The method of embodiment 58 or embodiment 59, wherein:
the binding reagent is a multimer including one or more monomers of streptavidin or a streptavidin mutein; and
the binding partner is a peptide including a sequential arrangement of at least two modules each capable of reversibly binding with at least one monomer of the binding reagent.

61. The method of embodiment 60, wherein the binding partner contains the sequence of amino acids set forth in any of SEQ ID NOS: 7-10.

62. The method of any of embodiments 57-61, wherein the competition reagent is biotin or a biotin analog.

63. The method of any of embodiments 42-63, wherein the antibody or antibodies in the first and/or second selection has a dissociation rate constant ($k_{off}$) for binding between the antibody and cell surface marker of greater than or greater than about $3\times10^{-5}$ sec$^{-1}$.

64. The method of any of embodiments 42-63, wherein the antibody or antibodies in the first and/or second selection has an affinity with a dissociation constant ($K_d$) in the range of about $10^{-3}$ to $10^{-7}$ or with a dissociation constant in the range of about $10^{-7}$ to about $10^{-10}$.

65. The method of any of embodiments 42-63, wherein one or more steps are carried out in an automated fashion and/or wherein the closed system is automated.

66. The method of any of embodiments 2, 3 and 5-41, including:
prior to performing the first selection and/or second selection, determining the ratio of CD4+ to CD8+ T cells in the sample; and
based on the ratio of CD4+ to CD8+ T cells in the sample, adjusting the first and/or second selection to produce the composition including CD4+ cells and CD8+ cells at the culture-initiating ratio.

67. The method of embodiment 66, wherein:
the first and/or second selection includes immunoaffinity-based selection including an affinity chromatography matrix; and
adjusting the first and/or second selection includes choosing the amount of affinity chromatography matrix in the first and/or second selection sufficient to achieve the culture-initiation ratio.

68. The method of any of embodiments 42-65, including:
prior to contacting cells of the sample with the first and second immunoaffinity reagent, determining the ratio of CD4+ to CD8+ T cells in the sample; and
based on the ratio of CD4+ to CD8+ T cells in the sample, choosing the concentration of the first and/or second immunoaffinity reagent to produce the enriched composition including CD4+ cells and CD8+ cells at the culture-initiating ratio.

69. The method of any of embodiments 1-68, wherein the method results an output composition including a ratio of $CD4^+$ to $CD8^+$ cells that is between at or about 2:1 and at or about 1:5.

70. The method of embodiment 69, wherein the ratio of $CD4^+$ to $CD8^+$ cells in the output composition is 1:1 or is about 1:1.

71. The method of any of embodiments 1-70, wherein the sample is obtained from a subject.

72. The method of embodiment 71, wherein the subject is a subject to whom said genetically engineered T cells or cells for adoptive cell therapy will be administered.

73. The method of embodiment 72, wherein the subject is a subject other than a subject to whom said genetically engineered T cells or cells for adoptive therapy will be administered.

74. The method of any of embodiments 1-73, wherein the sample is blood or a blood-derived sample.

75. The method of any of embodiments 1-74, wherein the sample is a white blood cell sample.

76. The method of any of embodiments 1-75, wherein the sample is an apheresis, peripheral blood mononuclear cell (PBMC), or leukapheresis sample.

77. The method of any of embodiments 4-41 or 43-76, wherein incubating the composition in a culture vessel under stimulating conditions is performed prior to, during and/or subsequent to introducing a genetically engineered antigen receptor.

78. The method of any of embodiments 4-41 or 43-76, wherein incubating the composition in a culture vessel under stimulating conditions is performed prior to, during and subsequent to introducing a genetically engineered antigen receptor.

79. The method of any of embodiments 4-41 or 43-78, wherein the stimulating conditions comprise conditions whereby T cells of the composition proliferate.

80. The method of any of embodiments 4-41 or 43-79, wherein the stimulating condition includes an agent capable of activating one or more intracellular signaling domains of one or more components of a TCR complex.

81. The method of embodiment 80, wherein the one or more components of the TCR complex contains the CD3 zeta chain.

82. The method of any of embodiments 4-41 or 43-81, wherein the stimulating condition contains the presence of an anti-CD3 antibody, and anti-CD28 antibody, anti-4-1BB antibody, and/or a cytokine.

83. The method of embodiment 82, wherein the anti-CD3 antibody and/or the anti-CD28 antibody is present on the surface of a solid support.

84. The method of embodiment 83, wherein the cytokine includes IL-2, IL-15, IL-7, and/or IL-21.

85. The method of any of embodiments 4-41 or 43-84, wherein the genetically engineered antigen receptor includes a T cell receptor (TCR) or a functional non-TCR antigen receptor.

86. The method of embodiment 85, wherein the receptor specifically binds to an antigen expressed by cells of a disease or condition to be treated.

87. The method of any of embodiment 85 or 86, wherein the antigen receptor is a chimeric antigen receptor (CAR).

88. The method of embodiment 87, wherein the CAR contains an extracellular antigen-recognition domain and an intracellular signaling domain including an ITAM-containing sequence and an intracellular signaling domain of a T cell costimulatory molecule.

89. A method of treatment, said method including:
(a) producing an output composition including $CD4^+$ T cells and $CD8^+$ T cells according to any of embodiments 1-88; and
(b) administering cells of the output composition to a subject.

90. The method of embodiment 89, wherein the sample from which the cells are isolated is derived from the subject to which the cells are administered.

91. A composition of cells produced by the method of any of embodiments 1-88.

92. The composition of embodiment 91, including a pharmaceutically acceptable carrier.

93. A method of treatment, said method including administering to a subject a composition of cells of embodiment 91 or 92.

94. The method of embodiment 93, wherein the genetically engineered antigen receptor specifically binds to an antigen associated with the disease or condition.

95. The method of treatment of embodiment 94, wherein the disease or condition is a cancer.

96. The composition of embodiment 91 or embodiment 92 for use in treating a disease or condition in a subject.

97. Use of a composition of embodiment 91 or embodiment 92 for the manufacture of a medicament for treating a disease or disorder in a subject.

98. The composition of embodiment 96 or use of embodiment 97, wherein the genetically engineered antigen receptor specifically binds to an antigen associated with the disease or condition.

99. The composition or use of any of embodiments 96-98, wherein the disease or condition is a cancer.

100. A closed apparatus system for purification of target cells, including:
a) a first affinity chromatography matrix including a first binding agent immobilized thereon, which binding agent specifically binds to a first cell surface marker present on a first cell, wherein the first affinity chromatography matrix is operably connected to a storage reservoir including a cell sample via a first operable connection, said first operable connection capable of permitting passage of cells from the storage reservoir to the first affinity chromatography matrix and wherein the first affinity chromatography matrix is operably connected to an output vessel via a second operable connection; and b) a second affinity chromatography matrix including a second binding agent immobilized thereon, which second binding agent specifically binds to a second cell surface marker present on a second cell, wherein the first affinity chromatography matrix is operably connected via a third operable connection to the second affinity chromatography matrix, said third operable connection capable of permitting passage of cells having passed through the first affinity chromatography matrix and not bound to the first binding agent to the second affinity chromatography matrix, and the second affinity chromatography matrix is operably connected via a fourth operable connection to the output vessel, the fourth operable connection capable of permitting passage of cells having bound to and been eluted from the first and/or second affinity chromatography matrix, and the second affinity chromatography matrix is operably linked, via a fifth operable connection, to a waste vessel, the fifth operable connection capable of permitting passage of cells having passed through the first affinity chromatography matrix and not bound to the first binding agent and having passed through the second affinity chromatography matrix and not bound to the second binding agent;

c) the output vessel; and d) the waste vessel, wherein the system is configured to permit, within the closed system, collection of, in the output vessel in a single composition, (i) cells having bound and been recovered from the first affinity chromatography matrix and (ii) cells having passed through and not bound to the first affinity chromatography matrix and having bound and been recovered from the second chromatography matrix.

101. The closed apparatus of embodiment 100, wherein one or more of said operable connections contains tubing connecting the storage reservoir, first affinity chromatography matrix, second affinity chromatography matrix and/or culture vessel.

102. The closed apparatus of embodiment 101, wherein the tubing is connected to a stopcock, valve or clamp.

103. The closed apparatus system of any of embodiments 100-102, wherein:

(a) the first affinity chromatography matrix is one of a CD4+ affinity chromatography matrix or a CD8+ affinity chromatography matrix; and (b) the second affinity chromatography matrix is the other of the CD4+ affinity chromatography matrix or the CD8+ affinity chromatography matrix.

104. The closed apparatus system of any of embodiments 100-103, further including:

d) a third affinity chromatography matrix including a third binding agent immobilized thereon, which binding agent specifically binds to a third cell surface marker, whereby the third binding agent is capable of binding cells expressing the third cell surface marker, wherein the third operable connection further operably connects the third affinity chromatography matrix to the first matrix and a sixth operable connection operably connects the third affinity chromatography matrix to the output container, such that the sixth operable connection is capable of permitting passage of cells having bound to and been recovered from the first matrix and having bound to and been recovered from the third matrix to the output container, and the fifth operable connection further operably connects the third affinity chromatography matrix to the waste container, such that the fifth operable connection is capable of permitting cells having passed through and not bound to the third column to the waste container.

105. The closed apparatus system of any of embodiments 100-103, further including:

d) a third affinity chromatography matrix including a third binding agent immobilized thereon, which binding agent specifically binds to a third cell surface marker, whereby the third affinity chromatography matrix is capable of binding cells expressing the third cell surface marker, wherein the second operable connection further operably connects the third affinity chromatography matrix to the first matrix and to the output container, such that the second operable connection is capable of permitting cells having bound to and been recovered from the first matrix and having bound to and been recovered from the third matrix to the output container.

106. The closed apparatus system of embodiment 104 or 105, wherein:

the first affinity chromatography matrix includes a biding agent that specifically binds CD8;

the second affinity chromatography matrix includes a binding agent that specifically binds CD4; and the third affinity chromatography matrix includes a binding agent that specifically binds a marker expressed on central memory T ($T_{CM}$) cells.

107. The closed apparatus system of embodiment 106, wherein the binding agent of the third affinity chromatography matrix selectively binds to a cell surface marker selected from among CD62L, CD45RA, CD45RO, CCR7, CD27, CD127, and CD44.

108. The closed apparatus system of any of embodiments 100-107, wherein one or more or all of the affinity chromatography matrices are further operably connected to an elution buffer reservoir including one or more competition reagents.

109. The closed apparatus system of any of embodiments 100-107, wherein the competition reagent is one or more of the group consisting of biotin, a biotin analog, and a peptide capable of binding to the chromatography matrix.

110. The closed apparatus system of any of embodiments 100-107, wherein one or more or all of the third, fourth, or sixth operable connections further includes a competition agent removal chamber.

111. The closed apparatus system of embodiment 110, wherein the competition agent removal chamber further contains a binding reagent.

112. The closed apparatus system of embodiment 111, wherein the binding reagent includes one or more of the group consisting of streptavidin, a streptavidin analog or mutein, avidin and an avidin analog or mutein.

113. The closed apparatus system of any of embodiments 100-112, wherein one or more or all of the binding agents is an antibody.

114. The closed apparatus system of any of embodiments 100-112, wherein the one or more or all of the binding agents is reversibly bound to the affinity chromatography matrix.

VI. Examples

The following examples are included for illustrative purposes only and are not intended to limit the scope of the invention.

Example 1: Generation of a CD4+ and CD8+ T Cell Composition Using a Single Process Stream by Immunomagnetic Separation for Genetic Engineering and Adoptive Cell Therapy In an exemplary method, a $CD4^+$ T cell population and a $CD8^+$ T cell population, enriched for central memory T cells, are isolated from an apheresis product sample, and subsequently incubated and engineered, followed by administration to a subject. The isolation procedure is carried out using a single process stream by immunomagnetic separation using the CliniMACS® Prodigy system. The process is streamlined as compared to other methods, in which $CD4^+$ cells are separated from a first apheresis fraction and $CD8^+$ cells are separated and further depleted/enriched, from a second apheresis fraction, using a CliniMACS® Prodigy device and three separate tubing sets.

The streamlined process is performed using one tubing set for isolation of the $CD4^+$ and $CD8^+$ cell populations, without transferring the cell populations from one vessel (e.g., tubing set) to another.

The $CD4^+$ cell population is isolated by incubating an apheresis sample with a CliniMACS® CD4 reagent. The cells are then separated by the CliniMACS® Prodigy device set to run an enrichment program, and both cell fractions (i.e., the immunomagnetically selected enriched $CD4^+$ cell fraction and the flow-through cell fraction) are retained. The enriched (positive) fraction is an isolated $CD4^+$ T cell population. A population of $CD8^+$ T cells is isolated by incubating the flow-through (negative) fraction with a CliniMACS® CD14 reagent and a CliniMACS® CD45RA reagent or CD19 reagent. The CliniMACS® Prodigy device is set to run a depletion program. The cell/reagent mixture then is separated by the CliniMACS® Prodigy device using the same tubing set used in the first separation step. The flow-through (negative) fraction from which $CD14^+$/$CD45RA^+$ or CD14+/CD19+ cells have been depleted is incubated with CliniMACS® CD62L reagent. The cell/reagent mixture is separated using the CliniMACS® Prodigy device running an enrichment program using the same tubing set. The positive fraction is an isolated $CD8^+$ cell population enriched for central memory cells.

The isolated CD4+ and CD8+ populations are combined in the same culture vessel in a culture-initiating composition at a culture initiation ratio. The culture-initiation ratio is designed to achieve a particular desired output ratio, or a ratio that is within a certain range of tolerated error of such a desired output ratio, following the incubation and/or engineering steps, or designed to do so a certain percentage of the time. The cells are incubated under stimulating conditions, such as using anti-CD3/anti-CD28 beads in the presence IL-2 (100 IU/mL) for 72 hours at 37° C., within the Prodigy system.

The cell composition is optionally periodically assessed and/or adjusted at one or more times subsequent to the initiation of the incubation or culture, such as at a time during the incubation. Assessment includes measuring proliferation rate, measuring degree of survival, determining phenotype, e.g., expression of one or more surface or intracellular markers, such as proteins or polynucleotides, and/or adjusting the composition or vessel for temperature, media component(s), oxygen or carbon dioxide content, and/or presence or absence or amount or relative amount of one or more factors, agents, components, and/or cell types, including subtypes.

Cells so-incubated then are genetically engineered, by introducing into the cells recombinant genes for expression of recombinant antigen receptors, such as chimeric antigen receptors (CARs) or recombinant TCRs. The introduction is performed in the contained environment within the CliniMACS® Prodigy device, with $CD4^+$ and $CD8^+$ cells present in the same composition and vessel. The method results in an output composition with engineered $CD4^+$ and $CD8^+$ T cells.

Example 2: Generation of a CD4+ and CD8+ T Cell Composition by Sequential Purification in a Closed System This example demonstrates an exemplary method of enriching or selecting for a CD4+ T cell population and a CD8+ T cell population from an apheresis product sample obtained from a subject. The process is performed using a closed system with multiple chromatography columns for sequential positive selection of the CD4+ and CD8+ T cell populations from the same starting sample.

A. Enrichment for CD4+ T Cell Population and CD8+ T Cell Population

In the exemplary process, depicted in FIG. 1A, a series of immunochromatographic selection columns and removal columns are arranged in a closed apparatus 14 operably connected to each other and a peristaltic pump 8 through various tubing lines and valves 13 to control flow of liquid phase.

The first selection column 1 contains a chosen volume of an affinity chromatography matrix 3, such as an agarose resin, such as a resin as described in published U.S. Patent Appl. No. US2015/0024411 for the isolation of T cells, such as one with an exclusion limit designed to be greater than the size of a T cell, such as an agarose as obtained from Agarose Beads Technologies, Madrid, Spain, with a reduced exclusion size compared to Superflow™ Agarose, which has an exclusion size of $6 \times 10^6$ Daltons. The matrix in the first column is bound to multimers of Strep-Tactin® (e.g. containing a streptavidin mutant set forth in any of SEQ ID NO:12, 13, 15 or 16, IBA GmbH, Germany or as described in International Published PCT Appl. Nos. WO 2014/076277). The second selection column 2 contains a chosen volume of an affinity chromatography matrix 4, such as an agarose resin, such as a resin as described above, which is also bound to multimers of Strep-Tactin®.

A reservoir containing an anti-CD8 Fab fragment 18 is loaded to run through the pump 8, tubing, and valves 13 such that the anti-CD8 Fab is applied to the first selection column 1, whereby the anti-CD8 Fab becomes immobilized on the Strep-Tactin® on the affinity matrix 3 with a Twin Strep-tag® (e.g. set forth in SEQ ID NO: 10; IBA GmbH) in the Fab Fragment, which is fused to the carboxy-terminus of its heavy chain (see e.g. published U.S. Patent Appl. No. US2015/0024411). In some embodiments, a washing buffer from a washing buffer reservoir 6, such as phosphate buffered saline (PBS) containing 0.5% bovine serum albumin, human serum albumin, or recombinant human serum albumin, is loaded to run through the first selection column via operably coupled tubing. The flow-through is directed to the waste container 10 via valves 13 operably connecting the first selection column and waste container. In some embodiments, the washing step is repeated a plurality of times.

A reservoir containing an anti-CD4 Fab fragment 19 is loaded to run through the pump 8, tubing, and valves 13 such that the anti-CD4 Fab is applied to the second selection column 2, whereby the anti-CD8 Fab becomes immobilized on the Strep-Tactin® on the affinity matrix 4 with a Twin Strep-tag®. In some embodiments, a washing buffer from a washing buffer reservoir 6 is run through the second selection column via operably coupled tubing. The flow-through is directed to the waste container 10 via valves 13 operably connecting the second selection column and waste container. In some embodiments, the washing step is repeated a plurality of times.

The volume of affinity matrix reagent contained in the first selection column and the second selection column can be the same or different, and can be chosen based on the desired yield of the selection and/or desired ratio of CD4+ cells to CD8+ cells following selection. The volume so chosen is based on an assumption of an average yield of $1 \times 10^8$ cells being capable of selection per each 1 mL volume of filled column. In one exemplary process, the column volumes are the same, for example, using a 2 mL volume for the column for the anti-CD8 Fab fragment and a 2 mL column for the anti-CD4 Fab fragment. The column length and/or column diameter can be chosen to fit the desired volume, for example, to achieve a desired culture-initiation ratio of CD4+ cells to CD8+ cells. In some embodiments, to accommodate the volume of affinity matrix, a plurality of columns having immobilized thereto the same Fab reagent can be added directly in series and operably connected to each other via a tubing line.

To achieve selection of cells, an apheresis sample is applied to the first selection column 1, whereby CD8+ T cells, if present in the sample, remain bound to the resin 3 of the first column, as unselected cells (containing CD8− cells) pass through the column. The number of cells in the starting sample used in some examples is chosen to be above the number of cells to be selected based on the combined volume of the matrices, such as an amount greater than the capacity of the column for each selection (e.g. an amount having greater than 200 million CD8+ cells and greater than 200 million CD4+ cells, e.g., greater by at least about 10% or 20% or greater). The flow-through containing unselected cells (negative fraction) then passes from the first column to a second selection column 2 via operably coupled tubing. CD4+ T cells remain bound to the resin 4 in the second column. The flow through containing fluid and further unselected cells (negative cells) is directed to a waste container 10 via valves 13 operably connecting the second selection column and waste container.

In some embodiments, the first selection column can alternatively be an anti-CD4 affinity chromatography matrix and the second selection column can be an anti-CD8 affinity chromatography matrix.

From a washing buffer reservoir 6, a washing buffer is run through the first column and the second column via operably coupled tubing. The flow-through containing any cells that are washed from the first and second columns is directed to the waste container 10 via valves 13 operably connecting the second selection column and waste container. In some embodiments, the washing step is repeated a plurality of times.

From an elution buffer reservoir 7, a buffer containing an eluent, such as low concentrations of biotin or an analog thereof, for example 2.5 mM desthiobiotin, is loaded to run through the first column and the second column via operably coupled tubing. In some embodiments, the eluent contains cell culture media. The flow-through, containing enriched CD4+ and CD8+ cells and residual biotin or analog, is directed to a removal chamber 9 to remove biotin or an analog thereof. The removal chamber 9 is a column of Superflow™ Sepharose® beads having Strep-Tactin® immobilized thereto with a volume sufficient to remove biotin or a biotin analog from the sample, such as a column having a bed volume of 6 mL with a binding capacity of 300 nanomol biotin/mL. The flow-through containing enriched cells positively selected for CD4+ and CD8+ is directed to a culture vessel 12, such as a bag, via valves operably connecting the removal chamber 9 and culture vessel. In some embodiments, the elution step is repeated.

In some embodiments, after performing the elution step, an activation buffer containing a T-cell activation reagent (e.g. anti-CD3, anti-CD28, IL-2, IL-15, IL-7, and/or IL-21) replaces the wash buffer and is directed through the removal chamber and flow through directed to the culture vessel. The positive fraction collected in the culture vessel is an isolated and combined CD4+ and CD8+ cell population.

B. Enrichment for a CD4+ T Cell Population and a CD8+ T Cell Population, Enriched for Cells Expressing a Marker on Central Memory T ($T_{CM}$) Cells In the exemplary process, depicted in FIG. 1B, a series of immunochromatographic selection columns and removal columns are arranged in a closed apparatus 14 operably connected to each other and a peristaltic pump 8 through various tubing lines and valves 13 to control flow of liquid phase.

The first selection column 1 and second selection column 2 are the same as described above with respect to Example 2A. In addition, the process further includes a third selection column 15 that contains a chosen volume of an affinity matrix 17, such as an agarose resin, such as a resin as described in published U.S. Patent Appl. No. US2015/0024411 for the isolation of T cells, such as one as described above in Example 2A.

The anti-CD8 Fab and the anti-CD4 Fab are applied to the first column and second column, respectively, as described in Example 2A. A reservoir containing a further Fab fragment against a marker expressed on central memory T ($T_{CM}$) cells 20, such as one of CD28, CD62L, CCR7, CD27 or CD127, is loaded to run through the pump 8, tubing, and valves 13 such that the further Fab is applied to the third selection column 15, whereby the further Fab becomes conjugated to the Strep-Tactin® on the affinity matrix 17 with a Twin Strep-tag® (SEQ ID NO: 10; IBA GmbH) in the Fab Fragment, which is fused to the carboxy-terminus of its heavy chain, as described in Example 2A. In some embodiments, a washing buffer, as described in Example 2A, is loaded to run through the third selection column via operably coupled tubing. The flow-through is directed to the waste container 10 via valves 13 operably connecting the third selection column and waste container. In some embodiments, the washing step is repeated a plurality of times.

The volume of affinity matrix reagent contained in the first selection, second and/or third selection columns can be the same or different, and can be chosen based on the desired yield of the selection and/or desired ratio of CD4+ cells to CD8+ cells enriched for cells expressing a marker expressed on central memory T ($T_{CM}$) cells following selection. The volume so-chosen is based on the assumption of an average yield of $1 \times 10^8$ cells being capable of selection per each 1 mL volume of filled column. Also, for a particular chosen culture-initiation ratio, for example, a culture-initiation ratio of 1:1 of CD4+ cells to a population containing CD8+ cells enriched for a marker expressed on central memory T ($T_{CM}$) cells (e.g. a population of CD8+ cells enriched based on further selection for one of CD28, CD62L, CCR7, CD27 or CD127), the volume of the matrix for selecting the parent population of the enriched population, e.g. the CD8$^+$ cells, is larger in comparison to the matrix used for selecting the other of the CD4+ or CD8+ T cell population, e.g. the CD4+ population. The amount or extent in which the volume of the matrix used to select for the parent population of the further enriched population, e.g. the matrix containing anti-CD8 Fab fragment, is greater than the volume of the other matrix or other matrices is chosen based on the fraction or percentage of the further enriched population of cells in the sample (e.g. CD8+/CD28+, CD8+/CD62L+, CD8+/CCR7+, CD8+/CD27+ or CD8+/CD127+) compared to the fraction or percentage of the parent population, e.g. CD8+ cells, present in the sample. This can be estimated based on averages among patients or healthy donors, or it can be measured for a given patient on which selection is being performed prior to determining the size of the columns to use.

In one exemplary process, the column volumes used in the process are, for example, a 2 mL column with anti-CD4 Fab fragments, a 6 mL column with anti-CD8 Fab fragments, and a 2 mL column with anti-CD62L Fab fragments. The column length and/or column diameter can be chosen to fit the desired volume, for example, to achieve a desired culture-initiation ratio of CD4+ cells to CD8+ cells enriched for cells expressing a marker expressed on central memory T ($T_{CM}$) cells, e.g.CD8+/CD28+, CD8+/CD62L+, CD8+/CCR7+, CD8+/CD27+ or CD8+/CD127+ cells. In some embodiments, to accommodate the volume of affinity matrix, a plurality of columns having immobilized thereto the same Fab reagent can be added directly in series and operably connected to each other via a tubing line.

To achieve selection of cells, an apheresis sample is applied to the first selection column 1, whereby CD8+ T cells, if present in the sample, remain bound to the resin of the first column as unselected cells (containing CD8− cells) pass through the column. The number of cells in the starting sample used in some examples is chosen to be above the number of cells to be selected based on the combined volume of the matrices such as an amount greater than the capacity of the column for each selection (e.g. an amount having greater than 200 million CD8+/CD62L+ cells and greater than 200 million CD4+ cells, e.g. greater by at least about 10% or 20% or greater). The flow-through containing unselected cells (negative fraction) is directed to pass to the second column 2 via a valve 13 operably connecting the first and second column. CD4+ T cells remain bound to the resin in the second column. The flow-through containing fluid and further unselected cells (negative cells) is directed to a first waste container 10 via valves 13 operably connecting the second selection column and negative fraction container.

From a washing buffer reservoir 6, a washing buffer, such as described in Example 2A, is loaded to run through the first column and the second column via a valve and tubes operably connecting the columns. The flow-through containing any cells that are washed from the first and second columns is directed to the waste container 10 via valves 13 operably connecting the second selection column and waste container. In some embodiments, the washing step is repeated a plurality of times.

From an elution buffer reservoir 7, a buffer containing an eluent, such as biotin or an analog thereof, for example 2.5 mM desthiobiotin, is loaded to run through the second column 2 via valves 13 and tubing operably connecting the elution buffer reservoir and second column. In some embodiments, the elution buffer contains cell culture media. The flow-through, containing enriched CD4+ cells and residual biotin, is directed to a removal chamber 9 to remove biotin, such as described in Example 2A, which is operably connected to the second column via a valve 13 and tubing. The flow-through containing enriched cells positively selected for CD4+ is directed to a culture vessel 12, such as a bag, via valves 13 operably connecting the removal chamber 9 and culture vessel. In some embodiments, the elution step is repeated. In some embodiments, after performing the elution step, an activation buffer containing a T-cell activation reagent (e.g. anti-CD3, anti-CD28, IL-2, IL-15, IL-7, and/or IL-21) replaces the wash buffer and is directed via valves and tubing from the washing buffer reservoir to the second column, removal chamber and into the culture vessel. The positive fraction collected in the culture vessel is an isolated CD4+ cell population.

From an elution buffer reservoir 7, a buffer containing an eluent, such as biotin, is loaded to run through the first column 1 via a valve 13 and tubing operably connecting the elution buffer reservoir and first column. In some embodiments, the elution buffer contains cell culture media. The flow-through, containing enriched CD8+ cells and residual biotin or an analog thereof, is directed to a removal chamber 9 to remove biotin or a biotin analog, such as described in Example 2A, which is operably connected to the first column via a valve 13 and tubing. The flow-through containing enriched cells positively selected for CD8+ is directed to pass to a third column 15 via a valve 13 operably connecting the removal chamber 9 and third column. A CD62L+ subset of the CD8+ cells remain bound to the resin in the third column. The flow through containing fluid and further unselected cells (negative cells) is directed to a second waste container 11 via valves 13 operably connecting the third selection column and second waste container.

From a washing buffer reservoir 6, a washing buffer, such as described in Example 2A, is loaded to run through the third column 15 via valves 13 and tubing operably connecting the wash buffer reservoir and third column. The flow through containing any cells that are washed from the third column is directed to the second waste container 11 via valves 13 operably connecting the third selection column and second waste container. In some embodiments, the washing step is repeated a plurality of times.

From an elution buffer reservoir 7, a buffer containing an eluent, such as biotin or an analog thereof, for example 2.5 mM desthiobiotin, is loaded to run through the third column 15 via a valve 13 and tubing operably connecting the elution buffer reservoir and third column. In some embodiments, the elution buffer contains cell culture media. The flow-through, containing CD8+ cells enriched for central memory T ($T_{CM}$) cells expressing one of CD28, CD62L, CCR7, CD27 or CD127, and residual biotin or analog thereof, is directed to a removal chamber 9 to remove biotin or a biotin analog, such as described in Example 2A, which is operably connected to the third column via a valve 13 and tubing. The flow-through containing enriched T cell memory cells positively selected for CD8 and a marker expressed on central memory T ($T_{CM}$) cells, such as one of CD28, CD62L, CCR7, CD27 or CD127, is directed to the culture vessel 12, such as a bag, via valves 13 operably connecting the removal chamber 9 and culture vessel. In some embodiments, the culture vessel contains a T-cell activation reagent, a cell culture media, or both. In some embodiments, the elution step is repeated. In some embodiments, after performing the elution step, an activation buffer containing a T-cell activation reagent (e.g. anti-CD3, anti-CD28, IL-2, IL-15, IL-7, and/or IL-21) replaces the wash buffer and is directed via valves and tubing from the washing buffer reservoir to the first and/or third column, removal chamber and into the culture vessel. The positive fraction containing CD8+ cells and cells positive for a marker on central memory T ($T_{CM}$) cells, such as one of CD28, CD62L, CCR7, CD27 or CD127, is collected in the culture vessel with the CD4+ positive fraction previously collected. In some embodiments, the steps of the process can be performed in a different order, such as by first enriching for cells containing CD8+ cells and cells positive for a marker on central memory T ($T_{CM}$) cells, such as one of CD28, CD62L, CCR7, CD27 or CD127 before enriching CD4+ cells.

Example 3: Generation of a CD4+ and CD8+ T Cell Composition by Sequential Purification in a Closed System for Use in Genetic Engineering and Adoptive Cell Therapy This example demonstrates a procedure for selecting and generating a composition of cells containing CD4+ and CD8+ T cells, such as CD4+ and CD8+ T cells present in a culture-initiation ratio, for incubation/activation and transduction in methods associated with genetic engineering of cells for use in connection with adoptive cell therapy.

A composition of cells generated by selection of CD4+ and CD8+ cells, performed as described in either Example 2A (CD4+ and CD8+) or Example 2B (CD4+ and CD8+ enriched for CD62L+), is incubated under stimulating conditions, such as using anti-CD3/anti-CD28 in the presence IL-2 (100 IU/mL), for example, for 72 hours at 37° C. Stimulated cells then are genetically engineered by introducing into the cells recombinant genes for expression of recombinant antigen receptors, such as chimeric antigen receptors (CARs) or recombinant TCRs, for example, by viral transduction. In some embodiments, following the introduction, cells are further incubated, generally at 37 degrees C., for example, to allow for cell expansion.

The method results in an output composition with engineered CD4+ and CD8+ T cells. In some embodiments, based on the chosen volume of the selection columns, the ratio of CD4+ to CD8+ cells in the composition that is incubated under the stimulating conditions prior to engineering (culture-initiation ratio) results in a particular desired output ratio of CD4+ to CD8+ cells or of engineered CD4+ cells to engineered CD8+ cells, or such a ratio that is within a certain range of tolerated error of such a desired output ratio, following the incubation, stimulation and/or engineering steps. In some embodiments, such a desired output ratio or ratio within the range of tolerated error is achieved a certain tolerated percentage of the time.

Example 4: Selection of Cells Using Sub-Optimal Yield Concentrations of Fab-Coated Surfaces Human apheresis-derived PBPC samples, at a range of different cell numbers, were incubated in a single composition with magnetic microbeads conjugated to anti-CD4 Fabs and magnetic microbeads conjugated to anti-CD8 Fabs, with gentle mixing for about 30 minutes. This incubation was followed by elution of non-selected cells, and recovery using magnetic field carried out as described above. Incubation using between 0.05 and 1.5 mL of each of microbead reagent per million cells produced low yields of CD4+ or CD8+ cells, respectively (cells recovered for the respective selection compared with positive cells in the incubation), which in this study were generally in the range of 15-70%). On average, greater yields were observed at higher concentrations of reagents per cell using such sub-optimal yield concentrations.

Accordingly, in one example, a selection is carried out, in which PBMCs are incubated with suboptimal concentrations per cell number of beads coupled to a CD4-binding and beads coupled to a CD8-binding agent, and cells recovered using a magnetic field. Based on the observed relationship between concentration of the reagent per cell and yield for the beads used, one or the other of the CD4-binding or CD8-binding reagent is included at a higher concentration (e.g., higher number of Cd4 or CD8 binding molecules included per cell), thereby producing an output ratio of $CD8^+:CD4^+$ cells following selection, which is greater than or less than 1, such as 1.5:1 or 2:1 or 3:1 or 1:1.5, 1:2, or 1:3. The output ratio may be selected based on the desired ratio of CD8 vs. CD4 cells in a composition containing engineered cells to be produced following one or more additional steps, such as activation, transduction, and/or expansion.

The invention claimed is:

1. A method of treating systemic lupus erythematosus (SLE) in a human subject, the method comprising intravenously administering a dose of genetically engineered CD4+ and CD8+ T cells to a human subject with SLE, wherein:
the CD4+ and CD8+ T cells of the dose are at a ratio, wherein the ratio is between at or about 5:1 and at or about 1:3;
the dose of genetically engineered CD4+ and CD8+ T cells is between at or about $5\times10^6$ to $500\times10^6$ cells; and
the CD4+ and CD8+ T cells are genetically engineered with a chimeric antigen receptor (CAR), wherein the CAR comprises an scFv that binds CD19, a transmembrane domain, and an intracellular signaling domain comprising a 4-1BB costimulatory signaling domain and a CD3zeta signaling domain.

2. A method of treating systemic lupus erythematosus (SLE) in a human subject, the method comprising intravenously administering a dose of genetically engineered CD4+ and CD8+ T cells to a human subject with SLE, wherein:
the CD4+ and CD8+ T cells of the dose are at a ratio, wherein the ratio is between at or about 5:1 and at or about 1:3;
the dose of genetically engineered CD4+ and CD8+ T cells is between at or about $5\times10^6$ to $500\times10^6$ cells; and
the CD4+ and CD8+ T cells are genetically engineered with a chimeric antigen receptor (CAR), wherein the CAR comprises an scFv that binds CD19, a transmembrane domain, and an intracellular signaling domain comprising a CD28 costimulatory signaling domain and a CD3zeta signaling domain.

3. The method of claim 1, wherein the dose of CD4+ and CD8+ T cells is between at or about $5\times10^6$ to $25\times10^6$ cells.

4. The method of claim 1, wherein the dose of CD4+ and CD8+ T cells is at or about $5\times10^6$ cells.

5. The method of claim 1, wherein the dose of CD4+ and CD8+ T cells is at or about $10\times10^6$ cells.

6. The method of claim 1, wherein the dose of CD4+ and CD8+ T cells is between $20\times10^6$ cells and $60\times10^6$ cells.

7. The method of claim 1, wherein the dose of CD4+ and CD8+ T cells is between $20\times10^6$ cells and $90\times10^6$ cells.

8. The method of claim 1, wherein the dose of CD4+ and CD8+ T cells is between $20\times10^6$ cells and $250\times10^6$ cells.

9. The method of claim 1, wherein the dose of CD4+ and CD8+ T cells is between $30\times10^6$ cells and $90\times10^6$ cells.

10. The method of claim 1, wherein the percentage of CD4+ and CD8+ T cells in the dose is at least about 90%.

11. The method of claim 8, wherein the percentage of CD4+ and CD8+ T cells in the dose is at least about 90%.

12. The method of claim 2, wherein the dose of CD4+ and CD8+ T cells is between at or about $5\times10^6$ to $25\times10^6$ cells.

13. The method of claim 2, wherein the dose of CD4+ and CD8+ T cells is at or about $5\times10^6$ cells.

14. The method of claim 2, wherein the dose of CD4+ and CD8+ T cells is at or about $10\times10^6$ cells.

15. The method of claim 2, wherein the dose of CD4+ and CD8+ T cells is between $20\times10^6$ cells and $60\times10^6$ cells.

16. The method of claim 2, wherein the dose of CD4+ and CD8+ T cells is between $20\times10^6$ cells and $90\times10^6$ cells.

17. The method of claim 2, wherein the dose of CD4+ and CD8+ T cells is between $20\times10^6$ cells and $250\times10^6$ cells.

18. The method of claim 2, wherein the dose of CD4+ and CD8+ T cells is between $30\times10^6$ cells and $90\times10^6$ cells.

19. The method of claim 2, wherein the percentage of CD4+ and CD8+ T cells in the dose is at least about 90%.

20. The method of claim 17, wherein the percentage of CD4+ and CD8+ T cells in the dose is at least about 90%.

\* \* \* \* \*

SEQUENCE LISTING

```
Sequence total quantity: 19
SEQ ID NO: 1            moltype =   length =
SEQUENCE: 1
000

SEQ ID NO: 2            moltype = AA  length = 4
FEATURE                 Location/Qualifiers
REGION                  1..4
                        note = Synthetic
REGION                  1..4
                        note = Streptavidin-binding peptide
source                  1..4
                        mol_type = protein
                        organism = synthetic construct
SEQUENCE: 2
HPQF                                                                        4

SEQ ID NO: 3            moltype = AA  length = 8
FEATURE                 Location/Qualifiers
REGION                  1..8
                        note = Synthetic
REGION                  1..8
                        note = Streptavidin-binding peptide
VARIANT                 1
                        note = Xaa = Trp, Lys or Arg
```

```
VARIANT                 2
                        note = Xaa = any amino acid
VARIANT                 7
                        note = Xaa = Gly or Glu
VARIANT                 8
                        note = Xaa = Gly, Lys or Arg
source                  1..8
                        mol_type = protein
                        organism = synthetic construct
SEQUENCE: 3
XXHPQFXX                                                                8

SEQ ID NO: 4            moltype = AA  length = 8
FEATURE                 Location/Qualifiers
REGION                  1..8
                        note = Synthetic
REGION                  1..8
                        note = Streptavidin-binding peptide
VARIANT                 2
                        note = Xaa = any amino acid
VARIANT                 7
                        note = Xaa = Gly or Glu
VARIANT                 8
                        note = Xaa = Gly, Lys or Arg
source                  1..8
                        mol_type = protein
                        organism = synthetic construct
SEQUENCE: 4
WXHPQFXX                                                                8

SEQ ID NO: 5            moltype = AA  length = 8
FEATURE                 Location/Qualifiers
REGION                  1..8
                        note = Synthetic
REGION                  1..8
                        note = Streptavidin-binding peptide
source                  1..8
                        mol_type = protein
                        organism = synthetic construct
SEQUENCE: 5
WRHPQFGG                                                                8

SEQ ID NO: 6            moltype = AA  length = 8
FEATURE                 Location/Qualifiers
REGION                  1..8
                        note = Synthetic
REGION                  1..8
                        note = Strep-tag (registered trademark) II
source                  1..8
                        mol_type = protein
                        organism = synthetic construct
SEQUENCE: 6
WSHPQFEK                                                                8

SEQ ID NO: 7            moltype = AA  length = 28
FEATURE                 Location/Qualifiers
REGION                  1..28
                        note = Synthetic
REGION                  1..28
                        note = Sequential modules of streptavidin-binding peptide
VARIANT                 9..20
                        note = Xaa at positions 9-20 may be any amino acid and 4 of
                         them may be absent
source                  1..28
                        mol_type = protein
                        organism = synthetic construct
SEQUENCE: 7
WSHPQFEKXX XXXXXXXXXX WSHPQFEK                                          28

SEQ ID NO: 8            moltype = AA  length = 28
FEATURE                 Location/Qualifiers
REGION                  1..28
                        note = Synthetic
REGION                  1..28
                        note = Sequential modules of streptavidin-binding peptide
VARIANT                 9..12
                        note = These amino acids may be absent
source                  1..28
                        mol_type = protein
```

```
                         organism = synthetic construct
SEQUENCE: 8
WSHPQFEKGG GSGGGSGGGS WSHPQFEK                                        28

SEQ ID NO: 9             moltype = AA   length = 30
FEATURE                  Location/Qualifiers
REGION                   1..30
                         note = Synthetic
REGION                   1..30
                         note = Twin-Strep-Tag
source                   1..30
                         mol_type = protein
                         organism = synthetic construct
SEQUENCE: 9
SAWSHPQFEK GGGSGGGSGG GSWSHPQFEK                                      30

SEQ ID NO: 10            moltype = AA   length = 30
FEATURE                  Location/Qualifiers
REGION                   1..30
                         note = Synthetic
REGION                   1..30
                         note = Twin-Strep-Tag
source                   1..30
                         mol_type = protein
                         organism = synthetic construct
SEQUENCE: 10
SAWSHPQFEK GGGSGGGSGG SAWSHPQFEK                                      30

SEQ ID NO: 11            moltype = AA   length = 159
FEATURE                  Location/Qualifiers
REGION                   1..159
                         note = Streptavidin
source                   1..159
                         mol_type = protein
                         organism = Streptomyces avidinii
SEQUENCE: 11
DPSKDSKAQV SAAEAGITGT WYNQLGSTFI VTAGADGALT GTYESAVGNA ESRYVLTGRY     60
DSAPATDSG TALGWTVAWK NNYRNAHSAT TWSGQYVGGA EARINTQWLL TSGTTEANAW     120
KSTLVGHDTF TKVKPSAASI DAAKKAGVNN GNPLDAVQQ                           159

SEQ ID NO: 12            moltype = AA   length = 159
FEATURE                  Location/Qualifiers
REGION                   1..159
                         note = Mutein Streptavidin Val44-Thr45-Ala46-Arg47
source                   1..159
                         mol_type = protein
                         organism = Streptomyces avidinii
SEQUENCE: 12
DPSKDSKAQV SAAEAGITGT WYNQLGSTFI VTAGADGALT GTYVTARGNA ESRYVLTGRY     60
DSAPATDSG TALGWTVAWK NNYRNAHSAT TWSGQYVGGA EARINTQWLL TSGTTEANAW     120
KSTLVGHDTF TKVKPSAASI DAAKKAGVNN GNPLDAVQQ                           159

SEQ ID NO: 13            moltype = AA   length = 159
FEATURE                  Location/Qualifiers
REGION                   1..159
                         note = Mutein Streptavidin Ile44-Gly45-Ala-46-Arg47
source                   1..159
                         mol_type = protein
                         organism = Streptomyces avidinii
SEQUENCE: 13
DPSKDSKAQV SAAEAGITGT WYNQLGSTFI VTAGADGALT GTYIGARGNA ESRYVLTGRY     60
DSAPATDSG TALGWTVAWK NNYRNAHSAT TWSGQYVGGA EARINTQWLL TSGTTEANAW     120
KSTLVGHDTF TKVKPSAASI DAAKKAGVNN GNPLDAVQQ                           159

SEQ ID NO: 14            moltype = AA   length = 126
FEATURE                  Location/Qualifiers
REGION                   1..126
                         note = Minimal streptavidin
source                   1..126
                         mol_type = protein
                         organism = Streptomyces avidinii
SEQUENCE: 14
EAGITGTWYN QLGSTFIVTA GADGALTGTY ESAVGNAESR YVLTGRYDSA PATDGSGTAL     60
GWTVAWKNNY RNAHSATTWS GQYVGGAEAR INTQWLLTSG TTEANAWKST LVGHDTFTKV    120
KPSAAS                                                               126

SEQ ID NO: 15            moltype = AA   length = 126
FEATURE                  Location/Qualifiers
REGION                   1..126
```

```
                            note = Mutein Streptavidin Val44-Thr45-Ala46-Arg47
source                      1..126
                            mol_type = protein
                            organism = Streptomyces avidinii
SEQUENCE: 15
EAGITGTWYN QLGSTFIVTA GADGALTGTY VTARGNAESR YVLTGRYDSA PATDGSGTAL    60
GWTVAWKNNY RNAHSATTWS GQYVGGAEAR INTQWLLTSG TTEANAWKST LVGHDTFTKV   120
KPSAAS                                                              126

SEQ ID NO: 16               moltype = AA  length = 126
FEATURE                     Location/Qualifiers
REGION                      1..126
                            note = Mutein Streptavidin Ile44-Gly45-Ala-46-Arg47
source                      1..126
                            mol_type = protein
                            organism = Streptomyces avidinii
SEQUENCE: 16
EAGITGTWYN QLGSTFIVTA GADGALTGTY IGARGNAESR YVLTGRYDSA PATDGSGTAL    60
GWTVAWKNNY RNAHSATTWS GQYVGGAEAR INTQWLLTSG TTEANAWKST LVGHDTFTKV   120
KPSAAS                                                              126

SEQ ID NO: 17               moltype = AA  length = 28
FEATURE                     Location/Qualifiers
REGION                      1..28
                            note = Synthetic
REGION                      1..28
                            note = Twin Strep-tag
source                      1..28
                            mol_type = protein
                            organism = synthetic construct
SEQUENCE: 17
WSHPQFEKGG GSGGGSGGGS WSHPQFEK                                       28

SEQ ID NO: 18               moltype = AA  length = 24
FEATURE                     Location/Qualifiers
REGION                      1..24
                            note = Synthetic
REGION                      1..24
                            note = Twin Strep-tag
source                      1..24
                            mol_type = protein
                            organism = synthetic construct
SEQUENCE: 18
WSHPQFEKGG GSGGGSWSHP QFEK                                           24

SEQ ID NO: 19               moltype = AA  length = 28
FEATURE                     Location/Qualifiers
REGION                      1..28
                            note = Synthetic
REGION                      1..28
                            note = Twin Strep-tag
source                      1..28
                            mol_type = protein
                            organism = synthetic construct
SEQUENCE: 19
WSHPQFEKGG GSGGGSGGSA WSHPQFEK                                       28
```